US008900871B2

(12) United States Patent
Okita et al.

(10) Patent No.: US 8,900,871 B2
(45) Date of Patent: Dec. 2, 2014

(54) METHOD OF PRODUCING INDUCED PLURIPOTENT STEM CELLS USING INHIBITORS OF P53

(75) Inventors: Keisuke Okita, Kyoto (JP); Masato Nakagawa, Kyoto (JP); Shinya Yamanaka, Kyoto (JP)

(73) Assignee: Kyoto University, Kyoto (JP)

( * ) Notice: Subject to any disclaimer, the term of this patent is extended or adjusted under 35 U.S.C. 154(b) by 100 days.

(21) Appl. No.: 13/389,359

(22) PCT Filed: Aug. 6, 2010

(86) PCT No.: PCT/JP2010/063733
§ 371 (c)(1),
(2), (4) Date: Mar. 7, 2012

(87) PCT Pub. No.: WO2011/016588
PCT Pub. Date: Feb. 10, 2011

(65) Prior Publication Data
US 2012/0196360 A1 Aug. 2, 2012

Related U.S. Application Data

(60) Provisional application No. 61/232,402, filed on Aug. 7, 2009, provisional application No. 61/307,306, filed on Feb. 23, 2010.

(51) Int. Cl.
*C12N 15/00* (2006.01)
*A01N 43/04* (2006.01)
(52) U.S. Cl.
USPC .................................. 435/455; 514/44
(58) Field of Classification Search
USPC ...................... 435/325, 455; 514/44
See application file for complete search history.

(56) References Cited

U.S. PATENT DOCUMENTS

| 8,530,238 | B2 | 9/2013 | Yamanaka et al. |
| 2009/0047263 | A1 | 2/2009 | Yamanaka et al. |
| 2009/0068742 | A1 | 3/2009 | Yamanaka |
| 2010/0093090 | A1 | 4/2010 | Deng et al. |
| 2011/0039338 | A1 | 2/2011 | Yamanaka et al. |
| 2011/0223669 | A1 | 9/2011 | Yamanaka et al. |
| 2014/0011279 | A1 | 1/2014 | Yamanaka et al. |

FOREIGN PATENT DOCUMENTS

| CN | 101550406 A | 10/2009 |
| JP | 2008-528038 A | 7/2008 |
| WO | WO 2006/083782 A2 | 8/2006 |
| WO | WO 2007/069666 A1 | 6/2007 |
| WO | WO 2007/080591 A2 | 7/2007 |
| WO | WO 2008/118820 A2 | 10/2008 |
| WO | WO 2008/144580 A2 | 11/2008 |
| WO | WO 2009/057831 A1 | 5/2009 |
| WO | WO 2009/115295 A1 | 9/2009 |
| WO | WO 2009/157593 A1 | 12/2009 |

OTHER PUBLICATIONS

AIMV® Medium, liquid, Cat. No. 087-0112DK, Gibco® Invitrogen Cell Culture (2003-2004).
Chang et al., *Stem Cells*, 27: 1042-1049 (2009).
Dijon-Grinand et al., *Fertil. Steril.*, 92(3)(Supplement): S172 p. 300 (2009).
Dorigo et al., *Journal of Virology*, 78(12): 6556-6566 (2004).
Hong et al., *Nature*, 460(7259): 1132-1135 (2009).
Kaji et al., *Nature*, 458(7329): 771-775 (2009).
Kahoku-Shinpo, "Improved Efficiency of Establishment of iPS Cells", Kahoku-Shinpo Newspaper, p. 11 (Feb. 11, 2009).
Nakagawa et al., *Proc. Natl. Acad. Sci. USA*, 107(32): 14152-14157 (2010).
Nakagawa et al., *Nature Biotechnology*, 26(1): 101-106 (2008).
Okita et al., *Science*, 322: 949-953 (2008).
Rodriguez-Piza et al., *Stem Cells*, 28: 36-44 (2010).
Ross et al., *Stem Cells Dev.*, 19(8): 1221-1229 (2009).
Soldner et al., *Cell*, 136: 964-977 (2009).
Stadtfeld et al., *Science*, 322: 945-949 (2008).
STEMPRO® MSC SFM., Cat. No. A10332-01, Datasheet [online], Gibco® Invitrogen Cell Culture (2008).
Sun et al., *Proc. Natl. Acad. Sci. USA*, 106(37): 15720-15725 (2009).
Swistowski et al., *PLoS One*, 4(7): e6233 (2009).
Takahashi et al., *Cell*, 126: 663-676 (2006).
Takahashi et al., *Cell*, 131: 861-872 (2007).
Takahashi et al., PLos One, 4(12): e8067 (2009).
TrypLE™ Select, Cat. No. 12563-011, Datasheet [online], Gibco® Invitrogen Corporation (2004).
Unger et al., *Human Reprod.*, 24(10): 2567-2581 (2009).
Woltjen et al., *Nature*, 458(7239): 766-770 (2009).
Yu et al., *Science*, 318: 1917-1920 (2007).
Yu et al., *Science*, 324: 797-801 (2009).
Zhao et al., *Cell Stem Cell*, 3(5): 475-479 (2008).

(Continued)

Primary Examiner — Michael C. Wilson
(74) Attorney, Agent, or Firm — Leydig, Voit & Mayer, Ltd.

(57) ABSTRACT

Provided is a method of producing an iPS cell, comprising bringing (a) Oct3/4 or a nucleic acid that encodes the same, (b) Klf4 or a nucleic acid that encodes the same, and (c) Sox2 or a nucleic acid that encodes the same, as well as (d1) L-Myc or a nucleic acid that encodes the same and/or (d2) a functional inhibitor of p53, into contact with a somatic cell. It is preferable that (a) a nucleic acid that encodes Oct3/4, (b) a nucleic acid that encodes Klf4, (c) a nucleic acid that encodes Sox2, (d1) a nucleic acid that encodes L-Myc and (e) a nucleic acid that encodes Lin28 or Lin28b be inserted into an episomal vector having loxP sequences placed in the same orientation on the 5' and 3' sides of a vector constituent essential for the replication of the vector, that (d2) a nucleic acid that encodes an shRNA against p53 be inserted into a vector ensuring transient expression (plasmid vector and the like), and that all these nucleic acids be transferred to a somatic cell.

6 Claims, 30 Drawing Sheets
(19 of 30 Drawing Sheet(s) Filed in Color)

(56) References Cited

OTHER PUBLICATIONS

Japanese Patent Office, International Search Report in International Patent Application No. PCT/JP2010/063733 (Oct. 26, 2010).

Chinese Patent Office, First Office Action in Chinese Patent Application No. 201080035155.9 (Dec. 13, 2012).

Calao et al., "Direct effects of Bmil on p53 protein stability inactivates oncoprotein stress responses in embryonal cancer precursor cells at tumor initiation," *Oncogene*, advance online publication, doi:10.1038/onc.2012.368, pp. 1-11 (Aug. 20, 2012) [retrieved from internet on Mar. 5, 2013, at http://www.nature.com/onc/journal/vaop/ncurrent/pdf/onc2012368a.pdf].

Jin et al., *Exp. and Mol. Med.*, 42(8): 574-582 (2010).

Levine et al, *Cell Death and Differentiation*, 13: 1027-1036 (2006).

Mali et al., *Stem Cells*, 26: 1998-2005 (2008).

Ries et al., *Cell*, 103: 321-330 (Oct. 13, 2000).

Japanese Patent Office, Office Action in Japanese Patent Application No. 2012-523493 (Apr. 2, 2013).

Rowland et al., *Nature Cell Biology*, 7(11): 1074-1082 (2005).

1 colony / 2 x 10$^5$ cells 1 colony / 1 x 10$^5$ cells

MSTO | DP74 feeder

ReproCell medium

ReproCell medium | TeSR2

CellStart coat

FIG. 27
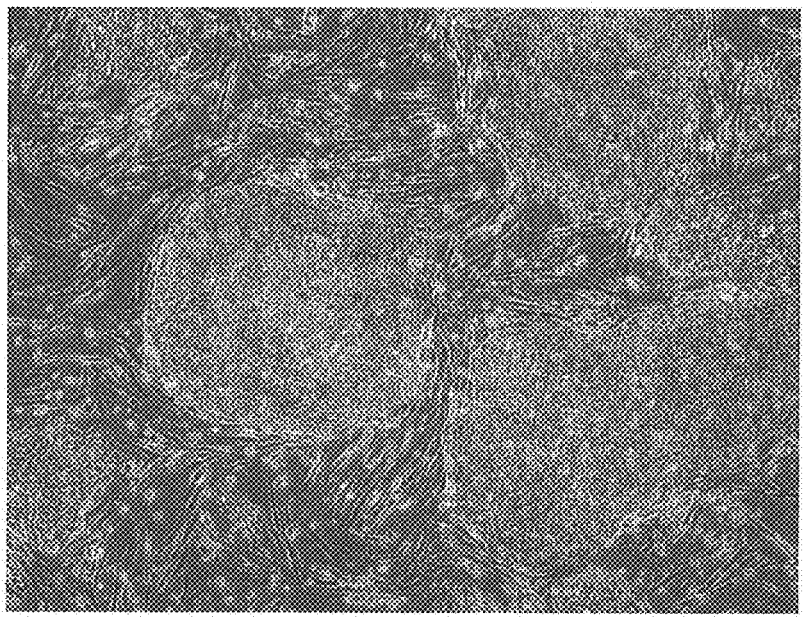
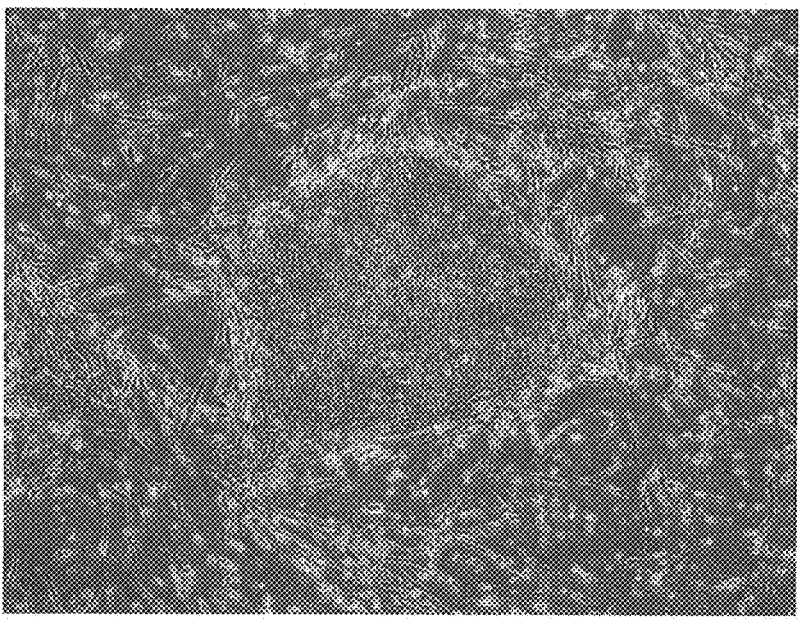

FIG. 32
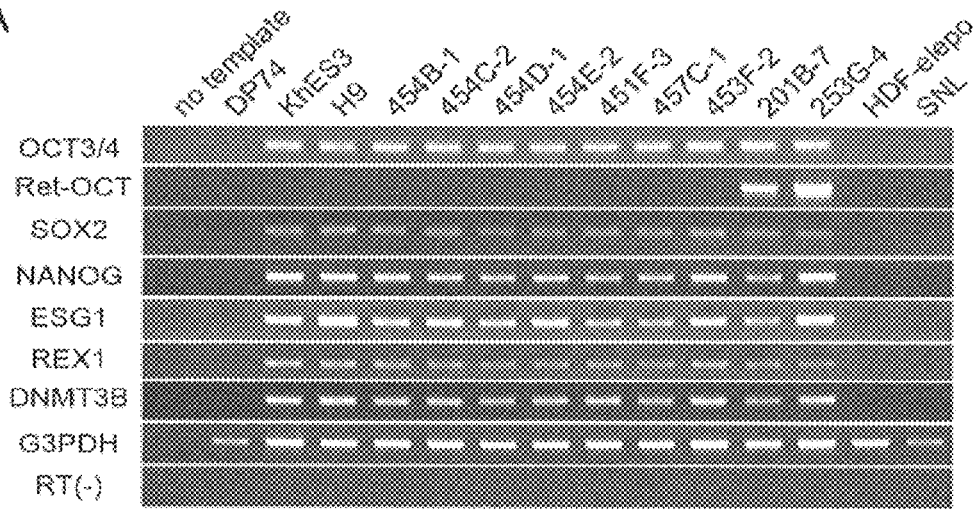
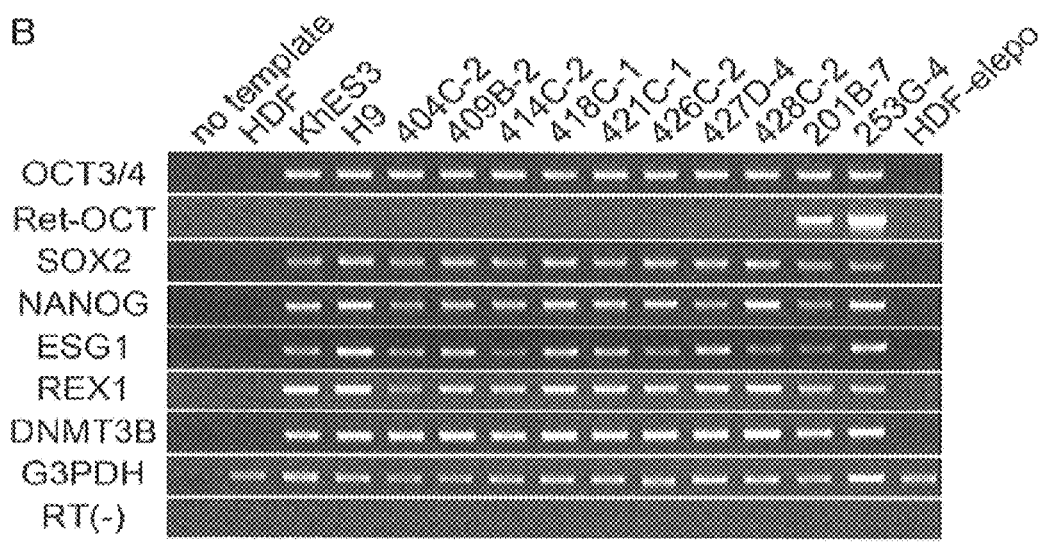

FIG. 36
a
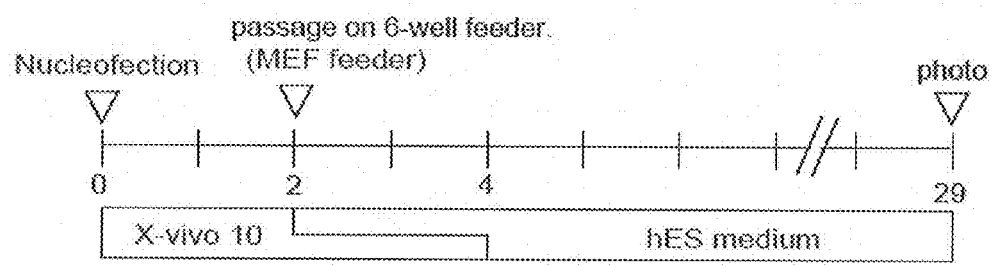
b
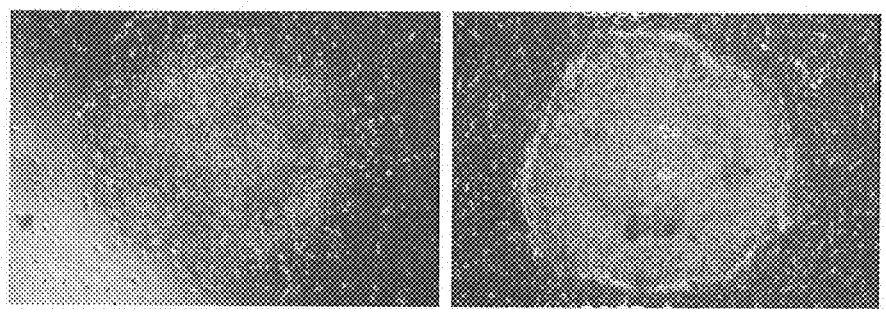

METHOD OF PRODUCING INDUCED PLURIPOTENT STEM CELLS USING INHIBITORS OF P53

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 32,439 bytes ASCII (Text) file named "709820SequenceListing.txt," created Feb. 6, 2012.

TECHNICAL FIELD

The present invention relates to a method of efficiently establishing an artificial pluripotent stem (hereinafter referred to as iPS) cell and a reagent therefor, more specifically to a method of establishing an iPS cell by bringing (a) Oct3/4 or a nucleic acid that encodes the same, (b) Klf4 or a nucleic acid that encodes the same, and (c) Sox2 or a nucleic acid that encodes the same, as well as (d1) L-Myc or a nucleic acid that encodes the same and/or (d2) a functional inhibitor of p53, into contact with a somatic cell, and to an iPS cell inducer consisting of (a) to (c) above, as well as (d1) and/or (d2). The present invention also relates to an episomal vector comprising the nucleic acid factors of (a) to (c) above, as well as the nucleic acid factors of (d1) and/or (d2), or a vector which is a combination of the episomal vector and a loxP sequence, particularly to an episomal vector of the early self-removal type, and a method of quickly establishing an iPS cell deprived of an exogenous nucleic acid factor without undergoing the integration of the nucleic acid factor in the genome using the episomal vector.

BACKGROUND OF THE INVENTION

In recent years, mouse and human iPS cells have been established one after another. Yamanaka et al. induced iPS cells by introducing the Oct3/4, Sox2, Klf4 and c-Myc genes into fibroblasts derived from a mouse, and forcing the cells to express the genes [WO 2007/069666 A1; Takahashi, K. and Yamanaka, S., Cell, 126: 663-676 (2006)]. Thereafter, it was revealed that iPS cells could also be produced with 3 factors other than the c-Myc gene [Nakagawa, M. et al., Nat. Biotechnol., 26: 101-106 (2008)]. Furthermore, Yamanaka et al. succeeded in establishing iPS cells by introducing the same 4 genes as those used in the mouse into human dermal fibroblasts [WO 2007/069666 A1; Takahashi, K. et al., Cell, 131: 861-872 (2007)]. On the other hand, a group of Thomson et al. produced human iPS cells using Nanog and Lin28 in place of Klf4 and c-Myc [WO 2008/118820 A2; Yu, J. et al., Science, 318: 1917-1920 (2007)].

However, the efficiency of iPS cell establishment is low at less than 1%. Especially, a problem of extremely low efficiency of iPS cell establishment occurs when they are produced by introducing 3 factors (Oct3/4, Sox2 and Klf4) other than c-Myc, which is feared to cause tumorigenesis in tissues or individuals differentiated from iPS cells, into somatic cells.

Viral vectors such as retroviruses and lentiviruses offer higher transfection efficiency than non-viral vectors, and are therefore favorable in that they enable easier generation of iPS cells. However, retroviruses and lentiviruses become integrated in the chromosome, posing a problem with safety in view of the clinical application of iPS cells. For this reason, iPS cells generated using adenovirus vectors or non-viral vectors such as plasmids without vector integration in the chromosome have been reported [Stadtfeld, M. et al., Science, 322: 945-949 (2008); Okita, K. et al., Science, 322: 949-953 (2008); Yu, J. et al., Science, 324: 797-801 (2009)]. However, these vectors are lower in iPS cell establishment efficiency than retroviruses and lentiviruses. Possibly because of the requirement of persistent high expression of reprogramming factor under iPS cell selection conditions, there are some cases in which a stable expression line having a reprogramming factor incorporated in the chromosome at a certain frequency is obtained even when using a plasmid vector, which is generally recognized as being unlikely to cause the incorporation [Okita, K. et al., Science, 322: 949-953 (2008); Kaji, K. et al., Nature, 458: 771-775 (2009)].

Hence, attempts have been made to reconcile high establishment efficiency and safety by first establishing an iPS cell using a retrovirus or lentivirus, then removing the exogenous genes from the chromosome. For example, techniques comprising a combination of a lentivirus and the Cre-loxP system have been reported [Chang, C. W. et al., Stem Cells, 27: 1042-1049 (2009); Soldner, F. et al., Cell, 136: 964-977 (2009)]. In these reports, however, a complex construct is used wherein a loxP sequence is inserted in the LTR to minimize the risk of activation of an oncogene in the vicinity by an LTR sequence outside the loxP sequence that remains after Cre recombinase treatment, and wherein another promoter such as CMV or EF1α is inserted for transcribing a reprogramming factor; therefore, there is a demand for the development of a vector that can be constructed more easily. Although exogenous nucleic acid factors can be completely eliminated of using piggyBac transposon [Kaji, K. et al., Nature, 458: 771-775 (2009)], the possibility of disturbing endogenous genes cannot be ruled out because transient integration in the genome is unavoidable.

Meanwhile, in the method involving the use of an episomal vector capable of stable self-replication outside the chromosome, in addition to the above-described low iPS cell establishment efficiency, the spontaneous clearance of the vector upon discontinuation of drug selection is of low efficiency and takes a long time [Yu, J. et al., Science, 324: 797-801 (2009)]. For this reason, there is a need for a method of removing the vector in a short time with high efficiency, while improving iPS cell establishment efficiency.

Furthermore, another problem arises in finding clinical applications for human iPS cells; the cells can become contaminated with ingredients derived from other animal species such as serum and feeder cells during iPS cell establishment and maintenance culture. It is desirable, therefore, that all operations, from reprogramming factor transfer to human iPS cell establishment and maintenance culture, be performed under "Xeno-free" conditions (no heterologous ingredients contained). However, it has been traditional practice that in human iPS cells established under virus-free conditions, heterologous ingredients are used in at least one step from reprogramming factor transfer to iPS cell establishment and maintenance culture [Okita, K. et al., Science, 322: 949-953 (2008); Yu, J. et al., Science, 324: 797-801 (2009); Kaji, K. et al., Nature, 458: 771-775 (2009)]. Meanwhile, all the human iPS cells established under Xeno-free conditions have been transfected with reprogramming genes by means of a retrovirus or lentivirus, and none of them have been prepared under virus-free conditions [Rodoriguez-Piza, I. et al., Stem Cells, 28: 36-44 (2010); Ross, P. J. et al., Stem Cells Dev., 2009 Dec. 23. (Epub ahead of print)].

SUMMARY OF THE INVENTION

The present invention is directed to efficiently establishing a safe human iPS cell suitable for clinical application. Accordingly, it is a first object of the present invention to provide a means to improve the efficiency of establishment of iPS cells, particularly human iPS cells, and a method of efficiently producing an iPS cell by using the means. It is a second object of the present invention to provide a method of quickly establishing an iPS cell that has lost exogenous nucleic acid factors without undergoing the integration of the nucleic acid factors in the genome. It is a third object of the present invention to generate a human iPS cell without using any viruses or heterologous ingredients during the period from reprogramming factor transfer and iPS cell establishment and maintenance culture (i.e., under virus-free xeno-free conditions) to thereby provide a human iPS cell that can be safely used in human clinical settings.

To solve the problems described above, the present inventors first investigated to find suitable combinations of reprogramming genes using a retroviral vector. Based on the 6 factors used by Yu, J. et al. for establishing a human iPS cell using an episomal vector [Oct3/4, Klf4, c-Myc, Sox2, Nanog, Lin28 (SV40 Large T antigen handled as an establishment efficiency improver, and excluded from the reprogramming genes)] [*Science*, 324: 797-801 (2009)], the present inventors attempted to induce a human iPS cell from a human dermal fibroblast (HDF) using 5 factors except Nanog, or using 5 factors except Nanog, which include L-Myc in place of c-Myc. Unexpectedly, a human iPS cell was established more efficiently with the use of the 5 factors other than Nanog than with the 6 factors. Furthermore, as a result of replacement of c-Myc with L-Myc, the establishment efficiency improved remarkably. Hence, human iPS cell establishment efficiency was actually compared between the use of the 6 factors and the use of the 5 factors including L-Myc in place of c-Myc, using an episomal vector. As a result, it was found that the establishment efficiency increased remarkably with the use of the 5 factors including L-Myc in place of c-Myc, compared with the 6 factors.

Next, the 6 factors or the 5 factors other than Nanog and including L-Myc in place of c-Myc, along with an episomal vector that encodes an shRNA against p53, were transferred to HDF. As a result of functional inhibition of p53, iPS cells were obtained with the use of the 6 factors to similar extent compared with the 5 factors including L-Myc in place of c-Myc. When the 5 factors were combined with functional inhibition of p53, the establishment efficiency increased still more remarkably. It was also found that by using mouse embryonic fibroblasts (MEF), rather than SNL cells, as feeder cells at the time of passage of HDF after transfection, the human iPS cell establishment efficiency improved dramatically.

The present inventors had designed the episomal vector to allow a constituent thereof essential for the self-replication thereof to be cut out therefrom by the action of Cre recombinase with a loxP sequence placed at both ends of the vector constituent so as to allow the transferred episomal vector to be shed from the iPS cell quickly after establishment of the iPS cell. After establishment of the human iPS cell, the cell's genomic DNA and extrachromosomal DNA were isolated and separately examined for the presence or absence of the transgenes. As a result, the transferred vector was not detected in either DNA; unexpectedly, the vector was found to be an early self-removal vector quickly shedding from the cell, without using Cre recombinase.

Furthermore, the present inventors succeeded in generating a human iPS cell under completely virus-free and xeno-free conditions from reprogramming factor transfer to iPS cell establishment and maintenance culture, using the above-described episomal vector.

From these results, the present inventors found that human iPS cell establishment efficiency can be improved remarkably by excluding Nanog from the reprogramming factors and using L-Myc in place of c-Myc, or using a functional inhibitor of p53 in place thereof, or in addition thereto, that an iPS cell that has lost exogenous nucleic acid factors without undergoing the integration of the nucleic acid factors in the genome can be acquired quickly by elaborating the design of an episomal vector, and that a human iPS cell can be generated under virus-free and xeno-free conditions by combining the above-described reprogramming factors and episomal vector, and have developed the present invention.

Accordingly, the present invention provides:

[1] A method of producing an iPS cell, comprising bringing (a) Oct3/4 or a nucleic acid that encodes the same, (b) Klf4 or a nucleic acid that encodes the same, and (c) Sox2 or a nucleic acid that encodes the same, as well as (d1) L-Myc or a nucleic acid that encodes the same and/or (d2) a functional inhibitor of p53, into contact with a somatic cell.

[2] The method according to [1] above, further comprising bringing (e) Lin28 or Lin28b or a nucleic acid that encodes the same into contact with the somatic cell.

[3] The method according to [1] or [2] above, wherein the functional inhibitor of p53 is a nucleic acid selected from the group consisting of siRNAs and shRNAs against p53 and DNAs that encode the same.

[4] The method according to [2] or [3] above, comprising transferring (a) a nucleic acid that encodes Oct3/4, (b) a nucleic acid that encodes Klf4, (c) a nucleic acid that encodes Sox2, (d1) a nucleic acid that encodes L-Myc and/or (d2) a nucleic acid that encodes an shRNA against p53, as well as (e) a nucleic acid that encodes Lin28 or Lin28b, to a somatic cell.

[5] The method according to [4] above, wherein at least one nucleic acid selected from the group consisting of the foregoing (a), (b), (c), (d1) and (e) is transferred in the form of an episomal vector.

[6] The method according to [4] or [5] above, wherein (d2) the nucleic acid that encodes an shRNA against p53 is transferred in the form of a plasmid vector incapable of self-replicating in cells.

[7] The method according to [5] or [6] above, wherein the episomal vector is a self-removal vector shedding from the iPS cell by the 5th passage at a frequency of 50% or more.

[8] The method according to any one of [5] to [7] above, wherein the episomal vector has loxP sequences placed in the same orientation on the 5' and 3' sides of a vector constituent essential for the replication of the nucleic acid.

[9] The method according to [8] above, not comprising the process of treating the cell with Cre recombinase.

[10] The method according to any one of [1] to [9] above, wherein the somatic cell is a human cell.

[11] The method according to [10] above, comprising culturing a cell in the absence of an ingredient from a non-human animal during the period from contact of the foregoing factors (a), (b), (c), as well as (d1) and/or (d2), or additional (e), with the somatic cell to the establishment of an iPS cell.

[12] The method according to [11] above, wherein human cells are used as feeder cells, or wherein no feeder cells are used.

[13] The method according to [12] above, wherein the feeder cells are derived from the same individual as the somatic cell.

[14] An iPS cell induction promoting agent comprising (a) a nucleic acid that encodes Oct3/4, (b) a nucleic acid that encodes Klf4, (c) a nucleic acid that encodes Sox2, (d1) a nucleic acid that encodes L-Myc and/or (d2) a nucleic acid that encodes an shRNA against p53, as well as (e) a nucleic acid that encodes Lin28 or Lin28b.

[15] The agent according to [14] above, wherein at least one nucleic acid selected from the group consisting of the foregoing (a), (b), (c), (d1) and (e) is in the form of an episomal vector.

[16] The agent according to [14] or [15] above, wherein (d2) the nucleic acid that encodes an shRNA against p53 is in the form of a plasmid vector incapable of self-replication in cells.

[17] The agent according to [15] or [16] above, wherein the episomal vector is a self-removal vector shedding from the iPS cell by the 5th passage at a frequency of 50% or more.

[18] The agent according to any one of [15] to [17] above, wherein the episomal vector has loxP sequences placed in the same orientation on the 5' and 3' sides of a vector constituent essential for the replication of each of the foregoing nucleic acids.

[19] An iPS cell that has lost the foregoing nucleic acids without undergoing the integration of the nucleic acids in the genome, obtained by the method according to any one of [5] to [9] above.

[20] The iPS cell according to [19] above, which is a human iPS cell.

[21] A human iPS cell free of any contaminating ingredient from a non-human animal, obtained by the method according to any one of [11] to [13] above.

[22] A use of the iPS cell according to any one of [19] to [21] above in producing a somatic cell.

[23] The iPS cell according to any one of [19] to [21] above, wherein the iPS cell serves as a source of cell in producing a somatic cell.

The use of L-Myc in place of c-Myc and/or use of a functional inhibitor of p53, as well as the non-use of Nanog, makes it possible to increase iPS cell establishment efficiency remarkably, and is therefore particularly useful in generating a human iPS cell, particularly a human iPS cell of the type that does not involve the integration of reprogramming genes in the genome, with the use of 6 factors that have been extremely low in establishment efficiency (Oct3/4, Klf4, Sox2, c-Myc, Nanog, Lin28). Additionally, the use of an independently developed episomal vector makes it possible to establish an iPS cell without involving the integration of exogenous nucleic acid factors in the genome, and to cause the episome to be shed quickly from the iPS cell after establishment thereof, whereby the vector can be shed from the cell earlier than conventional episomal vectors. Furthermore, because a human iPS cell can be generated under completely virus-free and xeno-free conditions during the period from reprogramming factor transfer to iPS cell establishment and maintenance, the method of the present invention is highly useful in applying human iPS cells to regenerative medicine.

In the following, the iPS cell established by the use of an episomal vector is sometimes abbreviated as "epi-iPS cells" or "epi-iPSCs" in the present specification.

In addition, when the combination of introduced genes is abbreviated as "Y1, Y2, Y3, Y4, T1, T2 or T3", the combination is as shown in the Table 1 below.

TABLE 1

Summary of plasmid mixtures.

| Mixture name | Plasmid name | Amount (ug) | Genes |
|---|---|---|---|
| Y1 | pCXLE-hOct4 | 1 | OCT3/4 |
| | pCXLE-hSK | 1 | SOX2, KLF4 |
| | pCXLE-hMLN | 1 | C-MYC, LIN28, NANOG |
| Y2 | pCXLE-hOct4shp53 | 1 | OCT3/4, shRNA for p53 |
| | pCXLE-hSK | 1 | SOX2, KLF4 |
| | pCXLE-hMLN | 1 | C-MYC, LIN28, NANOG |
| Y3 | pCXLE-hOct4 | 1 | OCT3/4 |
| | pCXLE-hSK | 1 | SOX2, KLF4 |
| | pCXLE-hUL | 1 | L-MYC, LIN28 |
| Y4 | pCXLE-hOct4shp53 | 1 | OCT3/4, shRNA for p53 |
| | pCXLE-hSK | 1 | SOX2, KLF4 |
| | pCXLE-hUL | 1 | L-MYC, LIN28 |
| T1 | pEP4EO2SET2K | 1.125 | OCT3/4, SOX2, SV40LT, KLF4 |
| | pEP4EO2SEN2K | 1.125 | OCT3/4, SOX2, NANOG, KLF4 |
| | pCEP4-M2L | 0.75 | C-MYC, LIN28 |
| T2 | pEP4EO2SET2K | 0.91 | OCT3/4, SOX2, SV40LT, KLF4 |
| | pEP4EO2SCK2MEN2L | 2.09 | OCT3/4, SOX2, KLF4, C-MYC, NANOG, LIN28 |
| T3 | pEP4EO2SET2K | 0.8 | OCT3/4. SOX2, SV40LT, KLF4 |
| | pEP4EO2SEN2L | 1.05 | OCT3/4, SOX2, NANOG, LIN28 |
| | pEP4EO2SEM2K | 1.15 | OCT3/4, SOX2, C-MYC, KLF4 |

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIG. 2, "6 factors" indicates a case where the Oct3/4, Sox2, Klf4, Lin28, Nanog, and c-Myc or L-Myc genes were transferred; "ctrl" indicates a case where 5 genes other than Nanog in the foregoing 6 genes were transferred; "L-M", "M-L", "L-U", and "U-L" indicate cases where a construct with each factor (L stands for Lin28, M for c-Myc, U for L-Myc) joined therein and Oct3/4, Sox2 and Klf4 were transferred.

In FIG. 12, "endo" (outlined arrowhead) stands for an endogenous gene, and Tg (solid arrowhead) for an exogenous gene.

In FIG. 20, "elepoD4" stands for cells on day 4 after transfection, and "KhES1" and "KhES3" for human ES cells.

FIG. 27 is a photographic representation showing the morphology of cells as of the 1st passage obtained by culturing an iPS cell established using an episomal vector under Xeno-free conditions (Xeno-free medium used, and the DP74 line used as feeder cells).

FIG. 32 shows expressions of pluripotent cell marker genes by an RT-PCR analysis. A: the results of DP-derived epi-iPS cells. B: the results of fibroblast-derived epi-iPS cells. Total RNA was isolated from epi-iPSC clones established with the Y1 (454B-1), Y2 (454C-2), Y3 (454D-1), and Y4 (454E-2, 451F-3, 457C-1, 453F-2, 404C-2, 409B-2, 414C-2, 418C-1, 421C-1, 426C-2, 427D-4, and 428C-2) combinations. Retrovirus-derived iPSC clones (201B-7 and 253G-4), and hESC lines (KhES-3 and H9) were also examined. In the lanes labeled OCT3/4 and Sox2, the PCR primers only amplified the endogenous genes, whereas in the Ret-Oct lane, the PCR primers specifically amplified the retroviral Oct3/4 transgene. G3PDH was analyzed as a loading control. As negative controls, total RNA was isolated from human dermal fibroblasts 4 days after electroporation of the Y4 mixture (HDF-elepo).

FIG. 34 shows teratoma derived from an epi-iPSC clone.

FIG. 35 shows differentiation into dopaminegic neurons from an epi-iPSC clone (clone 454E-2).

FIG. 36 shows the establishment of iPS cells from human peripheral blood mononuclear cells. FIG. 36a shows an outline of the experimental procedure. FIG. 36b is a photographic representation of colonies of iPS cell established by transferring the three different plasmids pCXLE-hOct4-shp53, pCXLE-hSK and pCXLE-hUL to human peripheral blood mononuclear cells.

DETAILED DESCRIPTION OF THE INVENTION

Figure 1:
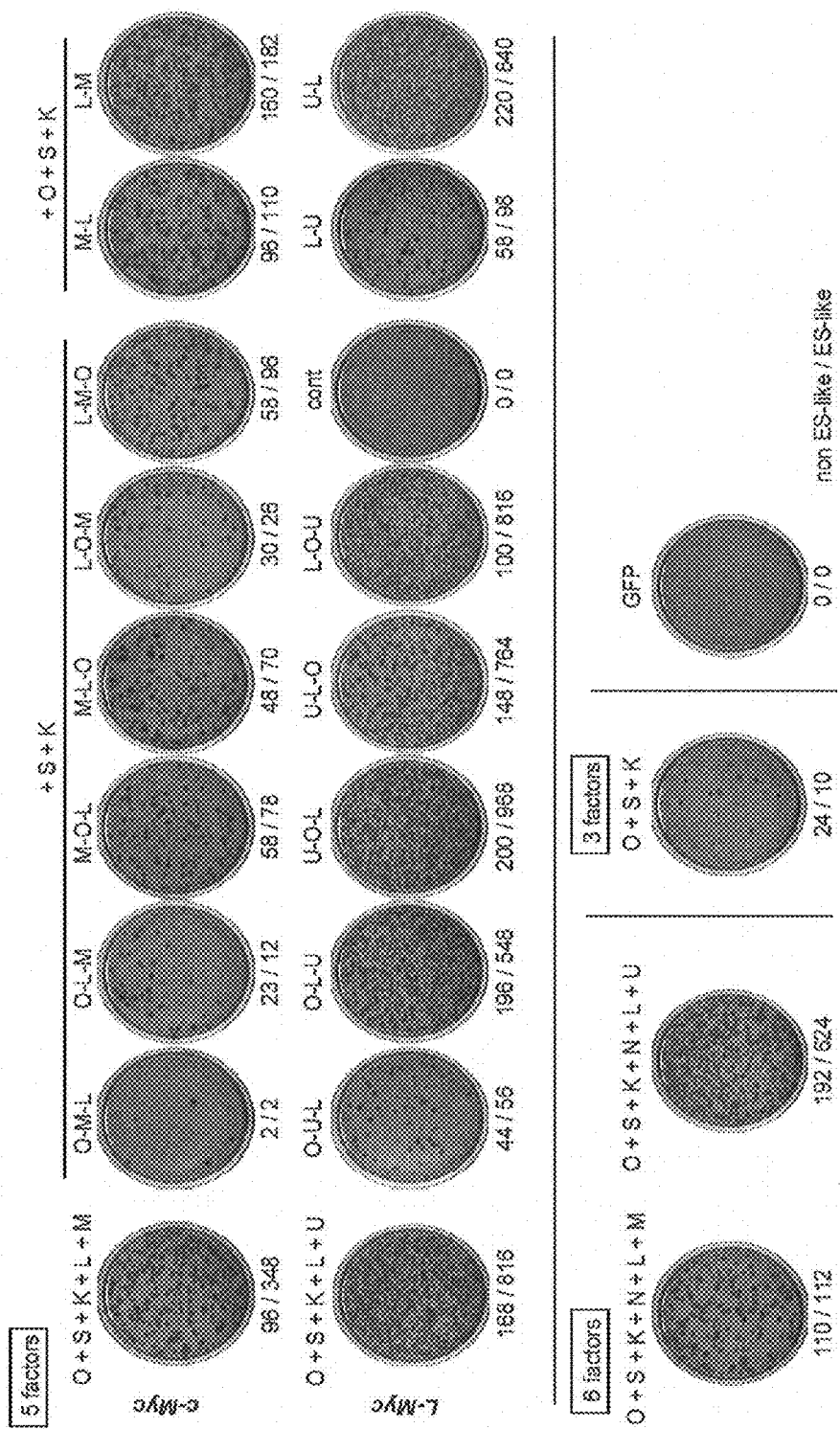
FIG. 1 is a photographic representation of colonies of human iPS cells established by transferring various genes to neonatal human dermal fibroblasts using a retrovirus, wherein O stands for Oct3/4, S for Sox2, K for Klf4, L for Lin28, N for Nanog, M for c-Myc, and U for L-Myc. A joint representation of factors like "O-M-L" indicates a construct prepared by joining the translated regions of the factors via a 2A sequence. The number under each photograph indicates the number of non-ES-like colonies/the number of ES-like colonies.

The present invention provides a method of producing an iPS cell, comprising bringing (a) Oct3/4 or a nucleic acid that encodes the same, (b) Klf4 or a nucleic acid that encodes the same, and (c) Sox2 or a nucleic acid that encodes the same, as well as (d1) L-Myc or a nucleic acid that encodes the same and/or (d2) a functional inhibitor of p53, into contact with a somatic cell.

(A) Sources of Somatic Cells

Any cells other than germ cells of mammalian origin (e.g., humans, mice, monkeys, pigs, rats etc.) can be used as starting material for the production of iPS cells. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., bacillary cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells (tissue progenitor cells) thereof and the like. There is no limitation on the degree of cell differentiation, the age of an animal from which cells are collected and the like; even undifferentiated progenitor cells (including somatic stem cells) and finally differentiated mature cells can be used alike as sources of somatic cells in the present invention.

Examples of undifferentiated progenitor cells include tissue stem cells (somatic stem cells) such as nerve stem cells, hematopoietic stem cells, mesenchymal stem cells, adipose-derived stromal (stem) cells and dental pulp stem cells. Hematopoietic and mesenchymal stem cells are abundantly contained in bone marrow, umbilical cord blood and placenta. Since bone marrow, umbilical cord bloods and placenta have been deposited into many blood banks, both public and private, and used for the treatment of blood diseases such as leukemia, such deposited bone marrow, umbilical cord bloods and placenta can also be utilized as a source of somatic cells for iPS cell banks. In particular, since umbilical cord bloods can be easily collected from umbilical cords obtained at the time of childbirth, hematopoietic and mesenchymal stem cells obtained from umbilical cord bloods are preferable sources of somatic cells for iPS cell banks. Dental pulp stem cells are also expected to serve a source of somatic cells for iPS cell banks, since they are easily available as isolated and prepared from wisdom teeth and other teeth extracted for the treatment of periodontal disease and the like.

Examples of finally differentiated mature cells include peripheral blood mononuclear cells such as T cells and B cells. Sampling of peripheral blood is a minimally invasive and routinely performed in clinical assays. Since a small volume of peripheral blood samples left unused after clinical assays are usually discarded, they are preferable sources of somatic cells for iPS cell banks. In particular, since T cells can be expanded in vitro with relative ease, iPS cells can be established from even a small volume of peripheral blood samples. The generation of iPS cells from human peripheral blood T cells has been recently reported by several groups (Seki et al., *Cell Stem Cell*, 7: 11-14 (2010); Loh et al., *Cell Stem Cell*, 7: 15-19 (2010); Staerk et al., *Cell Stem Cell*, 7: 20-24 (2010)).

The choice of mammal individual as a source of somatic cells is not particularly limited; however, when the iPS cells obtained are to be used for regenerative medicine in humans, it is preferable, from the viewpoint of prevention of graft rejection, to collect the somatic cells from a patient or another person with the same or substantially the same HLA type as that of the patient. "Substantially the same HLA type" as used herein means that the HLA type of donor matches with that of patient to the extent that the transplanted cells, which have been obtained by inducing differentiation of iPS cells derived from the donor's somatic cells, can be engrafted when they are transplanted to the patient with use of immunosuppressant and the like. For example, it includes an HLA type wherein major HLAs (e.g., the three major loci of HLA-A, HLA-B and HLA-DR, the four major loci further including HLA-Cw) are identical (hereinafter the same meaning shall apply) and the like. When the iPS cells obtained are not to be administered (transplanted) to a human, but used as, for example, a source of cells for screening for evaluating a patient's drug susceptibility or adverse reactions, it is likewise desired to collect the somatic cells from the patient or another person with the same genetic polymorphism correlating with the drug susceptibility or adverse reactions.

Somatic cells isolated from a mammal can be pre-cultured using a medium known per se suitable for their cultivation according to the choice of cells before being subjected to the step of nuclear reprogramming. Examples of such media include, but are not limited to, minimal essential medium (MEM) containing about 5 to 20% fetal calf serum (FCS), Dulbecco's modified Eagle medium (DMEM), RPMI1640 medium, 199 medium, F12 medium, and the like. When a dental pulp stem cell is used as the somatic cell, for example, it is preferable to use a medium for mesenchymal stem cells, such as the Mesenchymal Stem Cell Basal Medium (Lonza). When a transfer reagent such as cationic liposome, for example, is used in bringing the somatic cell into contact with nuclear reprogramming substances and a functional inhibitor of p53 (and another iPS cell establishment efficiency improver if required), it is sometimes preferable that the medium have been replaced with a serum-free medium so as to prevent the transfer efficiency from decreasing.

To obtain completely xeno-free human iPS cells suitable for human clinical applications, it is more desirable that a medium that does not contain any ingredients derived from non-human animals, such as FCS, be used. Media comprising a basal medium supplemented with human-derived ingredients suitable for cultivation of various somatic cells (particularly, recombinant human proteins such as growth factors), non-essential amino acids, vitamins and the like are commercially available; those skilled in the art are able to choose an appropriate xeno-free medium according to the source of somatic cells. Somatic cells pre-cultured using a xeno-free medium are dissociated from the culture vessel using an appropriate xeno-free cell dissociation solution, and recovered, after which they are brought into contact with nuclear reprogramming substances and a functional inhibitor of p53.

(B) Nuclear Reprogramming Substances

As used herein, "a nuclear reprogramming substance" can be a proteinous factor(s) capable of inducing an iPS cell from a somatic cell or a nucleic acid that encodes the same (including forms integrated in a vector). The nuclear reprogramming substances used in the present invention consist of at least Oct3/4, Klf4 and Sox2 or nucleic acids that encode the same (Klf4 and/or Sox2 may be replaced with another factor that has been reported to be capable of substituting for the function thereof). When no functional inhibitor of p53 is used in combination, L-Myc or a nucleic acid that encodes the same, and Lin28 or Lin28b or a nucleic acid that encodes the same, are combined as additional nuclear reprogramming substances. The nuclear reprogramming substances used in the present invention exclude Nanog or a nucleic acid that encodes the same. Specifically, the nuclear reprogramming substances used in the present invention are exemplified by the following combinations (here, only the names for proteinous factors are shown):
(1) Oct3/4, Klf4, Sox2, L-Myc (here, Sox2 is replaceable with Sox1, Sox3, Sox15, Sox17 or Sox18; Klf4 is replaceable with Klf1, Klf2 or Klf5)
(2) Oct3/4, Klf4, Sox2, L-Myc, TERT, SV40 Large T antigen (hereinafter, SV40LT)
(3) Oct3/4, Klf4, Sox2, L-Myc, TERT, HPV16 E6
(4) Oct3/4, Klf4, Sox2, L-Myc, TERT, HPV16 E7
(5) Oct3/4, Klf4, Sox2, L-Myc, TERT, HPV16 E6, HPV16 E7
(6) Oct3/4, Klf4, Sox2, L-Myc, TERT, Bmi1
(7) Oct3/4, Klf4, Sox2, L-Myc, Lin28
(8) Oct3/4, Klf4, Sox2, L-Myc, Lin28, SV40LT
(9) Oct3/4, Klf4, Sox2, L-Myc, Lin28, TERT, SV40LT
(10) Oct3/4, Klf4, Sox2, L-Myc, SV40LT
(11) Oct3/4, Esrrb, Sox2, L-Myc (Esrrb is replaceable with Esrrg)
(12) Oct3/4, Klf4, Sox2
(13) Oct3/4, Klf4, Sox2, TERT, SV40LT
(14) Oct3/4, Klf4, Sox2, TERT, HPV16 E6
(15) Oct3/4, Klf4, Sox2, TERT, HPV16 E7
(16) Oct3/4, Klf4, Sox2, TERT, HPV16 E6, HPV16 E7
(17) Oct3/4, Klf4, Sox2, TERT, Bmi1
(18) Oct3/4, Klf4, Sox2, Lin28
(19) Oct3/4, Klf4, Sox2, Lin28, SV40LT
(20) Oct3/4, Klf4, Sox2, Lin28, TERT, SV40LT
(21) Oct3/4, Klf4, Sox2, SV40LT
(22) Oct3/4, Esrrb, Sox2 (Esrrb is replaceable with Esrrg)

In the combinations above, Lin28b can be used in place of Lin28. When using Esrrb or Esrrg [(11) and (22) above], Klf4 may be used in combination therewith.

Any combination that does not fall in (1) to (22) above but comprises all the constituents of any one of (1) to (22) and further comprises an optionally chosen other substance can also be included in the scope of "nuclear reprogramming substances" in the present invention. Provided that the somatic cell to undergo nuclear reprogramming is endogenously expressing one or more of the constituents of any one of (1) to (22) above at a level sufficient to cause nuclear reprogramming, a combination of only the remaining constituents excluding the one or more constituents can also be included in the scope of "nuclear reprogramming substances" in the present invention.

Of these combinations, 5 factors consisting of Oct3/4, Sox2, Klf4, Lin28 (Lin28b) and L-Myc, and 4 factors consisting of Oct3/4, Sox2, Klf4 and Lin28 (Lin28b) are preferred nuclear reprogramming substances. Also preferred are 6 or 5 factors consisting of the above 5 or 4 factors and additional SV40 Large T antigen.

Information on the mouse and human cDNA sequences of the aforementioned nuclear reprogramming substances is available with reference to the NCBI accession numbers mentioned in WO 2007/069666 (in the publication, Nanog is described as ECAT4. Mouse and human cDNA sequence information on Lin28, Lin28b, Esrrb, Esrrg, L-Myc can be acquired by referring to the following NCBI accession numbers, respectively); those skilled in the art are easily able to isolate these cDNAs.

| Name of gene | Mouse | Human |
| --- | --- | --- |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| L-Myc | NM_008506 | NM_001033081 |

A proteinous factor for use as a nuclear reprogramming substance can be prepared by inserting the cDNA obtained into an appropriate expression vector, introducing the vector into a host cell, and recovering the recombinant proteinous factor from the cultured cell or its conditioned medium. Meanwhile, when the nuclear reprogramming substance used is a nucleic acid that encodes a proteinous factor, the cDNA obtained is inserted into a viral vector, plasmid vector, episomal vector etc. to construct an expression vector, and the vector is subjected to the step of nuclear reprogramming.

(c) Method of Transferring a Nuclear Reprogramming Substance to a Somatic Cell

Transfer of a nuclear reprogramming substance to a somatic cell can be achieved using a method known per se for protein transfer into a cell, provided that the substance is a proteinous factor. Such methods include, for example, the method using a protein transfer reagent, the method using a protein transfer domain (PTD)—or cell penetrating peptide (CPP)—fusion protein, the microinjection method and the like. Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IMGENEX); those based on a lipid, such as Profect-1 (Targeting Systems); those based on a membrane-permeable peptide, such as Penetrain Peptide (Q biogene) and Chariot Kit (Active Motif), GenomONE (ISHIHARA SANGYO KAISHA, LTD.) utilizing HVJ envelope (inactivated hemagglutinating virus of Japan) and the like. The transfer can be achieved per the protocols attached to these reagents, a common procedure being as described below. Nuclear reprogramming substance(s) is(are) diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium.

Developed PTDs include those using transcellular domains of proteins such as drosophila-derived AntP, HIV-derived TAT (Frankel, A. et al, Cell 55, 1189-93 (1988) or Green, M. & Loewenstein, P. M. Cell 55, 1179-88 (1988)), Penetratin (Derossi, D. et al, J. Biol. Chem. 269, 10444-50 (1994)), Buforin II (Park, C. B. et al. Proc. Natl Acad. Sci. USA 97, 8245-50 (2000)), Transportan (Pooga, M. et al. FASEB J. 12, 67-77 (1998)), MAP (model amphipathic peptide) (Oehlke, J. et al. Biochim. Biophys. Acta. 1414, 127-39 (1998)), K-FGF (Lin, Y. Z. et al. J. Biol. Chem. 270, 14255-14258 (1995)), Ku70 (Sawada, M. et al. Nature Cell Biol. 5, 352-7 (2003)), Prion (Lundberg, P. et al. Biochem. Biophys. Res. Commun. 299, 85-90 (2002)), pVEC (Elmquist, A. et al. Exp. Cell Res. 269, 237-44 (2001)), Pep-1 (Morris, M. C. et al. *Nature Biotechnol.* 19, 1173-6 (2001)), Pep-7 (Gao, C. et al. *Bioorg. Med. Chem.* 10, 4057-65 (2002)), SynB1 (Rousselle, C. et al. *Mol. Pharmacol.* 57, 679-86 (2000)), HN-I (Hong, F. D. & Clayman, G L. *Cancer Res.* 60, 6551-6 (2000)), and HSV-derived VP22. CPPs derived from the PTDs include polyarginines such as 11R (*Cell Stem Cell*, 4, 381-384 (2009)) and 9R (*Cell Stem Cell*, 4, 472-476 (2009)).

A fused protein expression vector incorporating cDNA of a nuclear reprogramming substance and PTD or CPP sequence is prepared, and recombination expression is performed using the vector. The fused protein is recovered and used for transfer. Transfer can be performed in the same manner as above except that a protein transfer reagent is not added.

Microinjection, a method of placing a protein solution in a glass needle having a tip diameter of about 1 µm, and injecting the solution into a cell, ensures the transfer of the protein into the cell.

The protein transferring operation can be performed one or more optionally chosen times (e.g., once or more to 10 times or less, or once or more to 5 times or less and the like). Preferably, the transferring operation can be performed twice or more (e.g., 3 times or 4 times) repeatedly. The time interval for repeated transferring operation is, for example, 6 to 48 hours, preferably 12 to 24 hours.

However, taking into account the efficiency of establishment of iPS cells, nuclear reprogramming substance may be used preferably in the form of a nucleic acid that encodes a proteinous factor, rather than the factor as it is. The nucleic acid may be a DNA or an RNA, or a DNA/RNA chimera, and may be double-stranded or single-stranded. Preferably, the nucleic acid is a double-stranded DNA, particularly a cDNA.

A cDNA of a nuclear reprogramming substance is inserted into an appropriate expression vector comprising a promoter capable of functioning in a host somatic cell. Useful expression vectors include, for example, viral vectors such as retrovirus, lentivirus, adenovirus, adeno-associated virus, herpesvirus and Sendai virus, plasmids for the expression in animal cells (e.g., pA1-11, pXT1, pRc/CMV, pRc/RSV, pcDNAI/Neo) and the like.

The type of a vector to be used can be chosen as appropriate according to the intended use of the iPS cell to be obtained. Useful vectors include adenovirus vector, plasmid vector, adeno-associated virus vector, retroviral vector, lentiviral vector, Sendai virus vector, episomal vector and the like.

Examples of promoters used in expression vectors include the EF1α promoter, the CAG promoter, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EF1α promoter, the CAG promoter, the MoMuLV LTR, the CMV promoter, the SRα promoter and the like.

The expression vector may contain as desired, in addition to a promoter, an enhancer, a polyadenylation signal, a selectable marker gene, a SV40 replication origin and the like. Examples of selectable marker genes include the dihydrofolate reductase gene, the neomycin resistant gene, the puromycin resistant gene and the like.

The nucleic acids which are nuclear reprogramming substances (reprogramming genes) may be separately integrated into different expression vectors, or 2 or more, preferably 2 to 3, different genes may be integrated into a single expression vector. Preference is given to the former case with the use of a retroviral or lentiviral vector, which offer high transfection efficiency, and to the latter case with the use of a plasmid, adenovirus, or episomal vector and the like. Furthermore, an expression vector incorporating two or more different genes and another expression vector incorporating one gene alone can be used in combination.

In the context above, when a plurality of reprogramming genes [e.g., 2 or more, preferably 2 or 3 different genes, selected from among Oct3/4, Sox2, Klf4, L-Myc, Lin28 (Lin28b), and SV40LT] are integrated in one expression vector, these genes can preferably be integrated into the expression vector via a sequence enabling polycistronic expression. By using a sequence enabling polycistronic expression, it is possible to more efficiently express a plurality of genes integrated in one expression vector. Useful sequences enabling polycistronic expression include, for example, the 2A sequence of foot-and-mouth disease virus (SEQ ID NO:63; PLoS ONE 3, e2532, 2008, Stem Cells 25, 1707, 2007), the IRES sequence (U.S. Pat. No. 4,937,190) and the like, with preference given to the 2A sequence. When a plurality of reprogramming genes are inserted into one expression vector as joined polycistronically, the order of the reprogramming genes is not particularly limited; for example, (i) Sox2 and Klf4, (ii) L-Myc and Lin28 (Lin28b), (iii) Klf4, Sox2 and Oct3/4 can be joined together in this order in the orientation from 5' to 3'.

An expression vector harboring a reprogramming gene can be introduced into a cell by a technique known per se according to the choice of the vector. In the case of a viral vector, for example, a plasmid containing the nucleic acid is introduced into an appropriate packaging cell (e.g., Plat-E cells) or a complementary cell line (e.g., 293-cells), the viral vector produced in the culture supernatant is recovered, and the vector is infected to a cell by a method suitable for the viral vector. For example, specific means using a retroviral vector are disclosed in WO2007/69666, *Cell,* 126, 663-676 (2006) and *Cell,* 131, 861-872 (2007). Specific means using a lentiviral vector is disclosed in *Science,* 318, 1917-1920 (2007). When iPS cells are utilized as cell sources for regenerative medicine, an expression (reactivation) of a reprogramming gene potentially increases the risk of carcinogenesis in tissues regenerated from differentiated cells derived from iPS cells; therefore, a reprogramming gene is preferably expressed transiently, without being integrated into the chromosome of the cells. From this viewpoint, use of an adenoviral vector, whose integration into chromosome is rare, is preferred. Specific means using an adenoviral vector is disclosed in *Science,* 322, 945-949 (2008). Because an adeno-associated viral vector is also low in the frequency of integration into chromosome, and is lower than adenoviral vectors in terms of cytotoxicity and inflammation-inducibility, it can be mentioned as another preferred vector. Because Sendai viral vector is capable of being stably present outside the chromosome, and can be degraded and removed using an siRNA as required, it is preferably utilized as well. Regarding a Sendai viral vector, one described in *J. Biol. Chem.,* 282, 27383-27391 (2007), *Proc. Jpn. Acad., Ser. B* 85, 348-362 (2009) or JP-B-3602058 can be used.

When a retroviral vector or a lentiviral vector is used, even if silencing of the transgene has occurred, it possibly becomes reactivated; therefore, for example, a method can be used preferably wherein a nucleic acid encoding a nuclear reprogramming substance is cut out using the Cre-loxP system, when becoming unnecessary. That is, with loxP sequences arranged on both ends of the nucleic acid in advance, iPS cells are induced, thereafter the Cre recombinase is allowed to act on the cells using a plasmid vector or adenoviral vector, and the region sandwiched by the loxP sequences can be cut out.

Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactivated (SIN) LTR prepared by deleting the sequence, or substituting the sequence with a polyadenylation sequence such as of SV40. Specific means using the Cre-loxP system and SIN LTR is disclosed in Chang et al., *Stem Cells*, 27: 1042-1049 (2009).

Meanwhile, being a non-viral vector, a plasmid vector can be transferred into a cell using the lipofection method, liposome method, electroporation method, calcium phosphate co-precipitation method, DEAE dextran method, microinjection method, gene gun method and the like. Specific means using a plasmid as a vector are described in, for example, *Science*, 322, 949-953 (2008) and the like.

When a plasmid vector, an adenovirus vector and the like are used, the transfection can be performed once or more optionally chosen times (e.g., once to 10 times, once to 5 times or the like). When two or more kinds of expression vectors are introduced into a somatic cell, it is preferable that these all kinds of expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre-loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transposase is allowed to act on the cell using a plasmid vector or adenoviral vector so as to completely eliminate the transgene from the chromosome. As examples of preferable transposons, piggyBac, a transposon derived from a lepidopterous insect, and the like can be mentioned. Specific means using the piggyBac transposon is disclosed in Kaji, K. et al., *Nature*, 458: 771-775 (2009), Woltjen et al., *Nature*, 458: 766-770 (2009).

Another preferable non-integration type vector is an episomal vector, which is capable of self-replication outside the chromosome. Specific means using an episomal vector is disclosed in Yu et al., *Science*, 324, 797-801 (2009). In a particularly preferred embodiment of the present invention, episomal vector having loxP sequences placed in the same orientation on the 5' and 3' sides of the vector constituent essential for the replication of the episomal vector can be used. Because an episomal vector is capable of self-replication outside the chromosome, it can ensure stable gene expression in the host cell even if it is not integrated in the genome. It is desirable, however, that the vector be quickly removed once the iPS cell is established. It is possible to make the episomal vector to lose its self-replicating potential by flanking a vector constituent essential for the replication of the episomal vector between two loxP sequences, and cutting out the vector constituent by the action of Cre recombinase, whereby the vector can be forced to be early shed from the iPS cell.

Examples of the episomal vector to be used in the present invention include a vector comprising as a vector component a sequence derived from EBV, SV40 and the like necessary for self-replication. The vector component necessary for self-replication is specifically exemplified by a replication origin and a gene that encodes a protein that binds to the replication origin to control the replication; examples include the replication origin oriP and the EBNA-1 gene for EBV, and the replication origin on and the SV40 large T antigen gene for SV40.

The episomal expression vector comprises a promoter that controls the transcription of reprogramming genes. The promoter used may be as described above. The episomal expression vector may further contain as desired an enhancer, a polyadenylation signal, a selection marker gene and the like, as described above. Examples of the selection marker gene include the dihydrofolate reductase gene, the neomycin resistance gene and the like.

The loxP sequences useful in the present invention include, in addition to the bacteriophage P1-derived wild type loxP sequence (SEQ ID NO:29), optionally chosen mutant loxP sequences capable of deleting the sequence flanked by the loxP sequence by recombination when placed in the same orientation at positions flanking a vector component necessary for the replication of the reprogramming gene. Examples of such mutant loxP sequences include lox71 (SEQ ID NO:30), mutated in 5' repeat, lox66 (SEQ ID NO:31), mutated in 3' repeat, and lox2272 and lox511, mutated in spacer portion. Although the two loxP sequences placed on the 5' and 3' sides of the vector component may be identical or not, the two mutant loxP sequences mutated in spacer portion must be identical (e.g., a pair of lox2272 sequences, a pair of lox511 sequences). Preference is given to a combination of a mutant loxP sequence mutated in 5' repeat (e.g., lox71) and a mutant loxP sequence mutated in 3' repeat (e.g., lox66). In this case, the loxP sequences remaining on the chromosome have double mutations in the repeats on the 5' side and 3' side as a result of recombination, and are therefore unlikely to be recognized by Cre recombinase, thus reducing the risk of causing a deletion mutation in the chromosome due to unwanted recombination. When the mutant loxP sequences lox71 and lox66 are used in combination, each may be placed on any of the 5' and 3' sides of the aforementioned vector component, but it is necessary that the mutant loxP sequences be inserted in an orientation such that the mutated sites would be located at the outer ends of the respective loxP sequences. Although a preferred episomal vector of the present invention is a self-removal vector early shedding from the cell even without being acted on by Cre recombinase, there are possibly exceptional cases where longer time is taken for the episomal vector to be shed from the cell. It is preferable, therefore, that the loxP sequences be designed in preparation for risks such as unwanted recombination due to Cre recombinase treatment.

Each of the two loxP sequences is placed in the same orientation on the 5' and 3' sides of a vector constituent essential for the replication of the reprogramming gene (i.e., a replication origin, or a gene sequence that encodes a protein that binds to the replication origin to control the replication). The vector constituent flanked by the loxP sequences may be either the replication origin or a gene sequence that encodes a protein that binds to a replication origin to control the replication, or both.

To increase RNA stability, the episomal vector or plasmid vector may, for example, have the woodchuck hepatitis virus posttranscriptional regulatory element (WPRE) sequence inserted between the reprogramming factor coding region and polyadenylation signal.

The episomal vector allows the vector to be introduced into the cell using, for example, the lipofection method, liposome method, electroporation method, calcium phosphate co-precipitation method, DEAE dextran method, microinjection method, gene gun method and the like. Specifically, for example, methods described in *Science,* 324: 797-801 (2009) and elsewhere can be used.

Whether or not the vector component necessary for the replication of the reprogramming gene has been removed from the iPS cell can be confirmed by performing a Southern blot analysis or PCR analysis using a nucleic acid comprising a nucleotide sequence in the vector component and/or in the vicinity of loxP sequence as a probe or primer, with the episome fraction isolated from the iPS cell as a template, and determining the presence or absence of a band or the length of the band detected. The episome fraction can be prepared by a method obvious in the art; for example, methods described in *Science,* 324: 797-801 (2009) and elsewhere can be used.

As stated in an Example below, some of the episomal vectors containing loxP sequences, provided by the present invention, exhibit not only the essential effect of any episomal vector wherein the exogenous nucleic acid factors (including reprogramming genes) that constitute the vector are not integrated, even transiently, in the genome of the cell, but also the unexpected effect wherein the vector in the form of an episome early shedding from the iPS cell, without being treated with Cre recombinase, when transferred to a somatic cell. Accordingly, the present invention also provides an self-removal episomal vector shedding from the cell early after offering a level of the expression of reprogramming factors sufficient to the establishment of an iPS cell. This vector is characterized in that it is shed from the iPS cell by the 5th passage at a frequency of 50% or more, preferably 60% or more, more preferably 70% or more. Alternatively, the self-removal episomal vector is characterized in that the number of copies per $1 \times 10^4$ cells within 1 week after the transfer is on the order of $10^6$ cells, whereas the vector is unstable in the cells to the extent that the number of copies per $1 \times 10^4$ cells at the time of establishment of iPS cell (e.g., about 4 week after vector transfer) decreases to 100 or less, preferably 50 or less, more preferably 30 or less.

Specifically, the early self-removal vector of the present invention has at least one, preferably two or more, more preferably three or more, particularly preferably all, of the following structural features (i) to (iv).
(i) Two loxP sequences are placed in the same orientation on the 5' and 3' sides of a vector constituent essential for the replication of the episomal vector (e.g., EBNA-1 gene and SV40 Large T antigen gene, preferably EBNA-1 gene).
(ii) The nucleic acid that encodes the reprogramming factor is under the control of CAG promoter.
(iii) The nucleic acid that encodes the reprogramming factor is under the control of rabbit β-globin polyadenylation signal.
(iv) The WPRE sequence is present between the nucleic acid that encodes the reprogramming factor and polyadenylation signal.

(D) Functional Inhibitors of p53

In the present invention, it is more preferable that in addition to the above-described nuclear reprogramming substances, a functional inhibitor of p53 be brought into contact with the starting cell. As mentioned herein, "an inhibitor of p53 function" may be any substance capable of inhibiting either (a) the function of the p53 protein or (b) the expression of the p53 gene. That is, not only substances that act directly on the p53 protein to inhibit the function thereof and substances that act directly on the p53 gene to inhibit the expression thereof, but also substances that act on a factor involved in p53 signal transduction to result in inhibition of the function of the p53 protein or the expression of the p53 gene, are also included in the scope of "an inhibitor of p53 function" as mentioned herein. Preferably, the functional inhibitor of p53 is a substance that inhibits the expression of the p53 gene, more preferably an expression vector that encodes an siRNA or shRNA against p53.

Examples of substances that inhibit the function of the p53 protein include, but are not limited to, a chemical inhibitor of p53, a dominant negative mutant of p53 or a nucleic acid that encodes the same, an anti-p53 antagonist antibody or a nucleic acid that encodes the same, a decoy nucleic acid comprising a consensus sequence of a p53-responsive element, a substance that inhibits the p53 pathway, and the like. Preferably, a chemical inhibitor of p53, a dominant negative mutant of p53 or a nucleic acid that encodes the same, and a p53 pathway inhibitor can be mentioned.

(D1) Chemical Inhibitors of p53

Examples of chemical inhibitors of p53 include, but are not limited to, p53 inhibitors typified by pifithrin (PFT)-α and -β, which are disclosed in WO 00/44364, PFT-μ disclosed in Storm et al. (*Nat. Chem. Biol.* 2, 474 (2006)), analogue thereof and salts thereof (for example, acid addition salts such as hydrochlorides and hydrobromides, and the like) and the like. Of these, PFT-α and analogues thereof [2-(2-Imino-4,5,6,7-tetrahydrobenzothiazol-3-yl)-1-p-tolylethanone, HBr (product name: Pifithrin-α) and 1-(4-Nitrophenyl)-2-(4,5,6,7-tetrahydro-2-imino-3(2H)-benzothiazolyl)ethanone, HBr (product name: Pifithrin-α, p-Nitro)], PFT-β and analogues thereof [2-(4-Methylphenyl)imidazo[2,1-b]-5,6,7,8-tetrahydrobenzothiazole, HBr (product name: Pifithrin-α, Cyclic) and 2-(4-Nitrophenyl)imidazo[2,1-b]-5,6,7,8-tetrahydrobenzothiazole (product name: Pifithrin-α, p-Nitro, Cyclic)], and PFT-μ [Phenylacetylenylsulfonamide (product name: Pifithrin-μ)] are commercially available from Merck.

Contact of a chemical inhibitor of p53 with a somatic cell can be performed by dissolving the inhibitor at an appropriate concentration in an aqueous or non-aqueous solvent, adding the solution of the inhibitor to a medium suitable for cultivation of somatic cells isolated from a human or mouse (for example, minimal essential medium (MEM), Dulbecco's modified Eagle medium (DMEM), RPMI1640 medium, 199 medium, F12 medium and the like supplemented with about 5 to 20% fetal bovine serum) so that the inhibitor concentration will fall in a range that fully inhibits the p53 function and does not cause cytotoxicity, and culturing the cells for a given period. The inhibitor concentration varies depending on the kind of inhibitor used, and is chosen as appropriate over the range of about 0.1 nM to about 100 nM. Duration of contact is not particularly limited, as far as it is sufficient to achieve nuclear reprogramming of the cells; usually, the inhibitor may be allowed to co-present in the medium until a positive colony emerges.

The p53 gene is known as a tumor suppressor gene; permanent inhibition of p53 function potentially increases the risk of carcinogenesis. Chemical inhibitors of p53 are useful, not only because of the advantage of permitting introduction into cells simply by the addition to the medium, but also because of the ability to terminate the inhibition of p53 function, easily and quickly, by removing the medium containing the inhibitor after induction of iPS cells.

(D2) Dominant Negative Mutants of p53

The choice of dominant negative mutant of p53 is not particularly limited, as far as the mutant is capable of competitively acting against the wild-type p53 protein endogenously expressed in somatic cells to inhibit the function thereof; for example, p53P275S, resulting from point mutation of the proline at the position 275 (in the case of humans, position 278) located in the DNA-binding region of mouse p53 to serine (de Vries, A., *Proc. Natl. Acad. Sci. USA*, 99, 2948-2953 (2002)); p53DD, resulting from deletion of the amino acids at the positions 14-301 of mouse p53 (in human p53, corresponds to the positions 11-304) (Bowman, T., *Genes Develop.,* 10, 826-835 (1996)), and the like can be mentioned. Other known mutants include, for example, p53S58A, resulting from point mutation of the serine at the position 58 of mouse p53 (in the case of humans, position 61) to alanine; p53C135Y, resulting from point mutation of the cysteine at the position 135 of human p53 (in the case of mice, position 132) to tyrosine; p53A135V, resulting from point mutation of the alanine at the position 135 of mouse p53 (in the case of humans, position 138) to valine; p53R172H, resulting from point mutation of the arginine at the position 172 (in the case of humans, position 175) to histidine; p53R270H, resulting from point mutation of the arginine at the position 270 (in the case of humans, position 273) to histidine; p53D278N, resulting from point mutation of the aspartic acid at the position 278 of mouse p53 (in the case of humans, position 281) to asparagine, and the like; these can be used in the same way.

A dominant negative mutant of p53 can be obtained by for example, the technique described below. First, an appropriate oligonucleotide is synthesized as a probe or primer on the basis of the mouse or human p53 cDNA sequence information shown by SEQ ID NO:1 or 3, and a mouse or human p53 cDNA is cloned from a mRNA, cDNA or cDNA library derived from a mouse or human cell or tissue, using the hybridization method or the (RT-)PCR method, and is subcloned into an appropriate plasmid. In a form wherein a codon of the site into which a mutation is to be introduced (for example, in the case of p53P275S, cct, which is shown by nucleotide numbers 951-953 in the nucleotide sequence shown by SEQ ID NO:1) is replaced with a codon that encodes another desired amino acid (for example, in the case of p53P275S, tct), a primer comprising the site is synthesized, and inverse PCR is performed using this primer with the plasmid incorporating the p53 cDNA as a template, whereby a nucleic acid that encodes the desired dominant negative mutant is acquired. In the case of a deletion mutant like p53DD, a primer may be designed outside the site to be deleted, and inverse PCR may be performed as described above. By introducing the thus-obtained nucleic acid that encodes the dominant negative mutant into a host cell, and recovering a recombinant protein from the cultured cell or its conditioned medium, the desired dominant negative mutant can be acquired.

Contact of a dominant negative mutant with a somatic cell can be achieved in the same manner as with the above-described proteinous nuclear reprogramming substances. As described above, permanent inhibition of p53 function potentially increases the risk of carcinogenesis. However, because a dominant negative mutant of p53 undergoes degradation by protease and disappears gradually in the transfected cell, and correspondingly the function of p53 endogenously expressed in the cell is restored, use of the mutant protein can be suitable in cases where high safety is required as in the utilization of iPS cells for therapeutic purposes.

(D3) Nucleic Acids that Encode Dominant Negative Mutants of p53

In another preferred mode of embodiment of the present invention, the inhibitor of p53 function is a nucleic acid that encodes a dominant negative mutant of p53. The nucleic acid may be a DNA or an RNA, or a DNA/RNA chimera, and is preferably a DNA. The nucleic acid may be double-stranded or single-stranded. A cDNA that encodes a dominant negative mutant of p53 can be cloned by the technique described above with respect to preparation of the mutant protein.

The cDNA thus isolated, like the aforementioned nucleic acids which are nuclear reprogramming substances (reprogramming genes), can be inserted into an appropriate expression vector and transferred to a somatic cell.

(D4) p53 Pathway Inhibitors

Here, the term p53 pathway is used with a meaning including all upstream signal cascades that can activate p53 and all downstream signal cascades mediated by activated p53. Therefore, p53 pathway inhibitors include all substances that inhibit any one of the aforementioned signal transduction pathways, but in a preferred mode of embodiment, the p53 pathway inhibitor is a substance that inhibits the expression or function (Myc inhibitory activity) of p21, whose transcription is activated by p53; for example, siRNA, shRNA, antisense nucleic acids, ribozymes against p21 and the like can be mentioned. These nucleic acids that inhibit the expression of p21 can be designed and synthesized in the same manner as the method for siRNA, shRNA, antisense nucleic acids, and ribozymes against p53 described below, and can be introduced into a somatic cell. The nucleic acids may be provided in the form of a vector that expresses them, the vector can be constructed in the same manner as the method for a vector that expresses an siRNA, shRNA, antisense nucleic acid, or ribozyme against p53 described below, and introduced into a somatic cell.

In another preferred mode of embodiment, the p53 pathway inhibitor is a substance that inhibits the ARF-MDM2-p53 pathway; for example, as ARF-MDM2-p53 pathway inhibitors, MDM2, which binds directly to p53 to promote the nuclear export or ubiquitination thereof or a nucleic acid that encodes the same, a substance that inhibits the expression or function of $p19^{ARF}$ or ATM (ataxia-telangiectasia mutated), which inhibits the action of MDM2 on p53, (for example, siRNAs and shRNAs against these factors) and the like can be mentioned.

(D5) Other Substances

As examples of other substances that inhibit the function of the p53 protein, anti-p53 antagonist antibody or a nucleic acid that encodes the same can be mentioned. The anti-p53 antagonist antibody may be a polyclonal antibody or a monoclonal antibody. The isotype of the antibody is not particularly limited, and is preferably IgG, IgM or IgA, particularly preferably IgG. The antibody may be, in addition to a complete antibody molecule, for example, a fragment such as Fab, Fab', or F(ab')$_2$, a conjugate molecule prepared by a gene engineering technique, such as scFv, scFv-Fc, minibody, or diabody, or a derivative thereof modified with a molecule having protein-stabilizing action, such as polyethylene glycol (PEG). An anti-p53 antagonist antibody can be produced using p53 or a partial peptide thereof as an antigen, by a method of antibody or anti-serum production known per se. As examples of known anti-p53 antagonist antibodies, PAb1801 (Oncogene Science Ab-2) and DO-1 (Oncogene Science Ab-6) (Gire and Wynford-Thomas, *Mol. Cell. Biol.,* 18, 1611-1621 (1998)) and the like can be mentioned. A nucleic acid that encodes an anti-p53 antagonist antibody can be isolated from a hybridoma that produces an anti-p53 monoclonal antibody by a conventional method. The H-chain and L-chain genes obtained may be joined together to prepare a nucleic acid that encodes a single-chain antibody.

As another substance that inhibits the function of the p53 protein, an anti-p21 antagonist antibody or a nucleic acid that encodes the same can be mentioned. An anti-p21 antagonist antibody and a nucleic acid that encodes the same can also be prepared as with the aforementioned anti-p53 antagonist antibody and nucleic acid that encodes the same.

Still another substance that inhibits the function of the p53 protein is a decoy nucleic acid comprising a consensus sequence of p53-responsive element (e.g., Pu-Pu-Pu-G-A/T-T/A-C-Py-Py-Py (Pu: purine base, Py: pyrimidine base); SEQ ID NO:27). Such a nucleic acid can be synthesized on the basis of the aforementioned nucleotide sequence information using an automated DNA/RNA synthesizer. Alternatively, such a decoy nucleic acid is commercially available (e.g., p53 transcription factor decoy (GeneDetect.com)).

An anti-p53 antagonist antibody and an anti-p21 antagonist antibody, or a nucleic acid that encodes the antibody can be introduced into a cell with the method described in the statement of a dominant negative mutant of p53 or a nucleic acid that encodes the mutant, respectively. The aforementioned decoy nucleic acid can be introduced into a cell by lipofection method and the like.

Meanwhile, as examples of substances that inhibit the expression of the p53 gene, siRNAs or shRNAs against p53, vectors that express an siRNA or shRNA against p53, antisense nucleic acids against p53 and ribozymes against p53, and the like can be mentioned, and siRNAs and shRNAs against p53 and vectors that express an siRNA or an shRNA are preferable.

(D6) siRNA and shRNA Against p53

An siRNA against p53 can be designed on the basis of the mouse or human p53 cDNA sequence information shown by SEQ ID NO:1 or 3, in accordance with, for example, the rules proposed by Elbashir et al. (*Genes Dev.*, 15, 188-200 (2001)). The target sequence for the siRNA is, as a general rule, AA+ $(N)_{19}$, but may be AA+ $(N)_{21}$ or NA+ $(N)_{21}$. The 5' end of the sense strand need not to be AA. Although the position of the target sequence is not particularly limited, it is desirable that the target sequence be selected from a region other than 5'-UTR, about 50 bases from the start codon, or 3'-UTR. The GC content of the target sequence is also not particularly limited, but the content is preferably about 30 to about 50%; a sequence with no irregularity in GC distribution and with only a few repeats is desirable. When a polIII promoter is used as a promoter in designing a vector that expresses an siRNA or shRNA of (b2) below, a sequence of 4 or more T or A bases in succession should not be chosen, so as to prevent polymerase transcription from ceasing.

The target sequence candidates selected on the basis of the above-described rules are examined for homology to sequences of 16-17 bases in succession in mRNAs other than the target, using a homology search software program such as BLAST (http://www.ncbi.nlm.nih.gov/BLAST/), so as to confirm the specificity of the target sequences selected. For the target sequences for which the specificity has been confirmed, a double-stranded RNA consisting of a sense strand having a 3'-terminal overhang of TT or UU in 19-21 bases after AA (or NA) and an antisense strand having a sequence complementary to the 19-21 bases and a 3'-terminal overhang of TT or UU, is designed as an siRNA. Also, an shRNA can be designed by choosing as appropriate an optionally chosen linker sequence capable of forming a loop structure (for example, about 8-25 bases), and ligating the aforementioned sense strand and antisense strand via the linker sequence.

Sequences of siRNAs and/or shRNAs can be searched for using search software programs available at no cost on various websites. Examples of such sites include, but are not limited to, the siRNA Target Finder (http://www.ambion.com/jp/techlib/misc/siRNA_finder.html) and insert design tool for pSilencer™ Expression Vector (http://www.ambion.com/jp/techlib/misc/psilencer_converter.htm 1), both provided by Ambion, and GeneSeer (http://codex.cshl.edu/scripts/newsearchhairpin.cgi), provided by RNAi Codex; and similar search is possible on the websites of QIAGEN, Takara Bio, SiSearch, Dharmacon, Whitehead Institute, Invitrogen, Promega and the like.

Shown below are the sequences of shRNAs against mouse p53 designed using software programs available on the websites of Ambion (SEQ ID NO:5-24) and RNAi Codex (SEQ ID NO:25 and 26). The underlined sequences are sense strands (5' side) and antisense strands (3' side) of dsRNAs resulting after cleavage with a dicer (not containing the 3'-overhang "TT"). Small letters indicate a mismatch or a loop.

[SEQ ID NO: 5]
5'-TTT<u>GACTGGATGACTGCCATGG</u>ttcaagaga<u>CCATGGCAGTCAT
CCAGTC</u>TTTTTT-3'

[SEQ ID NO: 6]
5'-TTT<u>GATATCCTGCCATCACCTC</u>ttcaagaga<u>GAGGTGATGGCAG
GATATC</u>TTTTTT-3'

[SEQ ID NO: 7]
5'-TTT<u>GGCCCAAGTGAAGCCCTCC</u>ttcaagaga<u>GGAGGGCTTCACT
TGGGCC</u>TTTTTT-3'

[SEQ ID NO: 8]
5'-TTT<u>GTGAAGCCCTCCGAGTGTC</u>ttcaagaga<u>GACACTCGGAGGG
CTTCAC</u>TTTTTT-3'

[SEQ ID NO: 9]
5'-TTT<u>GCCCTCCGAGTGTCAGGAG</u>ttcaagaga<u>CTCCTGACACTCG
GAGGGC</u>TTTTTT-3'

[SEQ ID NO: 10]
5'-TTT<u>GTCTGTTATGTGCACGTAC</u>ttcaagaga<u>GTACGTGCACATA
ACAGAC</u>TTTTTT-3'

[SEQ ID NO: 11]
5'-TTT<u>GTACTCTCCTCCCCTCAAT</u>ttcaagaga<u>ATTGAGGGGAGGA
GAGTAC</u>TTTTTT-3'

[SEQ ID NO: 12]
5'-TTT<u>GCTATTCTGCCAGCTGGCG</u>ttcaagaga<u>CGCCAGCTGGCAG
AATAGC</u>TTTTTT-3'

[SEQ ID NO: 13]
5'-TTT<u>GACGTGCCCTGTGCAGTTG</u>ttcaagaga<u>CAACTGCACAGGG
CACGTC</u>TTTTTT-3'

[SEQ ID NO: 14]
5'-TTT<u>GAAGTCACAGCACATGACG</u>ttcaagaga<u>CGTCATGTGCTGT
GACTTC</u>TTTTTT-3'

[SEQ ID NO: 15]
5'-TTT<u>GTCACAGCACATGACGGAG</u>ttcaagaga<u>CTCCGTCATGTGC
TGTGAC</u>TTTTTT-3'

[SEQ ID NO: 16]
5'-TTT<u>GGAAATTTGTATCCCGAGT</u>ttcaagaga<u>ACTCGGGATACAA
ATTTCC</u>TTTTTT-3'

[SEQ ID NO: 17]
5'-TTT<u>GTACATGTGTAATAGCTCC</u>ttcaagaga<u>GGAGCTATTACAC
ATGTAC</u>TTTTTT-3'

[SEQ ID NO: 18]
5'-TTT<u>GACTCCAGTGGGAACCTTC</u>ttcaagaga<u>GAAGGTTCCCACT
GGAGTC</u>TTTTTT-3'

[SEQ ID NO: 19]
5'-TTT<u>GTCCTTTGCCCTGAACTGC</u>ttcaagaga<u>GCAGTTCAGGGCA
AAGGAC</u>TTTTTT-3'

[SEQ ID NO: 20]
5'-TTT<u>GATCCGCGGGCGTAAACGC</u>ttcaagaga<u>GCGTTTACGCCCG
CGGATC</u>TTTTTT-3'

-continued

[SEQ ID NO: 21]
5'-TTTGACCAAGAAGGGCCAGTCTttcaagagaAGACTGGCCCTTC
TTGGTCTTTTTT-3'

[SEQ ID NO: 22]
5'-TTTGAAAGTGGGGCCTGACTCAttcaagagaTGAGTCAGGCCCC
ACTTTCTTTTTT-3'

[SEQ ID NO: 23]
5'-TTTGTTGGGGAATAGGTTGATAttcaagagaTATCAACCTATTC
CCCAACTTTTTT-3'

[SEQ ID NO: 24]
5'-TTTGATTCTATCTTGGGCCCTCttcaagagaGAGGGCCCAAGAT
AGAATCTTTTTT-3'

[SEQ ID NO: 25]
5'-TTTGCAuTACAgGTACgTGTGTAgtgtgctgtccTACACATGTA
CTTGTAGTGTTTTTT-3'

[SEQ ID NO: 26]
5'-TTTGCAGTuTACTTuCCGCCgTAgtgtgctgtccTATGGCGGGA
AGTAGACTGTTTTTT-3'

An siRNA against p53 can be prepared by synthesizing a sense strand oligonucleotide and antisense strand oligonucleotide designed as described above using an automated DNA/RNA synthesizer separately, and, for example, denaturing the oligonucleotides in an appropriate annealing buffer solution at about 90 to about 95° C. for about 1 minute, thereafter annealing the same at about 30 to about 70° C. for about 1 to about 8 hours. An shRNA against p53 can be prepared by synthesizing oligonucleotides having an shRNA sequence, designed as described above, using an automated DNA/RNA synthesizer, and allowing the same to self-anneal as described above.

Although the nucleotide molecules that constitute the siRNA and shRNA may be naturally occurring RNAs, the molecules can comprise various chemical modifications in order to increase the stability (chemical and/or against enzyme) or specific activity (affinity for mRNA). For example, to prevent degradation by hydrolases such as nuclease, the phosphoric acid residue (phosphate) of each nucleotide that constitutes the siRNA or shRNA can be substituted with, for example, a chemically modified phosphoric acid residue such as phosphorothioate (PS), methylphosphonate, or phosphorodithionate. The hydroxyl group at the 2'-position of the sugar (ribose) of each nucleotide may be replaced with —OR (R represents, for example, $CH_3(2'-O-Me)$, $CH_2CH_2OCH_3(2'-O-MOE)$, $CH_2CH_2NHC(NH)NH_2$, $CH_2CONHCH_3$, $CH_2CH_2CN$ or the like). Furthermore, a base moiety (pyrimidine, purine) may be chemically modified; for example, introduction of a methyl group or a cationic functional group into the 5-position of the pyrimidine base, substitution of the 2-position carbonyl group with thiocarbonyl and the like can be mentioned.

Regarding the conformation of the sugar moiety of RNA, two types are dominant: C2'-endo (S type) and C3'-endo (N type); in a single-stranded RNA, the sugar moiety occurs in an equilibrium of both, but when a double strand is formed, the conformation is fixed at the N type. Therefore, BNA (LNA) (Imanishi, T. et al., *Chem. Commun.*, 1653-9, 2002; Jepsen, J. S. et al., *Oligonucleotides*, 14, 130-46, 2004) and ENA (Morita, K. et al., *Nucleosides Nucleotides Nucleic Acids*, 22, 1619-21, 2003), which are RNA derivatives wherein the conformation of the sugar moiety is fixed at the N type by bridging the 2' oxygen and 4' carbon so as to confer strong bindability to the target RNA, can also be used preferably.

However, because replacing all ribonucleoside molecules in a naturally occurring RNA with modified type molecules can lead to the loss of RNAi activity, it is necessary to introduce a modified nucleoside to the minimum possible extent that allows the RISC complex to function.

An siRNA against p53 can also be purchased from, for example, Ambion (e.g., Ambion Cat#AM16708, an siRNA ID#69659, 69753, 69843, 187424, 187425, 187426), Santa Cruz (e.g., Santa Cruz Cat#sc-29436, 44219) and the like.

An siRNA and shRNA against human p53 can also be designed and synthesized using one of the aforementioned search software programs, by inputting the sequence of human p53 cDNA shown by SEQ ID NO:3 or Refseq. No. (NM_000546) and the like as a query, or can also be purchased from Ambion and the like. Specifically, an shRNA against human p53 having the sequence 5'-GACTCCAGTGGTAATCTACTGctcgagCAGTAGATT-ACCACTGGAGTC-3' (SEQ ID NO: 28; underlined portion indicates the target sequence for p53; the capital letters indicate the portions where a dsRNA is formed), the shRNA against p53 described in *Science*, 296, 550-553 (2002), and the like can be mentioned.

Contact of an siRNA or shRNA against p53 with a somatic cell can be achieved by, as in the case of plasmid DNA, introducing the nucleic acid into the cell using the liposome method, polyamine method, electroporation method, beads method and the like. The method using a cationic liposome is the most common and offers high transfer efficiency. In addition to common transfection reagents such as Lipofectamine2000 and Oligofectamine (Invitrogen), for example, transfer reagents suitable for introduction of an siRNA, such as the GeneEraser™ siRNA transfection reagent (Stratagene), are also commercially available.

(D7) Vectors that Express an siRNA or shRNA Against p53

Vectors that express an siRNA are available in the tandem type and the stem loop (hairpin) type. The former is the type in which an expression cassette for a sense strand of an siRNA and an expression cassette for an antisense strand are ligated tandem, each strand being expressed in the cell and undergoing annealing to form a double-stranded siRNA (dsRNA). Meanwhile, the latter is the type in which an expression cassette for an shRNA is inserted into a vector, the shRNA being expressed in the cell and undergoing processing by a dicer to form a dsRNA. Although a polII promoter (for example, immediate-early promoter of CMV) may be used as the promoter, it is common practice to use a polIII promoter in order to allow the accurate transcription of short RNA. As the polIII promoter, mouse and human U6-snRNA promoters, human H1-RNase P RNA promoter, human valine-tRNA promoter and the like can be mentioned. As a transcription termination signal, a sequence of 4 or more T residues in succession is used.

The siRNA or shRNA expression cassette thus constructed is then inserted into a plasmid vector or a viral vector. Such vectors that can preferably be utilized are the same as those mentioned above in relation to nucleic acids which are nuclear reprogramming substances (reprogramming genes) (viral vectors such as retrovirus, lentivirus, adenovirus, adeno-associated virus, herpesvirus, and Sendai virus; animal cell expression plasmids; episomal vectors and the like). A vector, like reprogramming genes, can be chosen as appropriate according to the intended use of the iPS cell obtained. The p53 gene is known as a cancer suppression gene, and permanent functional inhibition of p53 potentially increases the risk of carcinogenesis. Therefore, bearing in mind a medical application of the iPS cell generated, it is desirable that the siRNA or shRNA against p53 be designed to be transiently expressed in the cell. For this reason, greater preference is given to plasmid vectors and the like that are incapable of self-replication for use as vectors to harbor a nucleic acid that encodes the siRNA or shRNA against p53. When combined with reprogramming factors of the present invention, the siRNA or shRNA against p53 gives a sufficient iPS cell establishment efficiency even in transient expression from the plasmid.

Alternatively, as an expression vector that encodes the shRNA against p53, a viral vector of retrovirus or the like, a plasmid vector, an episomal vector and the like, prepared on the basis of a commercially available plasmid (for example, pMKO.1-puro p53 shRNA2: #10672, commercially available from Addgene, and the like) or the like can also be used. The aforementioned Cre-loxP system or piggyBac transposon system can also be utilized as required.

Contact of a vector that expresses the siRNA or shRNA against p53 with a somatic cell is achieved by introducing a plasmid vector, episomal vector or viral vector prepared as described above into the cell. These transfections can be achieved by the same techniques as those described above with respect to reprogramming genes.

(D8) Other Substances

As other substances that inhibit the expression of the p53 gene, antisense nucleic acids and ribozymes against p53 can be mentioned.

The antisense nucleic acid may be a DNA or an RNA, or a DNA/RNA chimera. When the antisense nucleic acid is a DNA, an RNA:DNA hybrid formed by a target RNA and the antisense DNA is capable of being recognized by endogenous RNase H to cause selective degradation of the target RNA. Therefore, in the case of an antisense DNA that directs the degradation by RNase H, the target sequence may be not only a sequence in p53 mRNA, but also a sequence in the intron region of the primary transcript of the p53 gene. The length of the target region for the antisense nucleic acid is not particularly limited, as far as hybridization of the antisense nucleic acid results in an inhibition of the translation into the p53 protein; the target region may be the entire sequence or a partial sequence of p53 mRNA, and may be a sequence of about 15 bases for the shortest, or of the entire sequence of the mRNA or primary transcript for the longest. Considering the ease of synthesis, antigenicity, transferability in cells and other issues, an oligonucleotide consisting of about 15 to about 40 bases, particularly about 18 to about 30 bases, is preferable. Positions of the target sequence include, but are not limited to, 5'- and 3'-UTR, vicinities of the start codon and the like.

A ribozyme refers to an RNA possessing an enzyme activity to cleave a nucleic acid in the narrow sense, and is herein understood to be used as a concept encompassing a DNA, as far as it possesses sequence-specific nucleic acid cleavage activity. One of the most versatile ribozymes is a self-splicing RNA found in infectious RNAs such as viroid and virusoid, and the hammerhead type, the hairpin type and the like are known. The hammerhead type exhibits enzyme activity with about 40 bases in length, and it is possible to specifically cleave the target mRNA by making several bases at both ends adjoining to the hammerhead structure portion (about 10 bases in total) be a sequence complementary to the desired cleavage site of the mRNA.

An antisense nucleic acid or a ribozyme can be synthesized using an automated DNA/RNA synthesizer. The nucleotide molecules that constitute them may also have the same modifications as those described above for siRNA, so as to increase the stability, specific activity and the like.

Alternatively, the antisense nucleic acid or ribozyme can also be used in the form of a nucleic acid that encodes the same, as in the case of siRNA.

An inhibitor of p53 function needs to be brought into contact with a somatic cell in a way sufficient to inhibit the p53 function in the step of somatic cell nuclear reprogramming. As far as this requirement is met, the nuclear reprogramming substance and the inhibitor of p53 function may be brought into contact with the somatic cell simultaneously, or either one may be brought into contact in advance. In a mode of embodiment, for example, when the nuclear reprogramming substance is a nucleic acid that encodes a proteinous factor, and the inhibitor of p53 function is a chemical inhibitor, the former involves a given length of time lag from the transfection treatment to the mass-expression of the proteinous factor, whereas the latter is capable of rapidly inhibiting the p53 function, so that after the cell is cultured for a given length of time after the transfection treatment, the chemical inhibitor of p53 can be added to the medium. In another mode of embodiment, for example, when the nuclear reprogramming substance and the inhibitor of p53 function are used in the form of viral vectors, plasmid vectors, episomal vectors and the like, both may be simultaneously introduced into the cell.

(E) iPS Cell Establishment Efficiency Improvers

By bringing, in addition to an inhibitor of p53 function, another publicly known iPS cell establishment efficiency improver, into contact with a somatic cell, a further increase in the iPS cell establishment efficiency is expected. Examples of iPS cell establishment efficiency improvers include, but are not limited to, histone deacetylase (HDAC) inhibitors [e.g., valproic acid (VPA) (*Nat. Biotechnol.*, 26 (7): 795-797 (2008)), low-molecular inhibitors such as trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], G9a histone methyltransferase inhibitors [e.g., low-molecular inhibitors such as BIX-01294 (*Cell Stem Cell*, 2: 525-528 (2008)), nucleic acid-based expression inhibitors such as siRNAs and shRNAs against G9a (e.g., G9a siRNA (human) (Santa Cruz Biotechnology) and the like) and the like], L-calcium channel agonists (e.g., Bayk8644) (Cell Stem Cell, 3, 568-574 (2008)), UTF1 (Cell Stem Cell, 3, 475-479 (2008)), modifiers of intracellular signal transfection [e.g., Wnt Signaling activators (e.g., soluble Wnt3a) (Cell Stem Cell, 3, 132-135 (2008)), TGF-β inhibitors, MEK inhibitors, 2i/LIF (2i is an inhibitor of mitogen-activated protein kinase signalling and glycogen synthase kinase-3, PloS Biology, 6 (10), 2237-2247 (2008))], other natural or synthetic low-molecular compounds (e.g., 5'-azacytidine, thiazovivin, vitamin C and the like), and ES cell-specific miRNAs [e.g., miR-302-367 cluster (Mol. Cell. Biol. doi: 10.1128/MCB.00398-08, WO2009/075119), miR-302 (RNA (2008) 14: 1-10), miR-291-3p, miR-294 and miR-295 (Nat. Biotechnol. 27: 459-461 (2009))]. As mentioned above, the nucleic acid-based expression inhibitors may be in the form of expression vectors harboring a DNA that encodes the siRNA or shRNA.

Of the aforementioned constituents of nuclear reprogramming substances, SV40 large T, for example, can also be included in the scope of iPS cell establishment efficiency improvers because they are auxiliary factors unessential for the nuclear reprogramming of somatic cells. While the is mechanism of nuclear reprogramming remains unclear, it does not matter whether auxiliary factors, other than the factors essential for nuclear reprogramming, are deemed nuclear reprogramming substances or iPS cell establishment efficiency improvers. Hence, because the somatic cell nuclear reprogramming process is taken as an overall event resulting from contact of nuclear reprogramming substances and an iPS cell establishment efficiency improver with somatic cells, it does not seem always essential for those skilled in the art to distinguish between the two.

Contact of these other iPS cell establishment efficiency improvers with somatic cells can be achieved as described above with respect to functional inhibitors of p53, corresponding to the case where the improver is (a) a proteinous factor, (b) a nucleic acid that encodes the proteinous factor, or (c) a low-molecular compound, respectively.

The other iPS cell establishment efficiency improver may be contacted with the somatic cell simultaneously with the nuclear reprogramming substance, and either one may be contacted in advance, as far as the efficiency of iPS cell establishment from a somatic cell improves significantly compared with the efficiency obtained in the absence of the substance; according to the properties of the substance, the substance can be brought into contact with the somatic cell at the same timing as that described above in relation to a functional inhibitor of p53.

(F) Improving the Establishment Efficiency by Culture Conditions iPS cell establishment efficiency can further be improved by culturing the cells under hypoxic conditions in the nuclear reprogramming process for somatic cells. As mentioned herein, the term "hypoxic conditions" means that the ambient oxygen concentration as of the time of cell culture is significantly lower than that in the atmosphere. Specifically, conditions involving lower oxygen concentrations than the ambient oxygen concentrations in the 5-10% $CO_2$/95-90% air atmosphere, which is commonly used for ordinary cell culture, can be mentioned; examples include conditions involving an ambient oxygen concentration of 18% or less. Preferably, the ambient oxygen concentration is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The ambient oxygen concentration is preferably 0.1% or more (e.g., 0.2% or more, 0.3% or more, 0.4% or more and the like), 0.5% or more (e.g., 0.6% or more, 0.7% or more, 0.8% or more, 0.95% or more and the like), or 1% or more (e.g., 1.1% or more, 1.2% or more, 1.3% or more, 1.4% or more and the like).

Although any method of creating a hypoxic state in a cellular environment can be used, the easiest way is to culture cells in a $CO_2$ incubator permitting adjustments of oxygen concentration, and this represents a suitable case. $CO_2$ incubators permitting adjustment of oxygen concentration are commercially available from various manufacturers (e.g., $CO_2$ incubators for hypoxic culture manufactured by Thermo scientific, Ikemoto Scientific Technology, Juji Field, Wakenyaku etc.).

The time of starting cell culture under hypoxic conditions is not particularly limited, as far as iPS cell establishment efficiency is not prevented from being improved compared with the normal oxygen concentration (20%). Although the culture may be started before the somatic cell is contacted with the nuclear reprogramming substance, or at the same time as the contact, or after the contact, it is preferable, for example, that the culture under hypoxic conditions be started just after the somatic cell is contacted with the nuclear reprogramming substance, or at a given time interval after the contact [e.g., 1 to 10 (e.g., 2, 3, 4, 5, 6, 7, 8 or 9) days].

The duration of cultivation of cells under hypoxic conditions is not particularly limited, as far as iPS cell establishment efficiency is not prevented from being improved compared with the normal oxygen concentration (20%); examples include, but are not limited to, periods of 3 days or more, 5 days or more, for 7 days or more or 10 days or more, and 50 days or less, 40 days or less, 35 days or less or 30 days or less and the like. Preferred duration of cultivation under hypoxic conditions varies depending on ambient oxygen concentration; those skilled in the art can adjust as appropriate the duration of cultivation according to the oxygen concentration used. In an embodiment of the present invention, if iPS cell candidate colonies are selected with drug resistance as an index, it is preferable that a normal oxygen concentration be restored from hypoxic conditions before starting drug selection.

Furthermore, preferred starting time and preferred duration of cultivation for cell culture under hypoxic conditions also vary depending on the choice of nuclear reprogramming substance used, iPS cell establishment efficiency at normal oxygen concentrations and the like.

After being contacted with nuclear reprogramming substances and a functional inhibitor of p53 (and another iPS cell establishment efficiency improver if required), the cell can, for example, be cultured under conditions suitable for culturing ES cells. In the case of mouse cells, the culture is carried out with the addition of Leukemia Inhibitory Factor (LIF) as a differentiation suppression factor to an ordinary medium. Meanwhile, in the case of human cells, it is desirable that basic fibroblast growth factor (bFGF) and/or stem cell factor (SCF) be added in place of LIF. Usually, the cell is cultured in the co-presence of mouse embryonic fibroblasts treated with radiation or an antibiotic to terminate the cell division, as feeder cells. Mouse embryonic fibroblasts in common use as feeders include the STO cell line (ATCC CRL-1503) and the like; for induction of an iPS cell, the SNL cell generated by stably integrating the neomycin resistance gene and the LIF gene in the STO cell (SNL76/7 STO cell; ECACC 07032801) [McMahon, A. P. & Bradley, A. Cell 62, 1073-1085 (1990)] and the like are commonly used. However, in the present invention, it is more preferable to use a mouse embryonic primary fibroblast (MEF) because its use offers a further improvement of human iPS cell establishment efficiency. Mitomycin C-treated MEFs are commercially available from Millipore and ReproCELL. Co-culture with these feeder cells may be started before contact of the nuclear reprogramming substance, at the time of the contact, or after the contact (for example, 1-10 days later).

The present inventors succeeded in providing for the first time a method of generating a human iPS cell using nuclear reprogramming substances of the present invention and a functional inhibitor of p53 in combination with a non-viral vector, preferably an episomal vector, especially of the early self-removal type, wherein no ingredient from a non-human animal is used (i.e., under completely xeno-free conditions) in the cultivation from the transfer of the nuclear reprogramming substances and functional inhibitor of p53 to the somatic cell to the establishment and maintenance of an iPS cell. To induce a human iPS cell under xeno-free conditions, the starting cell is cultured in a medium free of FCS and other ingredients from non-human animals after being brought into contact with nuclear reprogramming substances and a functional inhibitor of p53 (and another iPS cell establishment efficiency improver if required). Useful substances to be added as differentiation suppression factors to the medium (e.g., bFGF, SCF and the like) are in the form of a purified human protein, preferably a recombinant protein. Optionally chosen human somatic cells can be used as feeder cells; examples of preferred feeder cells include human dermal fibroblasts (HDFs), human dental pulp stem cells and the like. It is also possible to induce a human iPS cell without using feeder cells. In this case, a commercially available xeno-free coating agent may be used to coat the cell container in place of Matrigel and gelatin.

A candidate colony of iPS cells can be selected by a method with drug resistance and reporter activity as indicators, and also by a method based on macroscopic examination of morphology. As an example of the former, a colony positive for drug resistance and/or reporter activity is selected using a recombinant cell wherein a drug resistance gene and/or a reporter gene is targeted to the locus of a gene highly expressed specifically in pluripotent cells (for example, Fbx15, Nanog, Oct3/4 and the like, preferably Nanog or Oct3/4). As examples of such recombinant cells, a mouse-derived MEF wherein the βgeo (which encodes a fusion protein of β-galactosidase and neomycin phosphotransferase) gene is knocked-in to the Fbx15 gene locus (Takahashi & Yamanaka, Cell, 126, 663-676 (2006)), or a transgenic mouse-derived MEF wherein green fluorescent protein (GFP) gene and the puromycin resistance gene are integrated in the Nanog gene locus (Okita et al., Nature, 448, 313-317 (2007)) and the like can be mentioned. Meanwhile, methods for selecting a candidate colony by macroscopic examination of morphology include, for example, the method described by Takahashi et al. in Cell, 131, 861-872 (2007). Although methods using reporter cells are convenient and efficient, colony selection by macroscopic examination is desirable from the viewpoint of safety when iPS cells are prepared for the purpose of human treatment.

The identity of the cells of the selected colony as iPS cells can be confirmed by positive responses to Nanog (or Oct3/4) reporters (puromycin resistance, GFP positivity and the like), as well as by the formation of a visible ES cell-like colony, as described above; however, to increase the accuracy, it is possible to perform tests such as alkaline phosphatase staining, analyzing the expression of various ES-cell-specific genes, and transplanting the cells selected to a mouse and confirming teratoma formation.

The iPS cells thus established can be used for various purposes. For example, by utilizing a method of differentiation induction reported with respect to ES cells, differentiation into various cells (e.g., myocardial cells, blood cells, nerve cells, vascular endothelial cells, insulin-secreting cells and the like) from iPS cells can be induced. Therefore, inducing iPS cells using a somatic cell collected from a patient or another person of the same or substantially the same HLA type would enable stem cell therapy by autogeneic or allogeneic transplantation, wherein the iPS cells are differentiated into desired cells (that is, cells of an affected organ of the patient, cells that have a therapeutic effect on disease, and the like), which are transplanted to the patient. Furthermore, because functional cells (e.g., hepatocytes) differentiated from iPS cells are thought to better reflect the actual state of the functional cells in vivo than do corresponding existing cell lines, they can also be suitably used for in vitro screening for the effectiveness and toxicity of pharmaceutical candidate compounds and the like.

The present invention is hereinafter described in further detail by means of the following examples, to which, however, the invention is never limited.

EXAMPLES

Example 1

Establishment of Human iPS Cells Using Retroviruses

Retroviruses for reprogramming were prepared on the basis m of the pMXs plasmid and Plat-E packaging cells [supplied by Dr. Toshio Kitamura at the University of Tokyo; Morita, S. et al., Gene Ther. 7, 1063-1066 (2000)]. Various constructs were inserted into the multicloning site of pMXs to yield retroviral vectors to be used for reprogramming. The constructs inserted were prepared by joining human Oct3/4 (O in FIG. 1), human Sox2 (S in FIG. 1), human Klf4 (K in FIG. 1), human c-Myc (M in FIG. 1), human Lin28 (L in FIG. 1), human Nanog (N in FIG. 1), and human L-Myc (U in FIG. 1), and the translated region of each gene via the 2A sequence of foot-and-mouth disease virus [in FIG. 1, symbols for respective genes (shown above) are hyphenated (e.g., O-M-L)]. GFP was used as a negative control.

Each retrovirus for reprogramming was prepared by transferring each of the aforementioned retroviral vectors to Plat-E cells that had been seeded to a 6-well culture plate (Falcon) at $0.6 \times 10^6$ cells per well on the day before. The cells were cultured at 37° C. in the presence of 5% $CO_2$ using DMEM/10% FCS [a culture broth prepared by adding 10% fetal calf serum to DMEM (Nacalai Tesque)]. To facilitate vector transfer, 4.5 μL of FuGene6 transfection reagent (Roche) was placed in 100 μL of Opti-MEM I Reduced-Serum Medium (Invitrogen), and the cells were allowed to stand at room temperature for 5 minutes. Subsequently, 1.5 μg of each expression vector was added, and the cells were allowed to further stand at room temperature for 15 minutes, after which they were added to the Plat-E culture broth. On day 2, the Plat-E supernatant was replaced with a fresh supply of the medium. On day 3, the culture supernatant was recovered and filtered through a 0.45 μm sterile filter (Whatman), and polybrene (Nacalai) was added at 4 μg/mL to yield a viral liquid.

In the experiments, a fibroblast established from a skin from a neonatal Caucasian (Cell Applications) was used after being transfected with mouse Slc7a1 by means of lentivirus. This fibroblast was cultured and maintained at 37° C. in the presence of 5% $CO_2$ in a 100 mm culture dish using DMEM/10% FCS as a culture broth. On the day before transferring reprogramming factors, the medium was removed, and the cells were washed by the addition of 5 mL of PBS. After removing the PBS, 0.25% Trypsin/1 mM EDTA (Invitrogen) was added, and a reaction was carried out at 37° C. for about 5 minutes. After the cells rose, DMEM/10% FCS was added to suspend the cells, and $1.3 \times 10^5$ cells were seeded to one well of a 6-well culture plate (Falcon).

Figure 2:
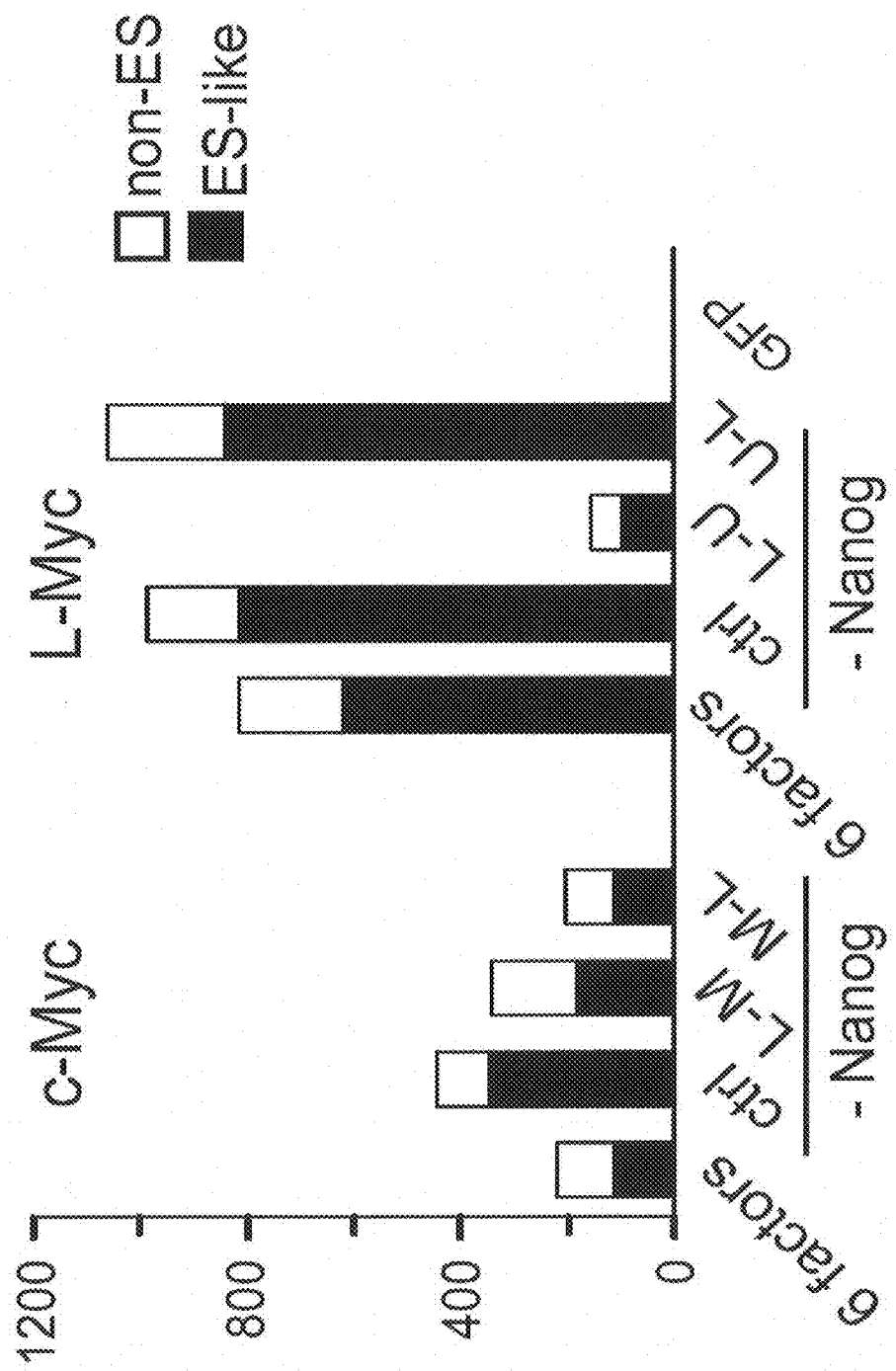
FIG. 2 is a graphic representation of some of the results shown in FIG. 1. The number of ES-like colonies is indicated by a solid bar, and the number of non-ES-like colonies by an outlined bar.

The following day, the cells were mixed and infected with each retrovirus that had been produced using Plat-E cells. 24 hours later, the medium was replaced with a fresh supply to terminate the infection. On day 6 after the start of the infection, the medium was removed from the plate, and the cells were washed by the addition of 1 mL of PBS. After removing the PBS, 0.25% Trypsin/1 mM EDTA (Invitrogen) was added, and a reaction was carried out at 37° C. for about 5 minutes. After the cells rose, DMEM/10% FCS was added to suspend the cells, and $5 \times 10^5$ cells were seeded to a 100 mm dish containing previously seeded feeder cells. The feeder cells used were SNL cells that had been treated with mitomycin C to terminate cell division. The following day, the medium was replaced with a primate ES cell culture medium (ReproCELL) supplemented with 4 ng/mL bFGF (Wako); this medium exchange was continued every 2 days. On day 35, human ES cell-like colonies were counted. Photographs of colonies and colony counts are shown in FIG. 1. The results of colony counting are summarized in FIG. 2. In all combinations of genes, the establishment efficiency for human iPS colonies (ES-like colonies) was much higher with the use of L-Myc in place of c-Myc. Whether c-Myc or L-Myc was used, the establishment efficiency was higher with the use of 5 genes excluding Nanog (Oct3/4, Sox2, Klf4, Lin28, and c-Myc or L-Myc; ctrl in FIG. 2) than with the use of 6 genes including Nanog ("6 factors" in FIG. 2). When L-Myc was used as joined in the order of L-Myc-Lin28 (U-L in FIG. 2), the establishment efficiency did not decrease compared with the level obtained when L-Myc was used but not joined (5 genes transferred separately: "ctrl" in FIG. 2).

Example 2

Establishment of Human iPS Cells Using Episomal Plasmids (1)

A plasmid for reprogramming was prepared on the basis of pCX-EGFP (supplied by Dr. Masaru Okabe at Osaka University; FEBS Letters, 407, 313-319, 1997). First, the woodchuck hepatitis virus posttranscriptional regulatory element (WPRE) sequence was inserted downstream of EGFP. A cassette for replicating this vector in the cell was prepared by inserting a loxP sequence into both ends of the EBNA-1 of pCEP4 (Invitrogen). This cassette containing the EBNA-1 and oriP was integrated into the BamHI site of the aforementioned pCX-EGFP incorporating the WPRE, and this was named pCXLE-EGFP. This pCXLE-EGFP was treated with EcoRI, and various constructs, in place of EGFP, were inserted to yield plasmids for reprogramming. The five constructs inserted were: 1) human Oct3/4, 2) a construct prepared by joining the translated regions of human Sox2 and human Klf4 via the 2A sequence of foot-and-mouth disease virus, 3) a construct prepared by joining the translated regions of human Klf4, human Sox2 and human Oct3/4 via the 2A sequence of foot-and-mouth disease virus, 4) a construct prepared by joining the translated regions of human c-Myc, human Lin28 and Nanog via the 2A sequence of foot-and-mouth disease virus, and 5) SV40 Large T antigen (each construct is under the control of the CAG promoter and rabbit β-globin polyA sequence), which were designated as pCXLE-hOct4, pCXLE-hSK, pCXLE-hKSO, pCXLE-hMLN, and pCX-SV40LT, respectively (pCX-SV40LT is a plasmid having none of the WPRE sequence, EBNA-1 cassette and loxP sequence).

Figure 3:
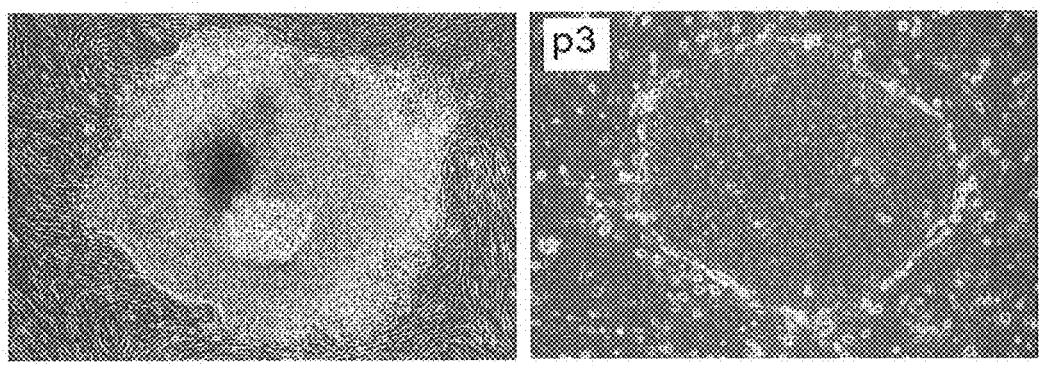
FIG. 3 is a photographic representation of colonies of an iPS cell established by transferring the five different plasmids pCXLE-hOct4, pCXLE-hSK, pCXLE-hKSO, pCXLE-hMLN, and pCX-SV40LT to adult human dermal fibroblasts. The left plate shows a photograph as of the time of iPS cell establishment; the right plate shows a photograph as of the 3rd passage (p3).

In the experiments, a fibroblast established from a facial skin from a 36-year-old Caucasian female (Cell Applications, Lot1388) was used. This fibroblast was cultured and maintained at 37° C. in the presence of 5% $CO_2$ in a 100 mm culture dish using DMEM/10% FCS [a culture broth prepared by adding 10% fetal bovine serum to DMEM (Nacalai Tesque)]. At the time of plasmid transfer, the medium was removed, and the cells were washed by the addition of 5 mL of PBS. After removing the PBS, 0.25% Trypsin/1 mM EDTA (Invitrogen) was added, and a reaction was carried out at 37° C. for about 5 minutes. After the cells rose, DMEM/10% FCS was added to suspend the cells, and $6×10^5$ cells were recovered in a 15 mL centrifugal tube. The suspension was centrifuged at 800 rpm for 5 minutes, and the supernatant was removed. A total of 3 μg of plasmids (0.5 μg pCXLE-hOct4, 1 μg pCXLE-hSK, 0.5 μg pCXLE-hKSO, 0.5 μg pCXLE-hMLN, 0.5 μg pCX-SV40LT) was transferred to the cells using Microporator (AR BROWN). This transfer took place using a 100 μL chip with three pulses at 1650 V for 10 ms. The transfected cells were transferred to a 6-well culture plate (Falcon) containing 3 mL of DMEM/10% FCS, and cultured at 37° C. in the presence of 5% $CO_2$ for 6 days. Subsequently, the medium was removed, and the cells were washed by the addition of 2 mL of PBS. After removing the PBS, 0.25% Trypsin/1 mM EDTA (Invitrogen) was added, and a reaction was carried out at 37° C. for about 5 minutes. After the cells rose, DMEM/10% FCS was added to suspend the cells, and $2×10^5$ cells were seeded to a 100 mm dish containing previously seeded feeder cells. The feeder cells used were mitomycin C-treated MEF. The following day, the medium was replaced with a primate ES cell culture medium (ReproCELL) supplemented with 4 ng/mL bFGF (Wako); this medium exchange was continued every 2 days. On day 26, one human ES cell-like colony emerged. A photograph of the colony as of the time of establishment is shown in FIG. 3 (left). A photograph of the colony at the 3rd passage is shown in FIG. 3 (right). One ES-like colony could be established from $2×10^5$ cells.

Example 3

Establishment of Human iPS Cells Using Episomal Plasmids (2)

Four different plasmids, other than pCX-SV40LT, which was used in Example 2, were used for reprogramming: pCXLE-hOct4, pCXLE-hSK, pCXLE-hKSO, and pCXLE-hMLN.

Figure 4:
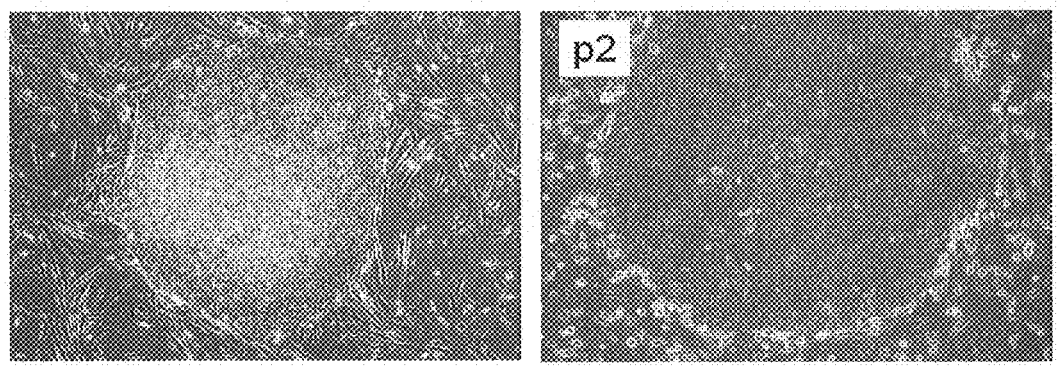
FIG. 4 is a photographic representation of colonies of an iPS cell established by transferring the four different plasmids pCXLE-hOct4, pCXLE-hSK, pCXLE-hKSO, and pCXLE-hMLN to adult human dermal fibroblasts. The left plate is a photograph as of the time of iPS cell establishment; the right plate is a photograph as of the 2nd passage (p2).

In the experiments, a fibroblast established from a facial skin from a 36-year-old Caucasian female (Cell Applications, Lot1388) was used. This fibroblast was cultured and maintained at 37° C. in the presence of 5% $CO_2$ in a 100 mm culture dish using DMEM/10% FCS [a culture broth prepared by adding 10% fetal bovine serum to DMEM (Nacalai Tesque)]. At the time of plasmid transfer, the medium was removed, and the cells were washed by the addition of 5 mL of PBS. After removing the PBS, 0.25% Trypsin/1 mM EDTA (Invitrogen) was added, and a reaction was carried out at 37° C. for about 5 minutes. After the cells rose, DMEM/10% FCS was added to suspend the cells, and $6×10^5$ cells were recovered in a 15 mL centrifugal tube. The suspension was centrifuged at 800 rpm for 5 minutes, and the supernatant was removed. A total of 3 μg of plasmids (1 μg pCXLE-hOct4, 1 μg pCXLE-hSK, 0.5 μg pCXLE-hKSO, 0.5 μg pCXLE-hMLN) was transferred to the cells using Microporator (AR BROWN). This transfer took place using a 100 μL chip with three pulses at 1650 V for 10 ms. The transfected cells were transferred to a 6-well culture plate (Falcon) containing 3 mL of DMEM/10% FCS, and cultured at 37° C. in the presence of 5% $CO_2$ for 6 days. Subsequently, the medium was removed, and the cells were washed by the addition of 2 mL of PBS. After removing the PBS, 0.25% Trypsin/1 mM EDTA (Invitrogen) was added, and a reaction was carried out at 37° C. for about 5 minutes. After the cells rose, DMEM/10% FCS was added to suspend the cells, and $1×10^5$ cells were seeded to a 100 mm dish containing previously seeded feeder cells. The feeder cells used were mitomycin C-treated MEF or SNL76/7. The following day, the medium was replaced with a primate ES cell culture medium (ReproCELL) supplemented with 4 ng/mL bFGF (Wako); this medium exchange was continued every 2 days. When MEF was used as the feeder, one human ES cell-like colony emerged on day 24. A photograph of the colony as of the time of establishment is shown in FIG. 4 (left). A photograph of the colony at the 2nd passage is shown in FIG. 4 (right). One ES-like colony could be established from $1×10^5$ cells. When SNL76/7 was used as the feeder, no iPS colonies could be established.

Example 4

Establishment of Human iPS Cells Using Episomal Plasmids (3)

As shown in Examples 2 and 3, when 6 genes consisting of Oct3/4, Sox2, Klf4, c-Myc, Lin28 and Nanog, or 7 genes consisting of the same 6 and additional SV40 large T, were transferred to cells using an episomal plasmid, only about 0 to 1 iPS cell could be established from 1 to 2×10⁵ cells. Such low induction efficiency with the use of the same 7 genes is also described in Science, 324, 797-801 (2009). Hence, to improve the establishment efficiency, L-Myc (L-Myc-Lin28 joint construct), which gave favorable results in the preliminary experiment in Example 1, was used, whereas Nanog, which had been judged to be unnecessary, was not used. Furthermore, a DNA that encodes a shRNA against human p53 [5'-<u>GACTCCAGTGGTAATCTAC</u>ttcaagagaGTAGATTACCACTGGAGTC-3' (SEQ ID NO:32): the underlined portion is the target sequence for p53; the capitalized letters indicate the portion where dsRNA is formed; hereinafter simply referred to as p53 shRNA] was also used.

Figure 30:
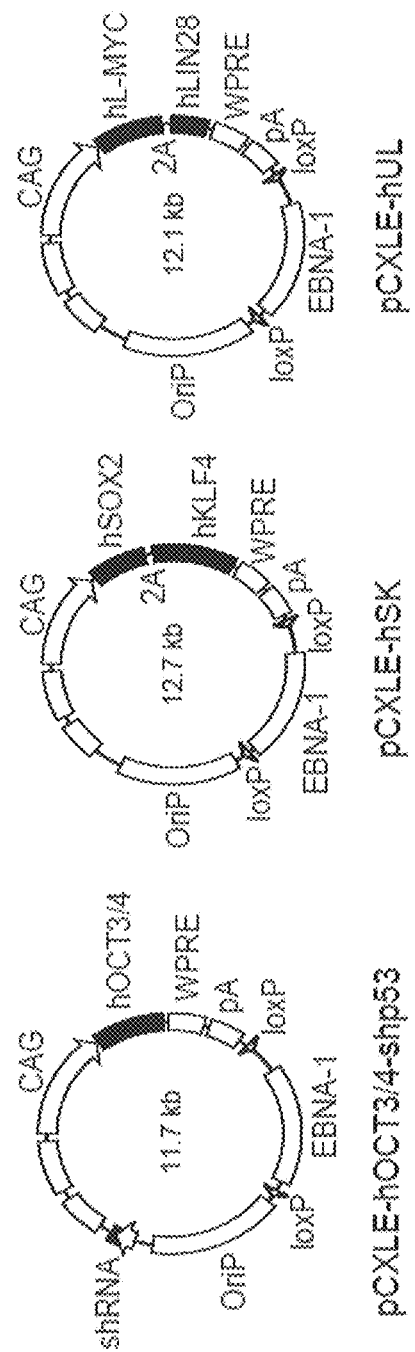
FIG. 30 shows the structures of episomal expression vectors. Three plasmids were used for the Y4 mix (in this figure, pCXLE-hOct4-shp53 is described as pCXLE-hOct3/4-shp53). Reprogramming factors (OCT3/4, SOX2, KLF4, L-MYC, LIN28, and shRNA for p53) are shown in black. The promoters (CAG), WPRE, polyadenilation signal (pA), EBNA-1, OriP, and two loxP sites are also shown.

In addition to pCXLE-hOct4, pCXLE-hSK, and pCXLE-hMLN as prepared in Example 2, 1) a plasmid prepared by treating pCXLE-EGFP as prepared in Example 2 with EcoRI, and incorporating a construct prepared by joining the translated regions of human L-Myc and human Lin28 via the 2A sequence of foot-and-mouth disease virus, in place of EGFP (pCXLE-hUL) and 2) a plasmid incorporating a construct expressing an shRNA against p53 (driven by the U6 promoter) inserted in the BamHI site of pCXLE-hOct4 (pCXLE-hOct4-shp53) were prepared and used. pCXLE-EGFP was used as a control. The structures of pCXLE-hOct4-shp53, pCXLE-hSK and pCXLE-hUL are shown in FIG. 30 (in this figure, pCXLE-hOct4-shp53 is described as pCXLE-hOct3/4-shp53).

Figure 5:
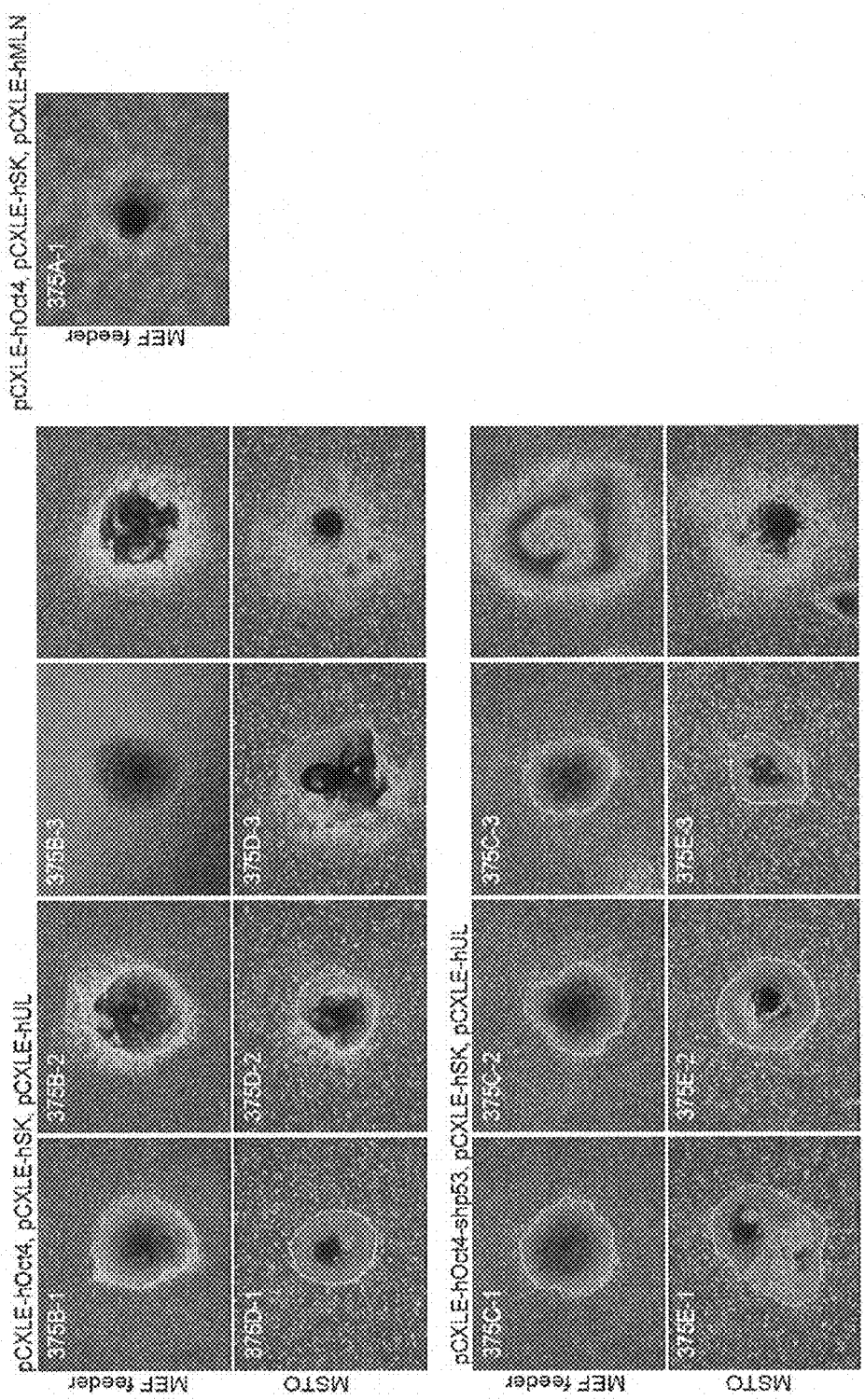
FIG. 5 is a photographic representation of colonies of iPS cells established by transferring the three different plasmids pCXLE-hOct4, pCXLE-hSK, and pCXLE-hUL (upper left panel), or the three different plasmids pCXLE-hOct4, pCXLE-hSK, and pCXLE-hMLN (upper right panel), or the three different plasmids pCXLE-hOct4-shp53, pCXLE-hSK, and pCXLE-hUL (lower left panel), to adult human dermal fibroblasts. The upper row on each panel shows the results obtained using MEF as feeder cells. The lower row on each panel shows the results obtained using MSTO cells as feeder cells. The photographs on the rightmost side without colony number on the left shoulder are photographs of non-ES-like colonies.
Figure 6:
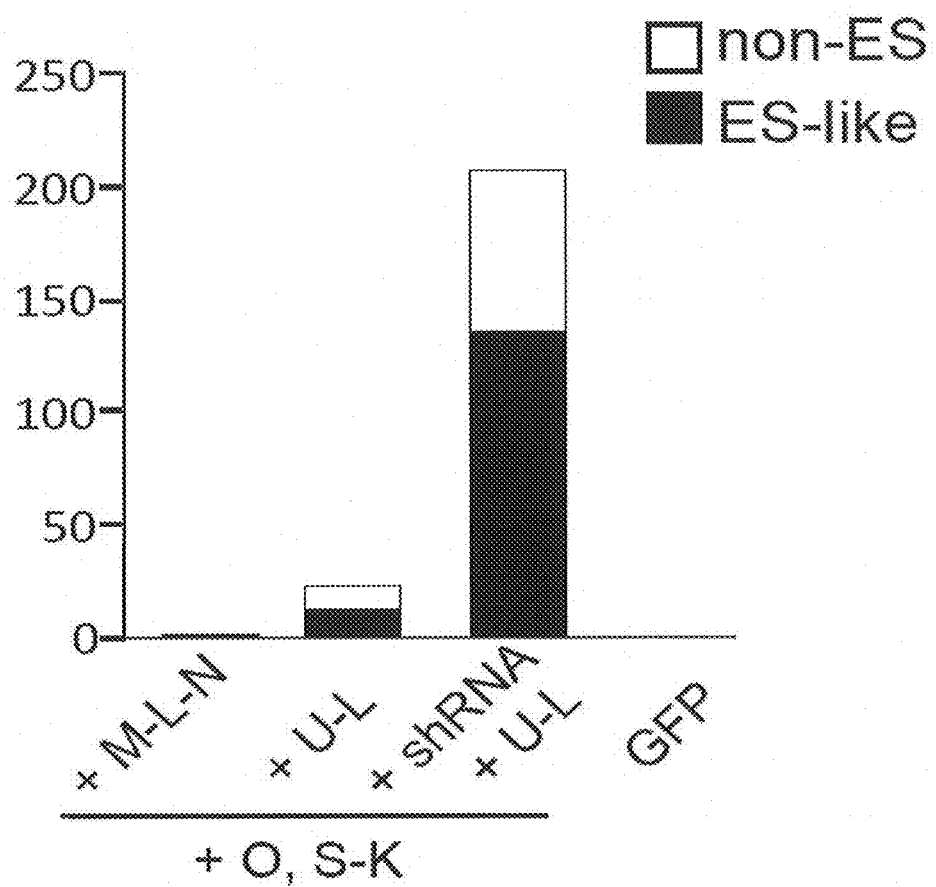
FIG. 6 is a graphic representation of the results shown in Table 2. The number of ES-like colonies is indicated by a solid bar, and the number of non-ES-like colonies by an outlined bar. Shown from the left are the results obtained by transferring each of the following combinations:
(1) pCXLE-hOct4, pCXLE-hSK, pCXLE-hMLN,
(2) pCXLE-hOct4, pCXLE-hSK, pCXLE-hUL,
(3) pCXLE-hOct4-shp53, pCXLE-hSK, pCXLE-hUL,
(4) pCXLE-GFP.

In the experiments, a fibroblast established from a skin from a 21-year-old Japanese woman (JCRB, TIG113) was used after being transfected with mouse Slc7a1 by means of lentivirus. This fibroblast was cultured and maintained at 37° C. in the presence of 5% CO₂ in a 100 mm culture dish using DMEM/10% FCS [a culture broth prepared by adding 10% fetal bovine serum to DMEM (Nacalai Tesque)]. At the time of plasmid transfer, the medium was removed, and the cells were washed by the addition of 5 mL of PBS. After removing the PBS, 0.25% Trypsin/1 mM EDTA (Invitrogen) was added, and a reaction was carried out at 37° C. for about 5 minutes. After the cells rose, DMEM/10% FCS was added to suspend the cells, and 6×10⁵ cells were recovered in a 15 mL centrifugal tube. The suspension was centrifuged at 800 rpm for 5 minutes, and the supernatant was removed. The plasmids shown in Table 2 (3 µg in total) were transferred to the cells using Microporator (AR BROWN). This transfer took place using a 100 µL chip with three pulses at 1650 V for 10 ms. The transfected cells were transferred to a 6-well culture plate (Falcon) containing 3 mL of DMEM/10% FCS, and cultured at 37° C. in the presence of 5% CO₂ for 7 days. Subsequently, the medium was removed, and the cells were washed by the addition of 2 mL of PBS. After removing the PBS, 0.25% Trypsin/1 mM EDTA (Invitrogen) was added, and a reaction was carried out at 37° C. for about 5 minutes. After the cells rose, DMEM/10% FCS was added to suspend the cells, and 1.5×10⁵ cells were seeded to a 100 mm dish containing previously seeded feeder cells. The feeder cells used were mitomycin C-treated MEF or SNL76/7. The following day, the medium was replaced with a primate ES cell culture medium (ReproCELL) supplemented with 4 ng/mL bFGF (Wako); this medium exchange was continued every 2 days. On day 28, the human ES cell-like colonies that had emerged were counted. Photographs of the colonies are shown in FIG. 5. Results of colony counting are shown in Table 2 and FIG. 6 (MEF used as feeder).

TABLE 2

| | Vector contents (µg) (Microporator conditions: 1650 V, 10 ms, x3) | | | | | | MEF feeder | | MSTO feeder | |
|---|---|---|---|---|---|---|---|---|---|---|
| Exp. No. | pCXLE-hOct4 | pCXLE-hOct4-shp53 | pCXLE-hSK | pCXLE-hMLN | pCXLE-hUL | pCXLE-EGFP | non-ES like | ES like | non-ES like | ES like |
| 375A | 1 | | 1 | 1 | | | 0 | 1 | 0 | 0 |
| 375B, D | 1 | | 1 | | 1 | | 10 | 13 | 3 | 6 |
| 375C, E | | 1 | 1 | | 1 | | 71 | 136 | 87 | 132 |
| control | | | | | | 3 | 0 | 0 | 0 | 0 |

375A-C: MEF feeder; 375D-E: MSTO feeder

Although iPS colonies (ES-like colonies) could be established whichever feeders were used, more colonies were established with the use of MEF. When 5 genes consisting of Oct3/4, Sox2, Klf4, L-Myc, and Lin28 were used, the establishment efficiency increased compared with the use of the conventional 6 genes (Oct3/4, Sox2, Klf4, c-Myc, Lin28 and Nanog). As the p53 shRNA was further added, the establishment efficiency increased dramatically.

Example 5

Establishment of Human iPS Cells Using Episomal Plasmids (4)

The plasmids used for reprogramming were the same as the five different plasmids pCXLE-hOct4, pCXLE-hSK, pCXLE-hMLN, pCXLE-hUL, and pCXLE-hOct4-shp53 in Example 4; pCXLE-EGFP was used as a control.

Figure 7:
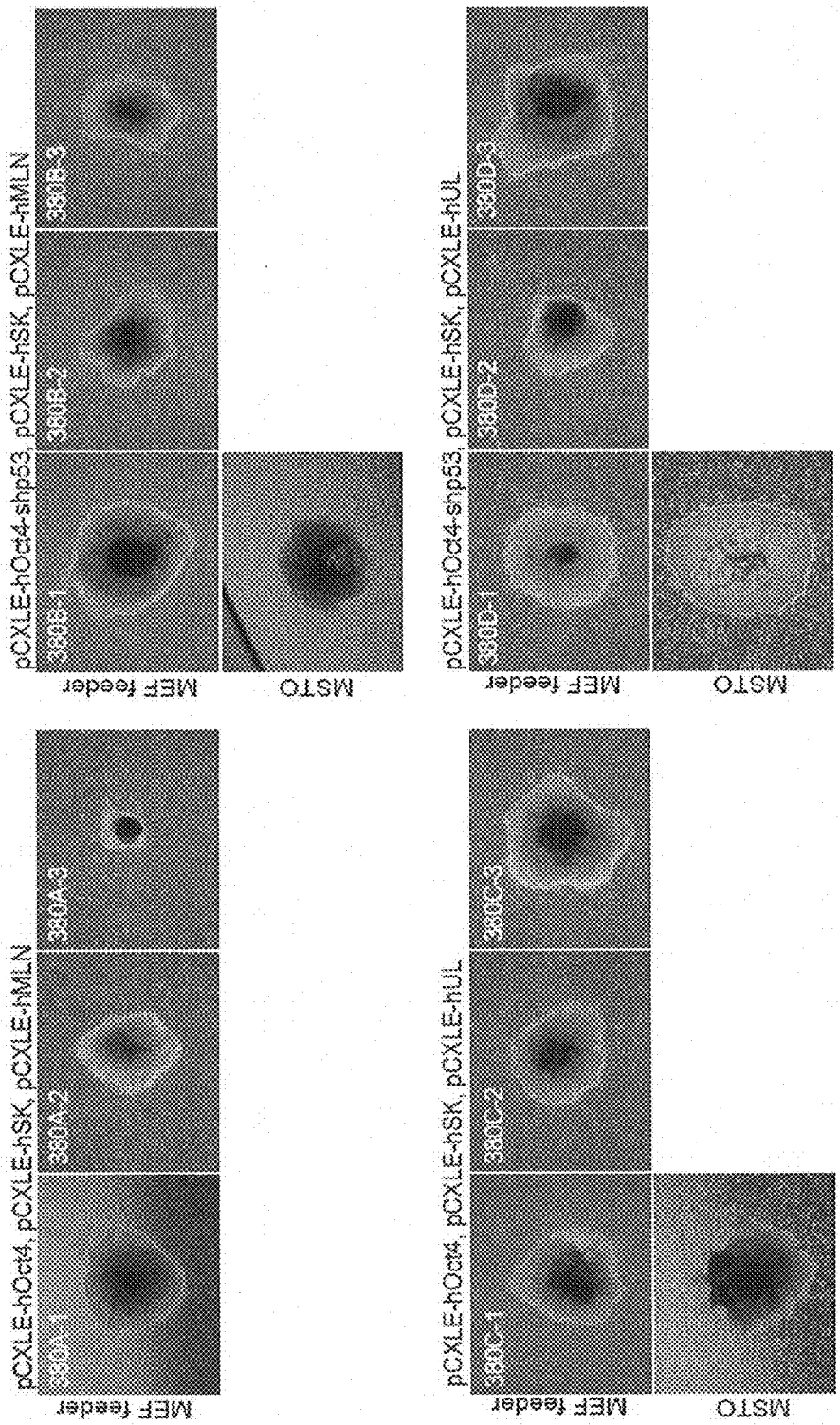
FIG. 7 is a photographic representation of colonies of iPS cells established by transferring the three different plasmids pCXLE-hOct4, pCXLE-hSK, and pCXLE-hMLN (upper left panel), or the three different plasmids pCXLE-hOct4, pCXLE-hSK, and pCXLE-hUL (lower left panel), or the three different plasmids pCXLE-hOct4-shp53, pCXLE-hSK, and pCXLE-hMLN (upper right panel), or the three different plasmids pCXLE-hOct4-shp53, pCXLE-hSK, and pCXLE-hUL (lower right panel), to fibroblasts derived from a skin of a 6-year-old human. The upper row on each panel shows the results obtained using MEF as feeder cells. The lower row on each panel shows the results obtained using MSTO cells as feeder cells.
Figure 8:
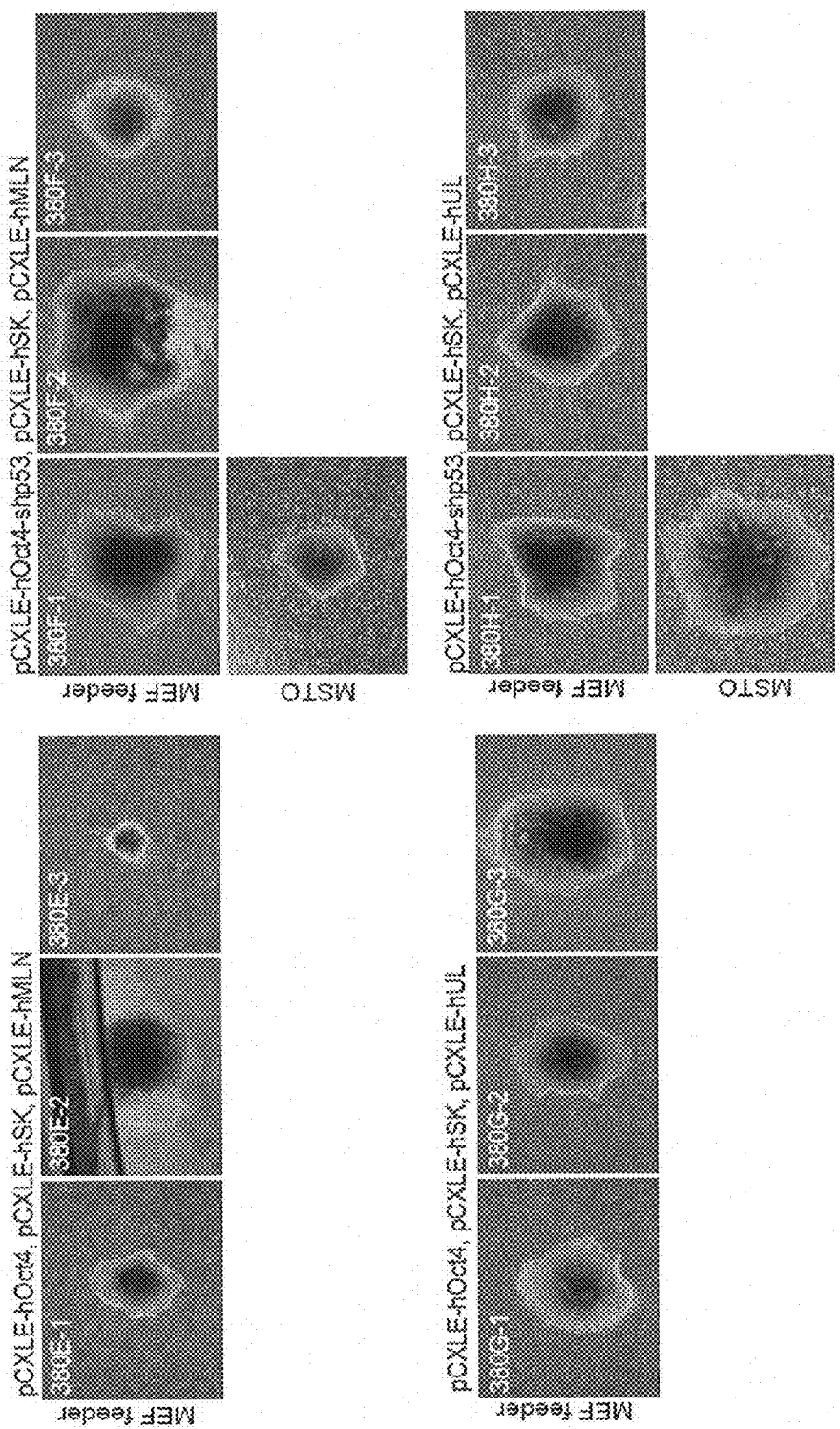
FIG. 8 is a photographic representation of colonies of iPS cell established by transferring the three different plasmids pCXLE-hOct4, pCXLE-hSK, and pCXLE-hMLN (upper left panel), or the three different plasmids pCXLE-hOct4, pCXLE-hSK, and pCXLE-hUL (lower left panel), or the three different plasmids pCXLE-hOct4-shp53, pCXLE-hSK, and pCXLE-hMLN (upper right panel), or the three different plasmids pCXLE-hOct4-shp53, pCXLE-hSK, and pCXLE-hUL (lower right panel), to fibroblasts derived from a skin of an 8-month-old human. The upper row on each panel shows the results obtained using MEF as feeder cells. The lower row on each panel shows the results obtained using MSTO cells as feeder cells.
Figure 9:
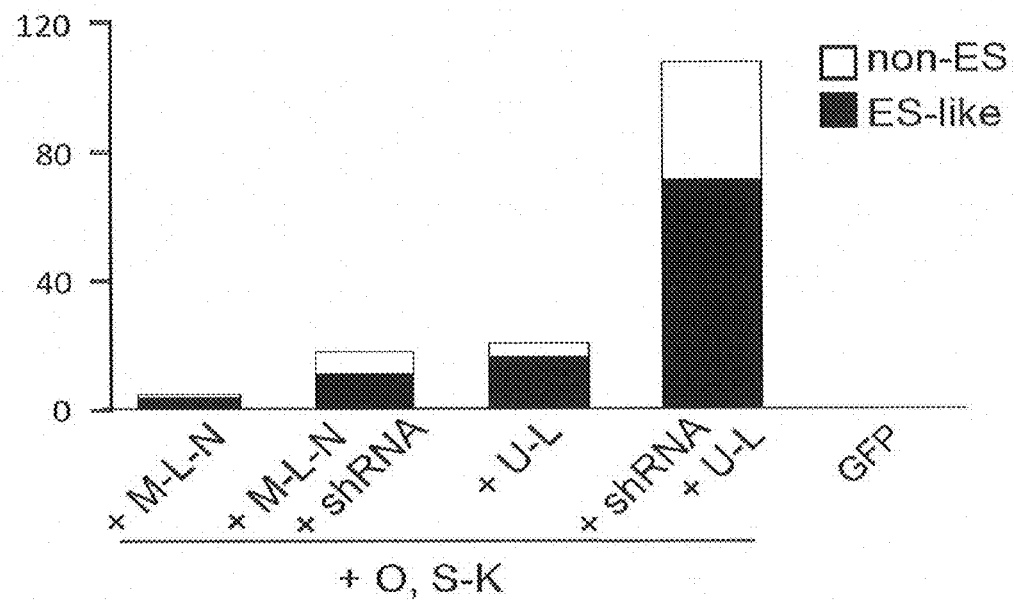
FIG. 9 is a graphic representation of results shown in Table 3 (TIG120 used). The number of ES-like colonies is indicated by a solid bar, and the number of non-ES-like colonies by an outlined bar. Shown from the left are the results obtained by transferring each of the following combinations:
(1) pCXLE-hOct4, pCXLE-hSK, pCXLE-hMLN,
(2) pCXLE-hOct4-shp53, pCXLE-hSK, pCXLE-hMLN,
(3) pCXLE-hOct4, pCXLE-hSK, pCXLE-hUL,
(4) pCXLE-hOct4-shp53, pCXLE-hSK, pCXLE-hUL,
(5) pCXLE-GFP.
Figure 10:
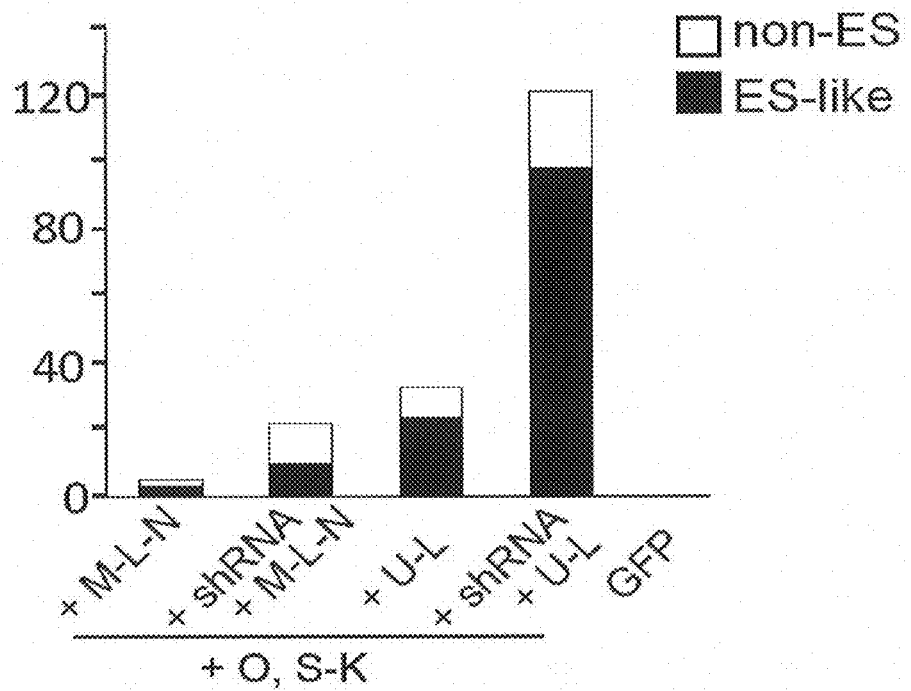
FIG. 10 is a graphic representation of results shown in Table 3 (TIG121 used). The number of ES-like colonies is indicated by a solid bar, and the number of non-ES-like colonies by an outlined bar. Shown from the left are the same as (1) to (5) in the explanation for FIG. 9.

In the experiments, a fibroblast established from a skin from a 6-year-old Japanese female (JCRB, TIG120) and a fibroblast established from a skin from an 8-month-old Japanese male (JCRB, TIG121) were used after being transfected with mouse Slc7a1 by means of lentivirus. These fibroblasts were cultured and maintained at 37° C. in the presence of 5% CO₂ in a 100 mm culture dish using DMEM/10% FCS [a culture broth prepared by adding 10% fetal bovine serum to DMEM (Nacalai Tesque)]. At the time of plasmid transfer, the medium was removed, and the cells were washed by the addition of 5 mL of PBS. After removing the PBS, 0.25% Trypsin/1 mM EDTA (Invitrogen) was added, and a reaction was carried out at 37° C. for about 5 minutes. After the cells rose, DMEM/10% FCS was added to suspend the cells, and 6×10⁵ cells were recovered in a 15 mL centrifugal tube. The suspension was centrifuged at 800 rpm for 5 minutes, and the supernatant was removed. The plasmids shown in Table 3 (3 µg in total) were transferred to the cells using Microporator (AR BROWN). This transfer took place using a 100 µL chip with three pulses at 1650 V for 10 ms. The transfected cells were transferred to a 6-well culture plate (Falcon) containing 3 mL of DMEM/10% FCS, and cultured at 37° C. in the presence of 5% $CO_2$ for 7 days. Subsequently, the medium was removed, and the cells were washed by the addition of 2 mL of PBS. After removing the PBS, 0.25% Trypsin/1 mM EDTA (Invitrogen) was added, and a reaction was carried out at 37° C. for about 5 minutes. After the cells rose, DMEM/10% FCS was added to suspend the cells, and $1 \times 10^5$ cells were seeded to a 100 mm dish containing previously seeded feeder cells. The feeder cells used were mitomycin C-treated MEF or SNL76/7. The following day, the medium was replaced with a primate ES cell culture medium (Repro-CELL) supplemented with 4 ng/mL bFGF (Wako); this medium exchange was continued every 2 days. On day 28, the human ES cell-like colonies that had emerged were counted. Photographs of the colonies are shown in FIG. 7 (TIG120 used) and FIG. 8 (TIG121 used). Results of colony counting are shown in Table 3, FIG. 9 (TIG120 used, MEF used as feeder) and FIG. 10 (TIG121 used, MEF used as feeder).

lysate was incubated at 55° C. overnight. This was admixed with 150 μL of PCI (a 25:24:1 mixture of phenol, chloroform and isoamyl alcohol) for 15 minutes, and centrifuged at 13200 rpm for 10 minutes. The aqueous layer (the upper layer) was recovered and mixed with 1 mL of ethanol. The resulting precipitate was recovered in another tube, and this was used as the long DNA. The remaining liquid deprived of the precipitate was centrifuged at 13200 rpm for 15 minutes. The resulting precipitate was used as the short DNA. Each DNA was washed with 70% ethanol and dissolved in TE buffer to obtain a PCR template. PCR was performed using TaKaRa EX Taq (Takara Shuzo), with 50 ng of the long DNA or 250 ng of the short DNA used as a template in each reaction. The following primers were used in combination.
Detection of Klf4: hKlf4-S1016 ACC CAT CCT TCC TGC CCG ATC AGA (SEQ ID NO:33)
hKlf4-AS1170 ATC ACA AGT GTG GGT GGC GGT CCT (SEQ ID NO:34)

TABLE 3

| | | Vector contents (μg) (Microporator conditions: 1650 V, 10 ms, x3) | | | | | | MEF feeder | | MSTO feeder | |
| | | pCXLE- | | | | | | | | | |
| Exp. No. | HDF source | pCXLE-hOct4 | pCXLE-hOct4-shp53 | pCXLE-hSK | pCXLE-hMLN | pCXLE-hUL | pCXLE-EGFP | non-ES like | ES like | non-ES like | ES like |
|---|---|---|---|---|---|---|---|---|---|---|---|
| 380A | TIG120 | 1 | | 1 | 1 | | | 1 | 3 | 0 | 0 |
| 380B | TIG120 | | 1 | 1 | 1 | | | 7 | 11 | 1 | 2 |
| 380C | TIG120 | 1 | | 1 | | 1 | | 4 | 16 | 0 | 4 |
| 380D | TIG120 | | 1 | 1 | | 1 | | 37 | 71 | 17 | 25 |
| Control | TIG120 | | | | | | 3 | 0 | 0 | 0 | 0 |
| 380E | TIG121 | 1 | | 1 | 1 | | | 2 | 3 | 0 | 0 |
| 380F | TIG121 | | 1 | 1 | 1 | | | 11 | 10 | 1 | 4 |
| 380G | TIG121 | 1 | | 1 | | 1 | | 9 | 23 | 0 | 0 |
| 380H | TIG121 | | 1 | 1 | | 1 | | 24 | 97 | 5 | 11 |
| Control | TIG121 | | | | | | 3 | 0 | 0 | 0 | 0 |

Compared with the use of the conventional 6 genes (Oct3/4, Sox2, Klf4, c-Myc, Lin28 and Nanog), the establishment efficiency increased with the use of additional p53 shRNA. Furthermore, when 5 genes consisting of Oct3/4, Sox2, Klf4, L-Myc, and Lin28 were used, the establishment efficiency increased compared with the use of the conventional 6 genes. As p53 shRNA was further added, the establishment efficiency still increased dramatically.

Figure 11:
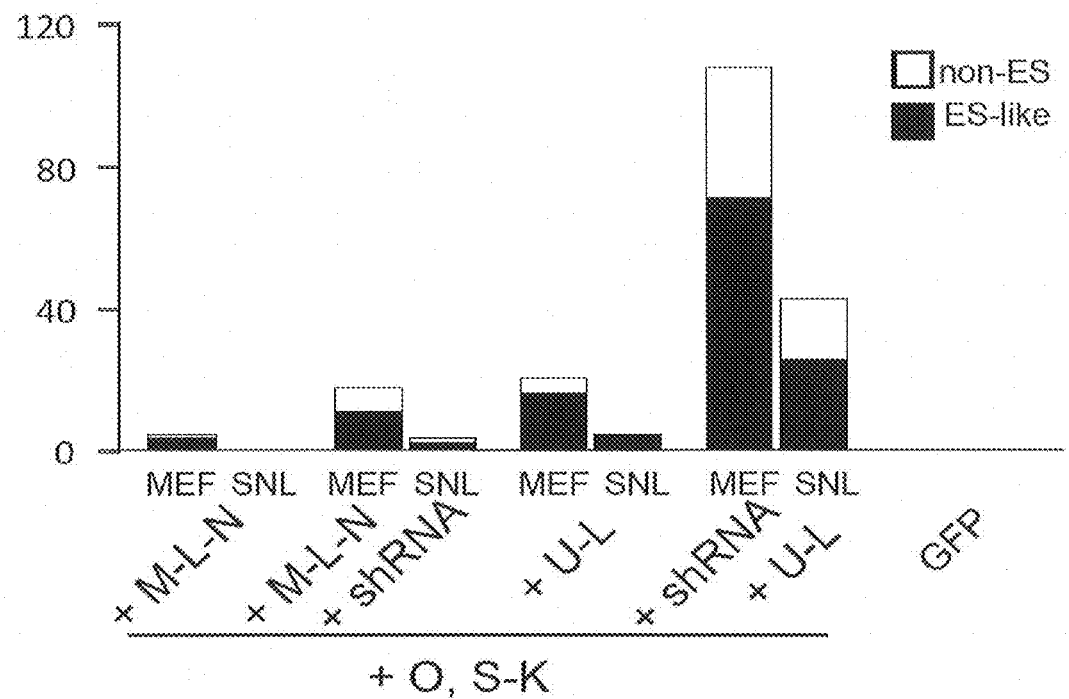
FIG. 11 is a graphic representation of results shown in Table 3 (TIG120 used) for each type of feeder cell. Shown from the left are the same as (1) to (5) in the explanation for FIG. 9.

Results obtained with the use of MEF as feeder cells and those obtained with the use of SNL76/7 (MSTO) are compared in FIG. 11 (TIG120 used). Although iPS colonies (ES-like colonies) could be established whichever of the feeders was used, a larger number of colonies were established with the use of MEF.

Example 6

Confirmation of the Presence or Absence of Exogenous Genes in iPS Colonies (1)

Five different iPS cells established by transferring reprogramming genes using an episomal plasmid were examined for the presence or absence of the integration of the exogenous genes in the genome.

After becoming nearly confluent in a 6-well culture plate (Falcon), the iPS cells were washed by the addition of 2 mL of PBS. After removing the PBS, 400 μL of a genome recovery buffer (50 mM Tris-HCl, 20 mM EDTA, 100 mM NaCl, 1% SDS, 50 μg/mL proteinase K) was added to lyse the cells, and the cells were recovered in a 1.5 mL tube, after which the cell Detection of c-Myc: hMyc-S547 GCC GCC GCC TCA GAG TGC ATC GAC (SEQ ID NO:35)
hMyc-AS947 CGA GTG GAG GGA GGC GCT GCG TAG (SEQ ID NO:36)
Detection of OriP derived from pCEP4: pEP4-SF1 TTC CAC GAG GGT AGT GAA CC (SEQ ID NO:37)
pEP4-SR1 TCG GGG GTG TTA GAG ACA AC (SEQ ID NO:38)

Figure 12:
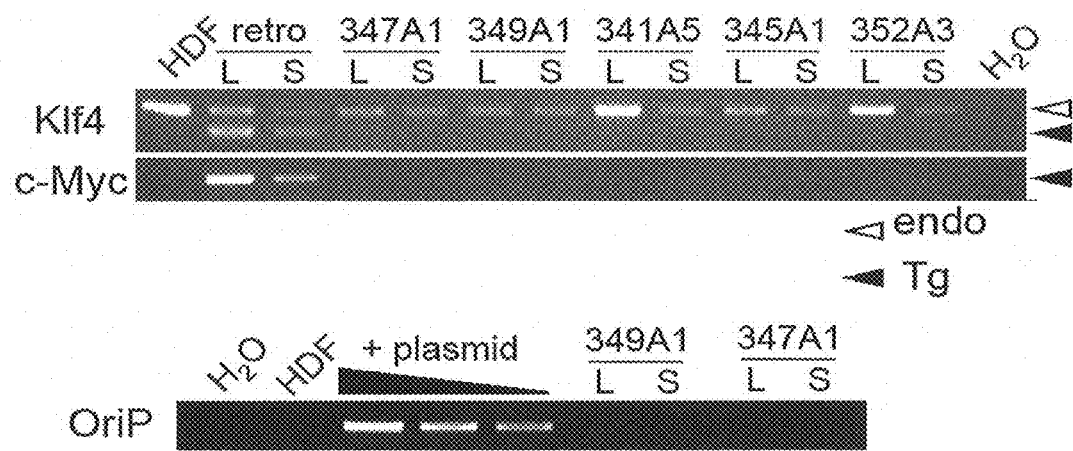
FIG. 12 shows results of an examination of 5 different iPS cells for the presence or absence of the integration of exogenous genes (Klf4, c-Myc, OriP) in the genome by genomic PCR, wherein "L" indicates the results for the long DNA, and "S" for the short DNA. Indicated by "347A1" are the results for the iPS colony established in Example 2; "349A1" indicates the results for the iPS colony established in Example 3; "341A5" indicates the results for an iPS colony established by transferring 6 genes consisting of Oct3/4, Sox2, Klf4, c-Myc, Lin28, and Nanog to fetal human fibroblasts; "345A1" indicates the results for another iPS colony obtained by transferring the same genes as those for "347A1"; and "352A3" indicates the results for another iPS colony obtained by transferring the same genes as those for "341A5". HDF indicates the results for the genome of a non-transfected fetal human fibroblast, and "retro" for iPS colonies established by transferring 4 genes consisting of Oct3/4, Sox2, Klf4, and c-Myc to fetal human fibroblasts using a retroviral vector.

At the time of detection of OriP, PCR was also performed on controls prepared by adding 200, 20, or 2 fg of the plasmid that had been transferred to the genome (50 ng) of the starting fibroblast ("+plasmid" in FIG. 12). The results are shown in FIG. 12. In any of the iPS cells examined, none of Klf4 and c-Myc from the exogenous gene (Tg) and the vector constituent OriP was detected in the long DNA (L in FIG. 12) or the short DNA (S in FIG. 12); it was estimated that the episomal plasmid transferred had spontaneously been shed the cell.

Example 7

Establishment of Human iPS Cells Using Episomal Plasmid (5)

Fibroblasts established from skins from male and female Japanese and Caucasian subjects at various ages (HDF) as sources of somatic cells were transfected with 5 genes consisting of Oct3/4, Sox2, Klf4, L-Myc, and Lin28, along with p53 shRNA, using pCXLE-hOct4-shp53, pCXLE-hSK and pCXLE-hUL in the same manner as Example 5. MSTO or MEF served as feeder cells. The fibroblasts were supplied in two forms, one with mouse Slc7a1 incorporated therein, and the other without. Human ES cell-like colonies that emerged on days 27 to 32 after the transfection were counted. The results (n=1 to 5) are shown together in Table 4.

TABLE 4

| Name | Age | Sex[1] | Race[2] | Colony No. | N |
|------|-----|--------|---------|------------|---|
| HDF1419 | fetus | F | — | 68.7 | 4 |
| TIG121 | 8 m | M | J | 97 | 1 |
| TIG120 | 6 | F | J | 41.7 | 4 |
| HDF1388 | 36 | F | C | 3.4 | 5 |
| TIG114 | 36 | M | J | 4 | 1 |
| HDF1429 | 45 | M | C | 50 | 1 |
| HDF1377 | 53 | F | C | 26 | 1 |
| HDF1437 | 56 | M | C | 47 | 3 |
| HDF1554 | 77 | F | C | 12 | 2 |
| TIG107 | 81 | F | J | 3.5 | 2 |

[1]F: Female, M: Male
[2]J: Japanese, C: Caucasian

In the table above, colony counts are shown as mean numbers of colonies established per $1\times10^5$ HDFs. As is evident from Table 4, it was found that iPS cells could be established irrespective of the age, sex, and race of the cell source subject. It was also found that iPS cells could be established whether Slc7a1 was transferred (no separate data shown).

Example 8

Transfer of p53 shRNA Using Transient Expression Plasmid

The p53 gene is known as a cancer suppression gene; functional inhibition of p53 for a long time potentially increases the risk of carcinogenesis. Hence, an investigation was made to determine whether iPS cells could be established as with an episomal vector even when p53 shRNA was expressed by means of a transient expression vector (an ordinary plasmid vector lacking the EBNA-1 and oriP: hereinafter, the plasmid vector).

Figure 13:
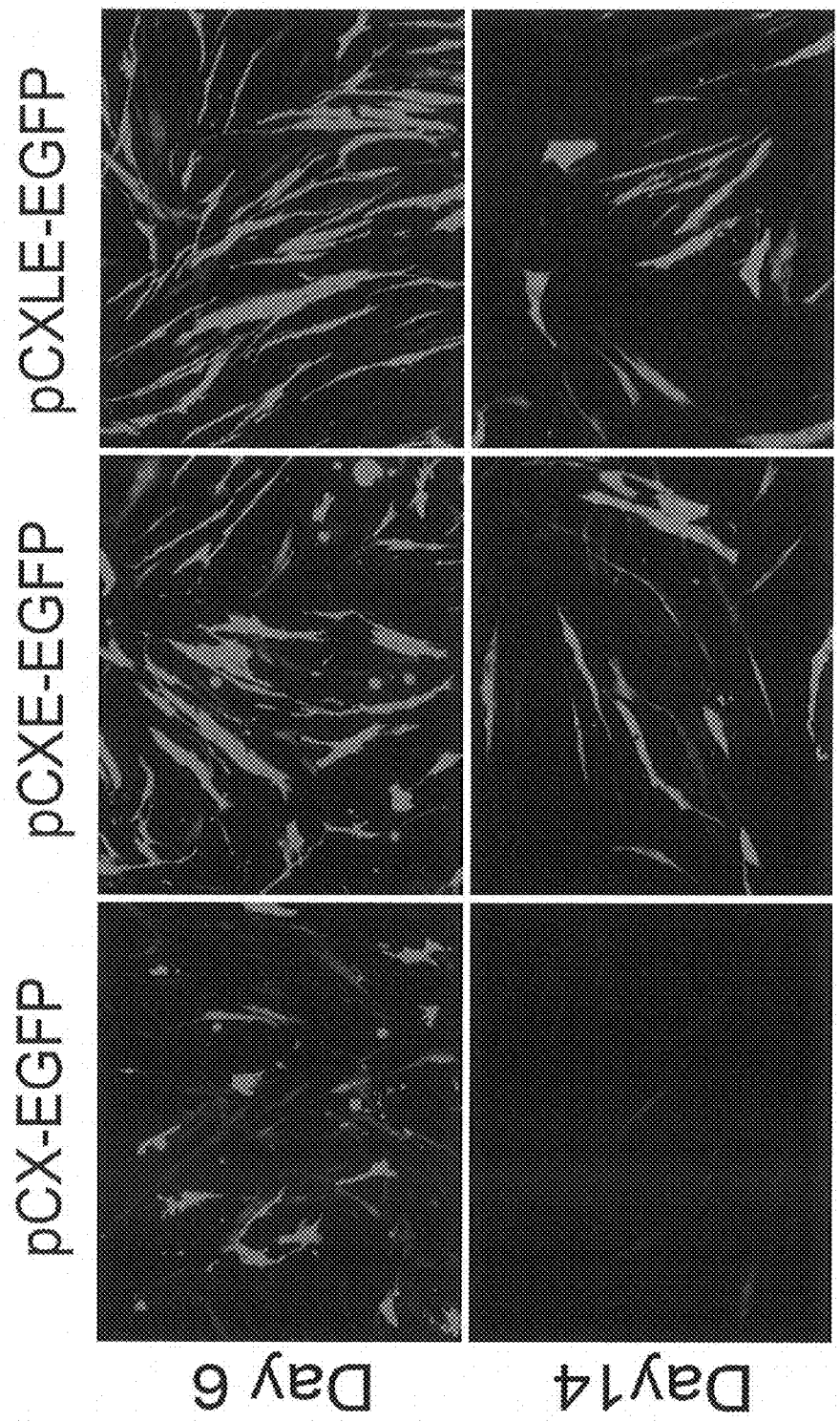
FIG. 13 shows fluorescence photographs (GFP observation images) of cells obtained by transferring pCX-EGFP, pCXE-EGFP and pCXLE-EGFP to HDF, taken on days 6 and 14 after the transfer.

A preliminary study was conducted to determine whether there was a difference in the extent of disappearance of gene expression between an episomal vector and the plasmid vector. In the experiment, pCX-EGFP (supplied by Dr. Masaru Okabe at Osaka University; FEBS Letters, 407, 313-319, 1997), pCXLE-EGFP as prepared in Example 2, and pCXE-EGFP (a plasmid prepared by removing the loxP sequences from pCXLE-EGFP) were used. On days 6 and 14 after transferring each plasmid into HDF1419, the expression of GFP was examined. This transfer took place using Microporator and a 100 μL chip with three pulses at 1650 V for 10 ms. The results are shown in FIG. 13. For all plasmids, GFP fluorescence was observed on day 6, but the amount expressed was lower for pCX-EGFP than for the other two. On day 14, fluorescence was still observed, but the amount expressed was considerably lower for pCX-EGFP than for the other two. These findings confirmed that gene expression disappears earlier in plasmid vectors than in episomal vectors.

Next, an investigation was made to determine whether an iPS cell could be established even when p53 shRNA was transferred using a plasmid vector. For the transfer, the following plasmid or episomal vectors were used.
(a) pCXLE-hOct4-shp53, pCXLE-hSK, pCXLE-hMLN
(b) pCXLE-hOct4, pCXLE-hSK, pCXLE-hMLN, pSilencer-shp53 [pSilencer-shp53 prepared by inserting p53 shRNA downstream of the U6 promoter of pSilencer™ (Ambion)]
(c) pCXLE-hOct4-shp53, pCXLE-hSK, pCXLE-hUL
(d) pCXLE-hOct4, pCXLE-hSK, pCXLE-hUL, pSilencer-shp53

For the transfer, 0.75 μg [(b) and (d)] or 1 μg [(a) and (c)] of each vector was used (3 μg in total).

Figure 14:
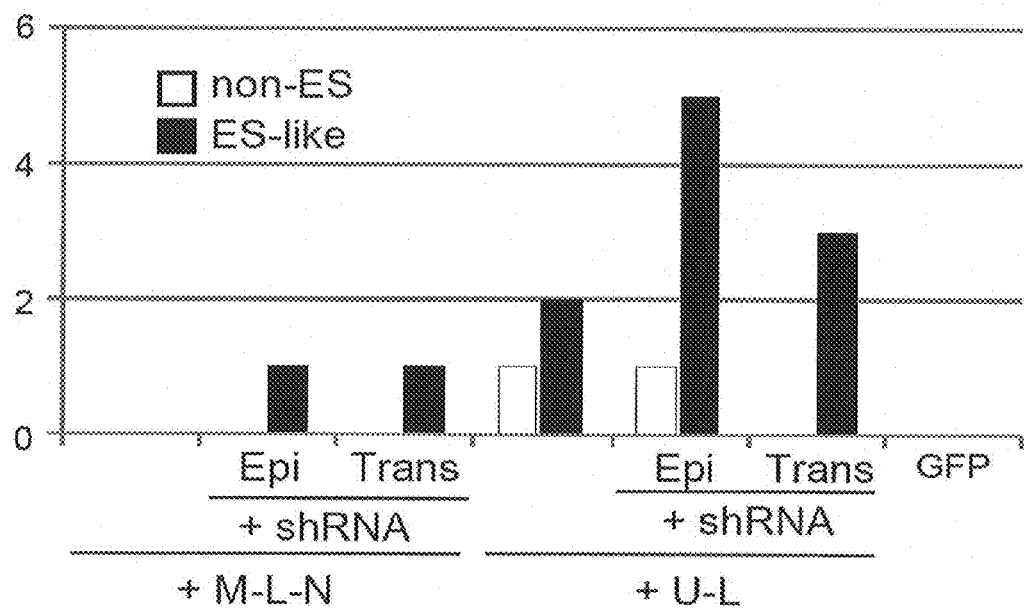
FIG. 14 is a graphic representation of results of an examination to determine whether an iPS cell can be established even when a p53 shRNA is transferred using a plasmid vector (a plasmid vector lacking the EBNA-1 and oriP). The number of ES-like colonies is indicated by a solid bar, and the number of non-ES-like colonies by an outlined bar. Shown from the left are the results obtained by transferring each of the following combinations:
(1) pCXLE-hOct4, pCXLE-hSK, pCXLE-hMLN,
(2) pCXLE-hOct4-shp53, pCXLE-hSK, pCXLE-hMLN,
(3) pCXLE-hOct4, pCXLE-hSK, pCXLE-hMLN, pSilencer-shp53,
(4) pCXLE-hOct4, pCXLE-hSK, pCXLE-hUL,
(5) pCXLE-hOct4-shp53, pCXLE-hSK, pCXLE-hUL,
(6) pCXLE-hOct4, pCXLE-hSK, pCXLE-hUL, pSilencer-shp53,
(7) pCXLE-EGFP.

An iPS cell was established in the same manner as Example 5 using a fibroblast established from a skin from a 36-year-old Caucasian female (HDF1388) as a somatic cell, with MEF as feeder cells. The transfer took place using Microporator and a 100 μL chip with three pulses at 1650 V for 10 ms. On day 27 after the transfer, the human ES cell-like colonies that had emerged were counted. The results are shown in FIG. 14. Comparing the combinations (a) and (b) (Epi versus Trans of +M-L-N in FIG. 14), and the combinations (c) and (d) (Epi versus Trans of +U-L in FIG. 14), there was no major difference in the number of colonies established between the use of an episomal vector for transferring the p53 shRNA and the use of the plasmid vector; it was demonstrated that an iPS cell can be established well even using the plasmid vector for transfer.

Example 9

Establishment of iPS Cells from Dental Pulp Stem Cells Derived from Healthy Humans with Homo-HLA Genotype Dental pulp stem cells from healthy humans with the homo-genotype for the four gene loci HLA-A, HLA-B, HLA-Cw and HLA-DRB1 (cell lines DP74 and DP94) were supplied by Drs. Takahiro Kunisada and Kenichi Tezuka at Gifu University. These cell lines had been established as described in J. Dent. Res., 87 (7): 676-681 (2008) and WO 2010/013359. The aforementioned four HLA genotypes of the two cell lines and the allelic frequency thereof [frequency of each allele (haplotype) having the four HLA genotypes in all alleles in Japanese people] are shown in Table 5.

TABLE 5

| | HLA allele | | | | |
|---|---|---|---|---|---|
| | A | B | Cw | DRB1 | population |
| DP74 | 2402 | 5201 | 1202 | 1502 | 10% |
| DP94 | 1101 | 1501 | 0401 | 0406 | 1.5% | iPS cells were established in the same manner as Example 5 using five different plasmids for reprogramming: pCXLE-hOct4, pCXLE-hSK, pCXLE-hMLN, pCXLE-hUL and pCXLE-hOct4-shp53. iPS cells were also established by transferring the plasmid described in Science, 324: 797-801 (2009) (Thomson's mix). A total of 3 μg of vector was used in each case; this transfer took place using Microporator and a 100 μL chip with three pulses at 1650 V for 10 ms. MSTO was used as feeder cells.

Figure 15:
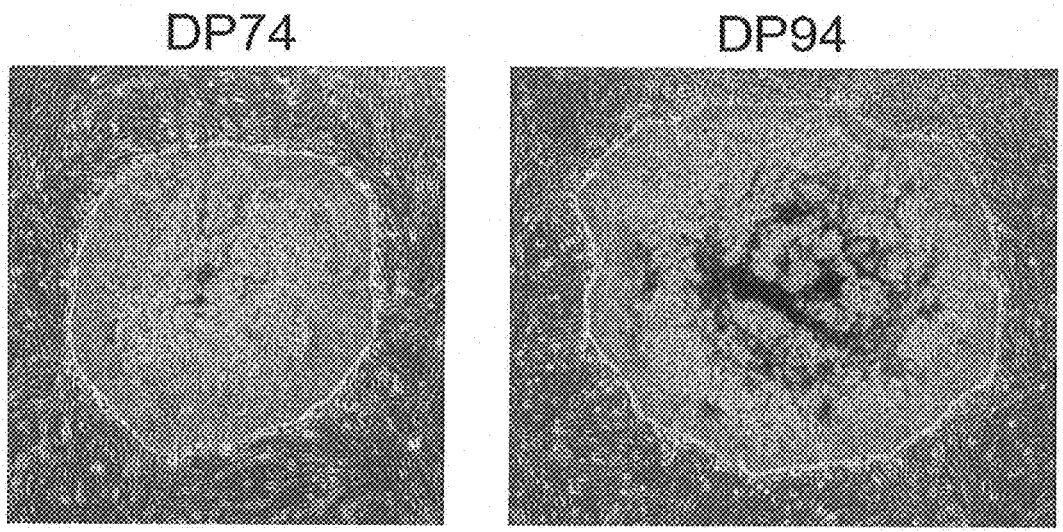
FIG. 15 is a photographic representation of colonies of an iPS cell established by transferring pCXLE-hOct4-shp53, pCXLE-hSK and pCXLE-hUL to dental pulp stem cell lines DP74 and DP94 from a healthy human with the homo-HLA 4 genotype.
Figure 16:
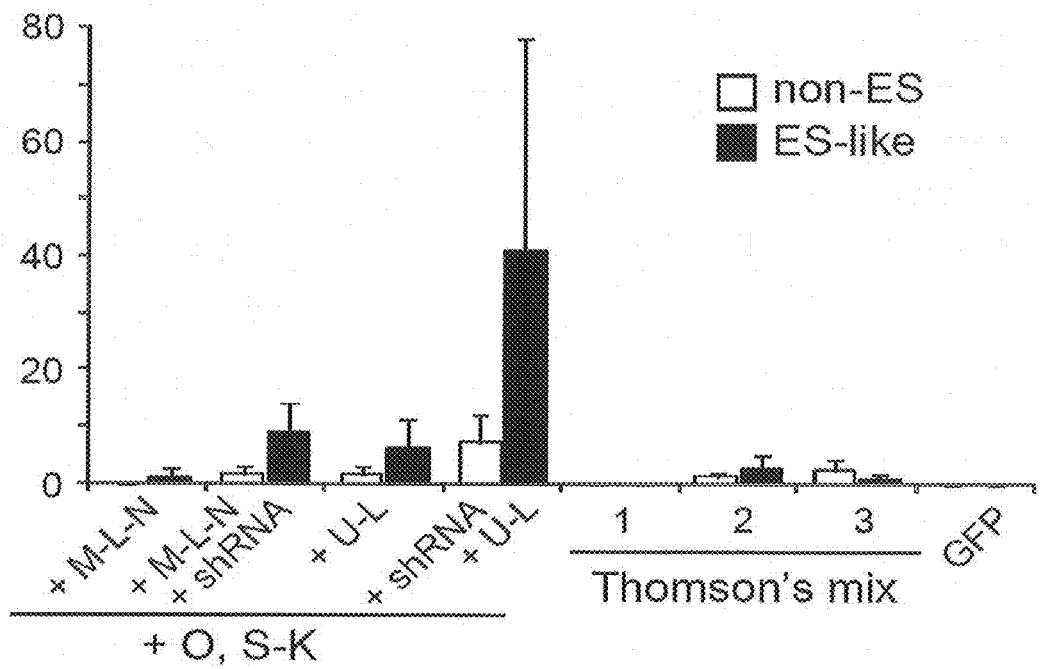
FIG. 16 is a graphic representation of results of counting ES-like colonies obtained by transferring various reprogramming genes to the dental pulp stem cell line DP74. The number of ES-like colonies is indicated by a solid bar, and the number of non-ES-like colonies by an outlined bar. Shown from the left are the results obtained by transferring each of the following combinations:
(1) pCXLE-hOct4, pCXLE-hSK, pCXLE-hMLN,
(2) pCXLE-hOct4-shp53, pCXLE-hSK, pCXLE-hMLN,
(3) pCXLE-hOct4, pCXLE-hSK, pCXLE-hUL,
(4) pCXLE-hOct4-shp53, pCXLE-hSK, pCXLE-hUL,
(5) pEP4-EO2S-ET2K, pEP4-EO2S-EN2K, pCEP4-M2L (Thomson's mix 1 in FIG. 16),
(6) pEP4-EO2S-ET2K, pEP4-EO2S-Ck2M-EN2L (Thomson's mix 2 in FIG. 16), (7) pEP4-EO2S-ET2K, pEP4-EO2S-EN2L, pEP4-EO2S-EM2K (Thomson's mix 3 in FIG. 16),
(8) pCXLE-GFP.
Figure 17:
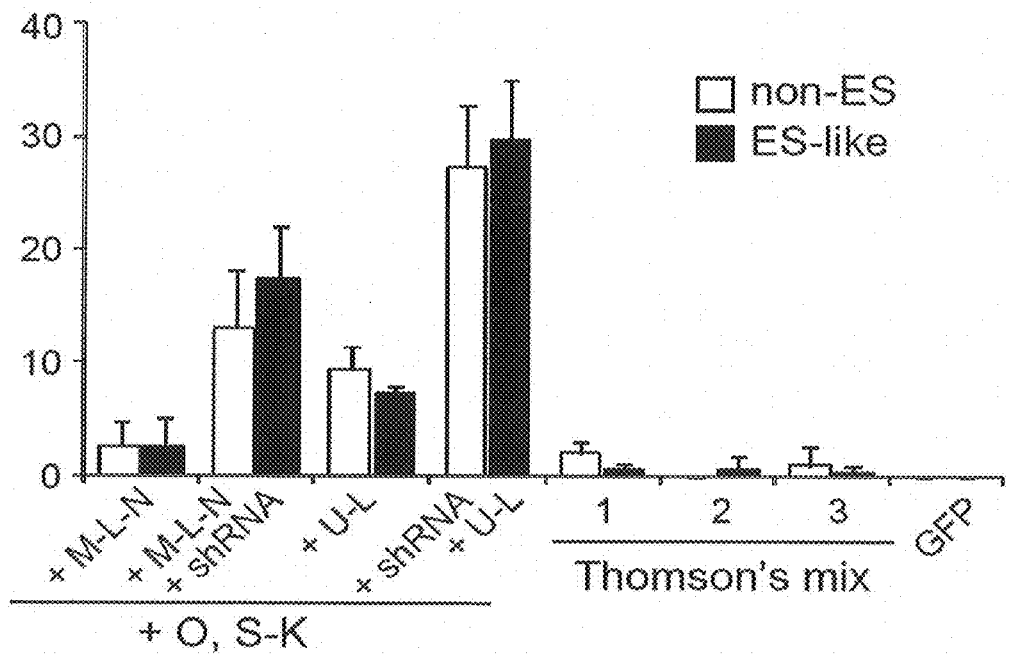
FIG. 17 is a graphic representation of results of the same experiment as FIG. 16, but using the DP94 line.

Photographs of iPS cells established by transferring pCXLE-hOct4-shp53, pCXLE-hSK and pCXLE-hUL to DP74 and DP94 are shown in FIG. 15. The human ES cell-like colonies that emerged on day 28 after the transfer were counted. The results are shown in FIGS. 16 and 17 (each numerical figure indicates the mean and standard deviation for three experiments). For both the DP74 line (FIG. 16) and DP94 line (FIG. 17), the highest establishment efficiency was obtained with the transfer of 5 genes consisting of Oct3/4, Sox2, Klf4, L-Myc, and Lin28, along with p53 shRNAs (pCXLE-hOct4-shp53, pCXLE-hSK and pCXLE-hUL); good results were obtained as with HDF.

Example 10

Confirmation of the Presence or Absence of Exogenous Genes in iPS Colonies (2)

Figure 18:
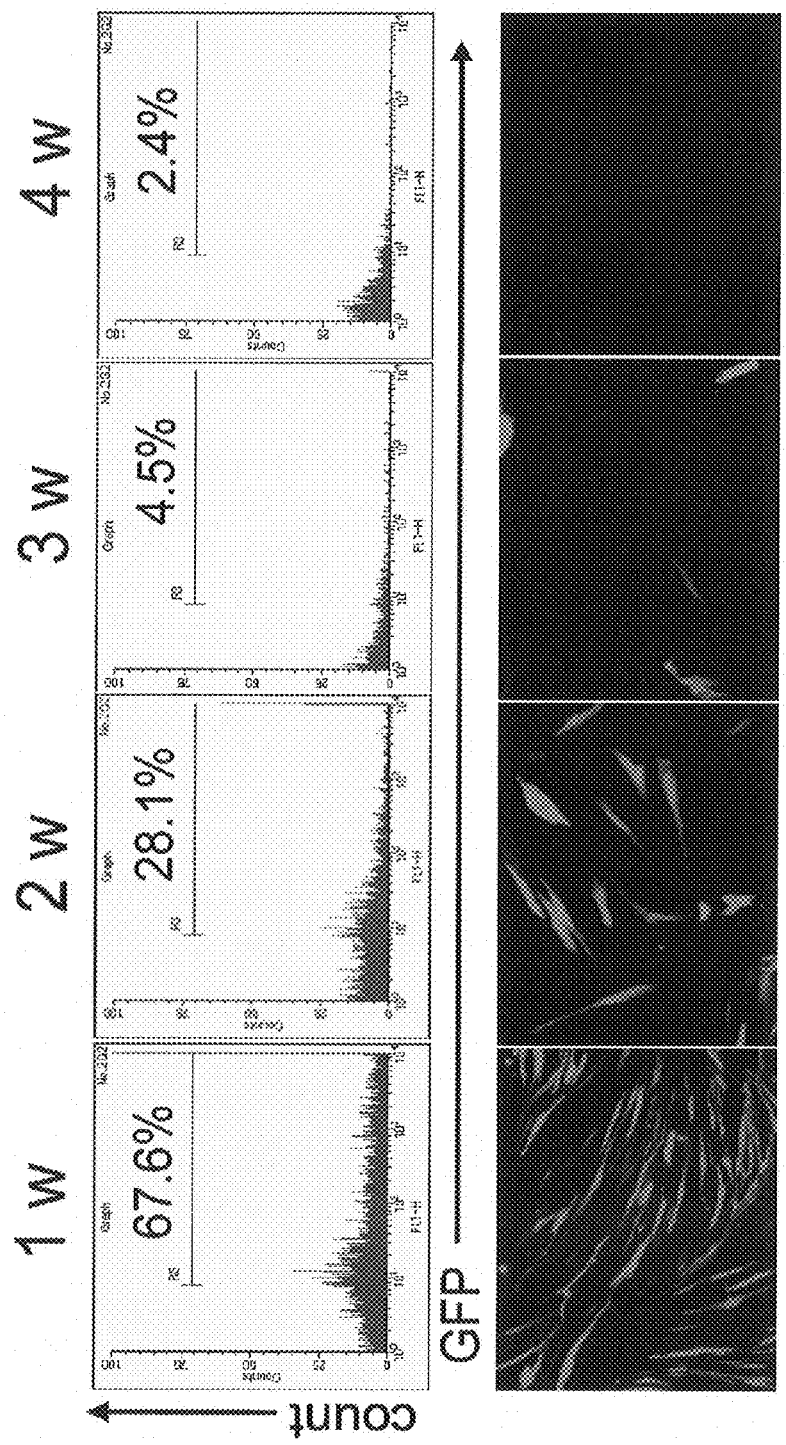
FIG. 18 shows results of weekly measurements of the amount expressed (fluorescence intensity) of EGFP transferred using an episomal vector. The upper panel: charts of fluorescence intensity analyzed by FACS. The axis of abscissas indicates fluorescence intensity; the axis of ordinate indicates the number of cells. Each % value in the chart indicates a ratio of GFP-positive cells. The lower panel: fluorescence photographs of cells (GFP-positive images).

In a preliminary study, pCXLE-EGFP was transferred to HDF, and an investigation was made to determine how the expression of EGFP disappeared. Every week from the 1st to 4th week after the transfer, the amount expressed (fluorescence intensity) of EGFP in $1 \times 10^4$ cells was analyzed by FACS. The results are shown in FIG. 18. The amount expressed of EGFP and the number of cells showing the expression decreased over weeks; 4 weeks after the transfection, GFP-positive cells had decreased to as low as 2.4%.

Subsequently, just after establishment by transfer of pCXLE-hOct4-shp53, pCXLE-hSK and pCXLE-hUL to HDF, 18 different iPS clones were examined for the presence or absence of exogenous genes.

A 0.2 mL tube containing 5 μL of a genome recovery buffer (the buffer for TaKaRa Ex Taq supplemented with 167 μg/mL proteinase K) was provided. On day 30 after transfection, colonies of each iPS cell were physically dissociated from the dish, and recovered in this tube. After the recovery, the tube was incubated at 55° C. for 3 hours to obtain a cell lysate. After adding 10 μL of $H_2O$, the lysate was heated at 95° C. for 3 minutes to inactivate the proteinase K. This was used as it was as a template for real-time PCR. The PCR was performed using SYBR Premix EX Taq II (Takara Shuzo). We designed a PCR primer pair for EBNA-1 to calculate the copy numbers of the episomal vectors, and another primer pair for the endogenous FBXO15 locus to estimate the cell number.

```
EBNA-1 primers (for detection of episomal alleles)
                                        (SEQ ID NO: 39)
EBNA-183F    ATC AGG GCC AAG ACA TAG AGA TG (SEQ ID NO: 40)
EBNA-243R    GCC AAT GCA ACT TGG ACG TT Fbx15 primers (for detection of endogenous alleles)
                                        (SEQ ID NO: 41)
hFbx15-2F    GCC AGG AGG TCT TCG CTG TA (SEQ ID NO: 42)
hFbx15-2R    AAT GCA CGG CTA GGG TCA AA
```

Figure 19:
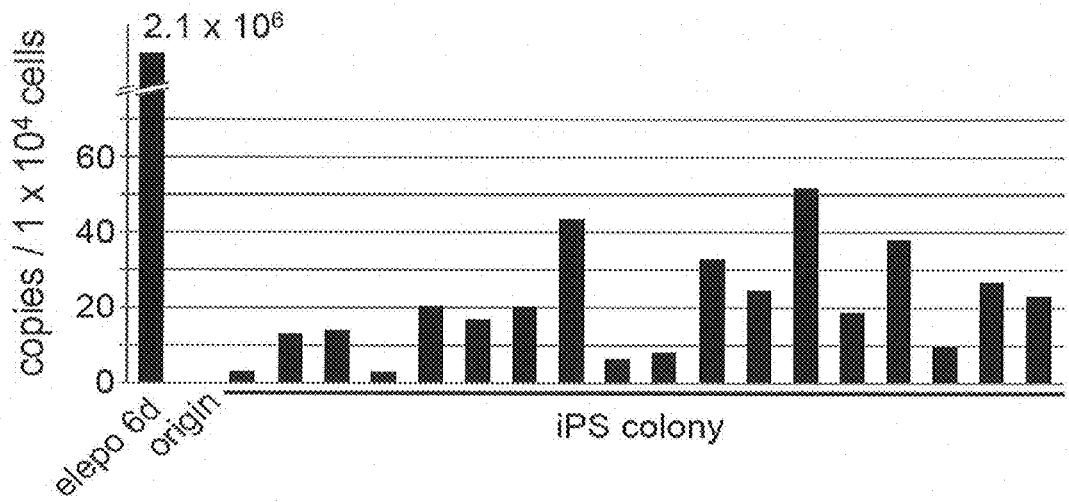
FIG. 19 is a graphic representation of results of an examination of 18 clones of established iPS cells for the number of copies of the episomal vector possessed thereby by real-time PCR. The axis of ordinate indicates the number of copies of episomal vectors per $1 \times 10^4$ cells. "elepo 6d" stands for cells on day 6 after reprogramming gene transfer, and "origin" for the HDF used for the transfer.

While the amount of EBNA-1 amplified was corrected by the cell count in the reaction mixture calculated from the amount of Fbx15 amplified, the number of copies of episomal vector per $1 \times 10^4$ cells was calculated. The results are shown in FIG. 19. The mean for the 18 clones was very low at 20.3±13.7 copies per $1 \times 10^4$ cells, demonstrating that only a very small amount of exogenous genes (episomal vectors) remained 30 days after the transfection.

Next, the same experiment was performed except that the cells were passage cultured.

We prepared fresh cell lysis solutions, which consisted of 1× Ex Taq buffer (Takara) and 167 μg/ml proteinase K. To analyze established iPS cells, cells cultured in 60-mm dishes were harvested with a cell scraper after removal of feeder cells with CTK treatment. The cells were placed into tubes and centrifuged, and the cell pellets were lysed with 200 μl of lysis solution. After incubation at 55° C. for 3 h followed by proteinase K inactivation at 95° C., the lysates were used for the quantitative PCR analysis. We used the pCXLE-hFbx15-cont2 plasmid, which has amplicon for both FBXO15 and EBNA-1, for standard amplification.

Figure 31:
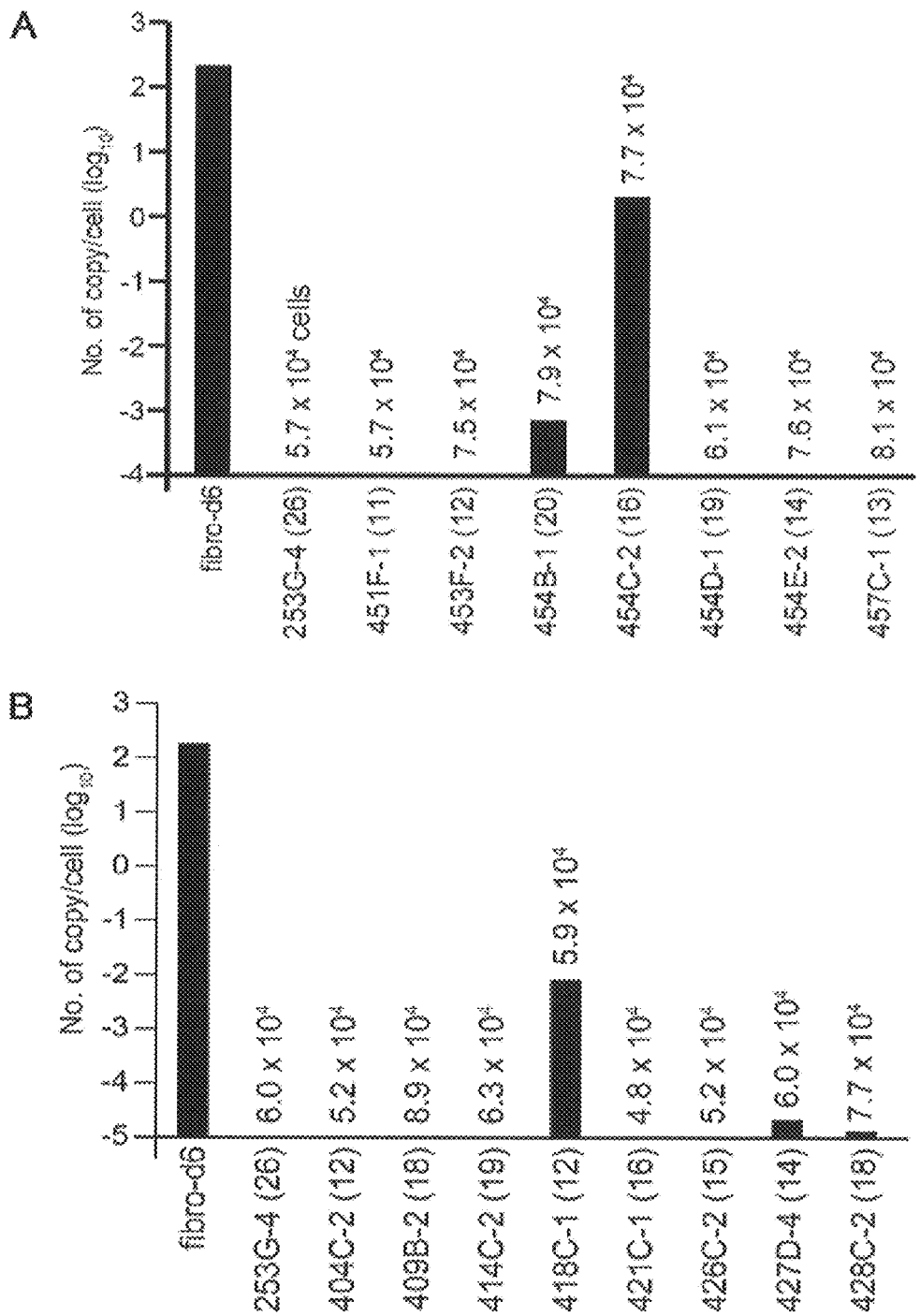
FIG. 31 shows copy numbers of episomal vectors remained in epi-iPSC clones. A: the results of DP-derived epi-iPS cells. B: the results of fibroblast-derived epi-iPS cells. Numbers in parentheses indicate the passage numbers of each clone. Also shown are the numbers of cells used for each clone. As a positive control, retrovirus-derived iPS clone (253G-4) and fibroblasts 6 days after electroporation of the Y4 mixture were analyzed (fibro-d6).

The results of DP-derived epi-iPS cells are shown in FIG. 31A. We detected approximately 200 copies of the episomal vectors per cell six days after transfection. In contrast, we were unable to detect any EBNA-1 DNA in five clones out of the seven tested. In the remaining two clones, we detected ~0.001 and 2 copies, respectively (FIG. 31A). The later clone is likely to have integration of the plasmid into a chromosome.

The results of fibroblast-derived epi-iPS cells are shown in FIG. 31B. In several clones, including 404C-2 and 409B-2, we were unable to detect any episomal vectors. These data demonstrated that in the majority of epi-iPSC clones, the episomal vectors were spontaneously lost.

Example 11

Confirmation of the Presence or Absence of Expression of Exogenous Genes in iPS Colonies At the 5th to 9th passage after being established by transferring pCXLE-hOct4-shp53, pCXLE-hSK and pCXLE-hUL to HDF, 9 different iPS clones were examined for the presence or absence of the expression of the exogenous genes.

Total RNA was extracted from the iPS cells in one well of a 6-well plate; 1 μg thereof, the primer dT (20) and the reverse transcriptase Rever Tra Ace (TOYOBO) were used to reverse-transcribe the mRNA to a complementary strand DNA. The final volume of the reaction product was 20 μL. Added to this reverse transcript was 60 μL of $H_2O$. Quantitative PCR was performed for each transgene with 1 μL of the reaction product (equivalent to 12.5 ng of RNA) as a template, and with SYBR Green II as an indicator, using the primer sets shown in Table 6 below, one for measuring the sum of the amount of exogenous genes expressed and the amount of endogenous genes expressed (total amount expressed), and the other for measuring the amount of exogenous genes expressed. The PCR amplification conditions used were as follows: 1 cycle at 95° C. for 30 seconds, followed by 50 cycles at 94° C. for 10 seconds, 60° C. for 10 seconds, and 72° C. for 30 seconds.

TABLE 6

| | | | |
|---|---|---|---|
| hOCT3/4 (total) | hOct3/4-S944 | #40-56 | CCC CAG GGC CCC ATT TTG GTA CC (SEQ ID NO: 43) |
| | hOct3/4-as | #10-25 | ACC TCA GTT TGA ATG CAT GGG AGA GC (SEQ ID NO: 44) |
| hOct3/4 (Tg) | hOCT4-1072F | #74-74 | CAT TCA AAC TGA GGT AAG GG (SEQ ID NO: 45) |
| | WPRE-70R | #74-73 | TAG CGT AAA AGG AGC AAC ATA G (SEQ ID NO: 46) |
| hKLF4 (total) | hKlf4-S1016 | #62-88 | ACC CAT CCT TCC TGC CCG ATC AGA (SEQ ID NO: 47) |
| | hKlf4-AS1048 | #43-94 | TTG GTA ATG GAG CGG CGG GAC TTG (SEQ ID NO: 48) |
| hKlf4 (Tg) | hKLF4-S1380 | #66-24 | cca cct cgc ctt aca cat gaa ga (SEQ ID NO: 49) |
| | WPRE-70R | #74-73 | TAG CGT AAA AGG AGC AAC ATA G (SEQ ID NO: 50) |

TABLE 6-continued

```
hSOX2 (total)   hSOX2-S875          #66-23 ttc aca tgt ccc agc act acc aga (SEQ ID NO: 51)
                HsSox2-AS           #31-72 TCA CAT GTG TGA GAG GGG CAG TGT GC (SEQ ID NO: 52)

hSox2 (Tg)      hSOX2-S875 (66-23)  #66-23 ttc aca tgt ccc agc act acc aga (SEQ ID NO: 53)
                FMDV-2A-R2          #74-72 TTT GTT TGA CAG GAG CGA CAA T (SEQ ID NO: 54)

hL-MYC (total)  hMYCL1-S1027        #71-59 GCG AAC CCA AGA CCC AGG CCT GCT CC (SEQ ID NO: 55)
                hMYCL1-AS1145       #71-60 CAG GGG GTC TGC TCG CAC CGT GAT G (SEQ ID NO: 56)

hLMyc (Tg)      hLMyc-1005F         #74-76 GGC TGA GAA GAG GAT GGC TAC (SEQ ID NO: 57)
                FMDV-2A-R2          #74-72 TTT GTT TGA CAG GAG CGA CAA T (SEQ ID NO: 58)

hLin28 (total)  hLin28 S502         #49-64 AGCCATATGGTAGCCTCATGTCCGC (SEQ ID NO: 59)
                hLIN28-AS           #47-6  TCA ATT CTG TGC CTC CGG GAG CAG GGT AGG (SEQ ID NO: 60)

hLin28 (Tg)     hLin28 S502         #49-64 AGCCATATGGTAGCCTCATGTCCGC (SEQ ID NO: 61)
                WPRE-70R            #74-73 TAG CGT AAA AGG AGC AAC ATA G (SEQ ID NO: 62)
```

Figure 20:
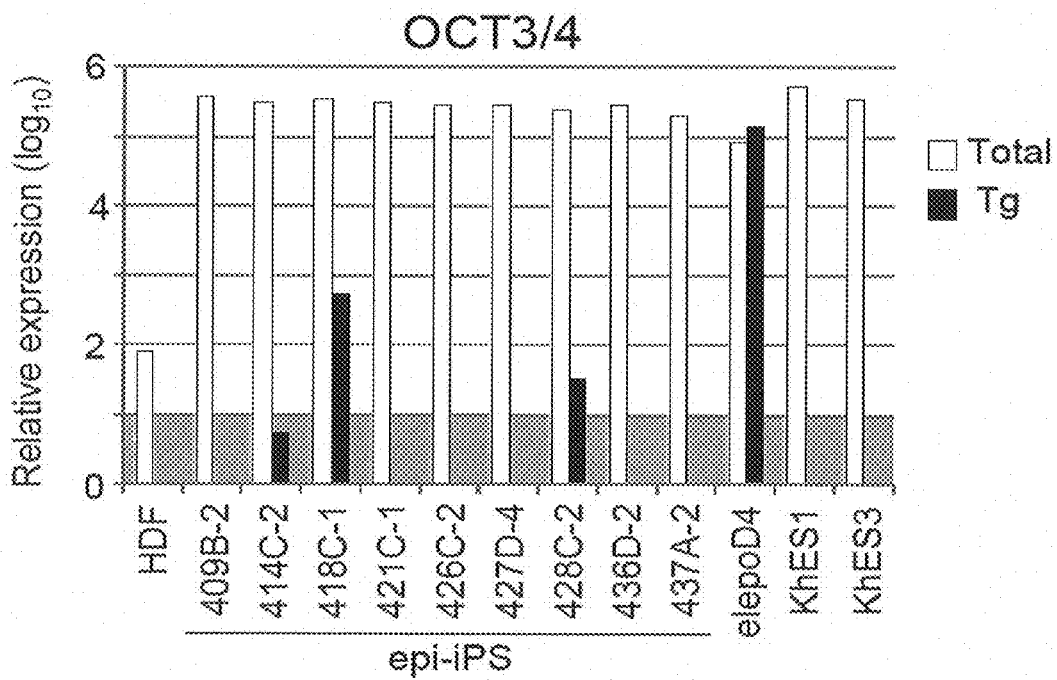
FIG. 20 is a graphic representation of results of an examination of the amount of Oct3/4 expressed in 9 clones of established iPS cells by quantitative PCR. The outlined bar indicates the sum of the amounts of exogenous and endogenous genes expressed (total amount expressed), and the solid bar indicates the amount of exogenous genes expressed.
Figure 21:
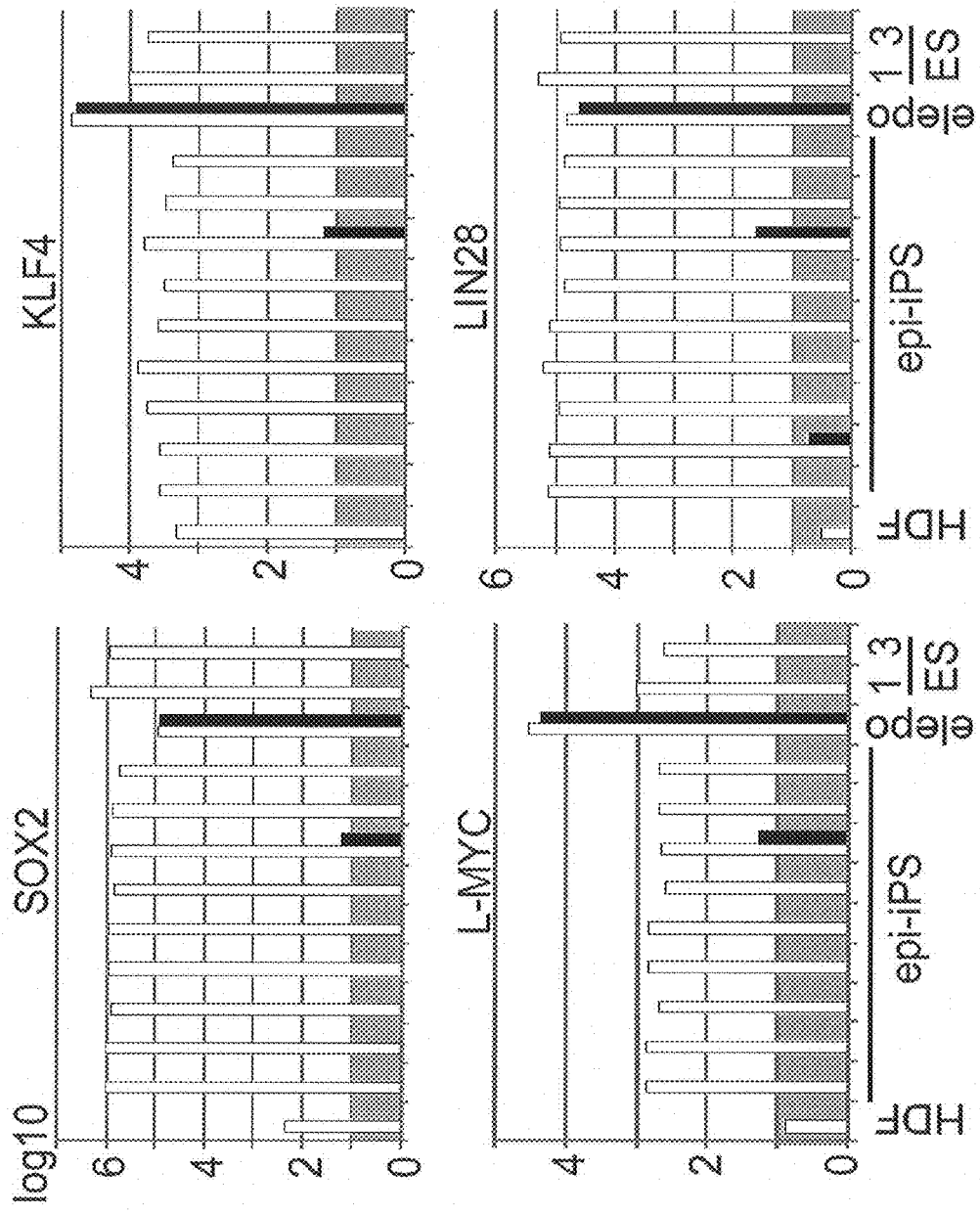
FIG. 21 is a graphic representation of results of the same experiment as FIG. 20 performed on Sox2, Klf4, L-Myc and Lin28.

Next, each of pCXLE-hOct4-shp53, pCXLE-hSK and pCXLE-hUL, which had been used for the transfection, was prepared as a $10^6$ copies/μL solution, and this solution was serially diluted 10-fold. With each starting solution and serial dilution as templates, quantitative PCR was performed in the same manner. For each reprogramming gene, a standard curve was generated for each of the primer set for measuring the total amount expressed and the primer set for measuring the amount of exogenous genes expressed. The results of quantitative PCR for each iPS cell were converted using this standard curve, and the number of copies of each gene per 12.5 ng of total RNA was calculated as the total amount expressed and the amount of exogenous genes expressed. Logarithmic plots of this number of copies on the axis of ordinates are shown in FIG. 20 (Oct3/4) and FIG. 21 (Sox2, Klf4, L-Myc, Lin28) (the grey zone indicates values under the limit of detection). A large number of clones, including 409B-2 and 421C-1, were observed in which the expression level was under the limit of detection for all exogenous genes examined. It was shown that choosing these cells allows utilization of safer iPS cells.

Example 12

Characterization of Human Epi-iPS Cells

1) Microarray Analysis and CGH Array Analysis

To determine whether the gene expression pattern differed among the human iPS cells established by transferring pCXLE-hOct4-shp53, pCXLE-hSK and pCXLE-hUL to dermal fibroblasts (TIG and HDF), human ES cells, and the TIG and HDF used for the transfer, DNA microarray analysis was performed as described in Cell, 131, 861-872 (2007). The correlation coefficients between the various cells are shown in Table 7.

TABLE 7

| Array Name | 409B-2 (p7) | 418C-1 (p7) | 421C-1 (p7) | 426C-2 (p9) | 428C-2 (p7) | KhES1 (7-5-4-5-4) | KhES3 (4-9-4-4-4) | KhES3 (4-9-4-4-4) | TIG107-Slc | TIG120-Slc | HDF1388-Slc |
|---|---|---|---|---|---|---|---|---|---|---|---|
| 409B-2 (p7) | 1.000000 | 0.988557 | 0.982883 | 0.982627 | 0.984413 | 0.974758 | 0.984130 | 0.984364 | 0.787134 | 0.792555 | 0.820612 |
| 418C-1 (p7) | 0.988557 | 1.000000 | 0.980910 | 0.981387 | 0.984424 | 0.970780 | 0.982916 | 0.982731 | 0.796518 | 0.800264 | 0.827104 |
| 421C-1 (p7) | 0.982883 | 0.980910 | 1.000000 | 0.988431 | 0.980966 | 0.978521 | 0.985702 | 0.984871 | 0.795027 | 0.801948 | 0.824806 |
| 426C-2 (p9) | 0.982627 | 0.981387 | 0.988431 | 1.000000 | 0.983527 | 0.980344 | 0.988320 | 0.988782 | 0.797564 | 0.803897 | 0.832218 |
| 428C-2 (p7) | 0.984413 | 0.984424 | 0.980966 | 0.983527 | 1.000000 | 0.972649 | 0.982585 | 0.983471 | 0.792073 | 0.796452 | 0.820714 |
| KhES1 (7-5-4-5-4) | 0.974758 | 0.970780 | 0.978521 | 0.980344 | 0.972649 | 1.000000 | 0.983036 | 0.983429 | 0.780730 | 0.788327 | 0.813383 |
| KhES3 (4-9-4-4-4) | 0.984130 | 0.982916 | 0.985702 | 0.988320 | 0.982585 | 0.983036 | 1.000000 | 0.993120 | 0.783260 | 0.790745 | 0.821393 |
| KhES3 (4-9-4-4-4) | 0.984364 | 0.982731 | 0.984871 | 0.988782 | 0.983471 | 0.983429 | 0.993120 | 1.000000 | 0.787711 | 0.795464 | 0.820877 |
| TIG107-Slc | 0.787134 | 0.796518 | 0.795027 | 0.797564 | 0.792073 | 0.780730 | 0.783260 | 0.787711 | 1.000000 | 0.986470 | 0.892890 |
| TIG120-Slc | 0.792555 | 0.800264 | 0.801948 | 0.803897 | 0.796452 | 0.788327 | 0.790745 | 0.795464 | 0.986470 | 1.000000 | 0.887098 |
| HDF1388-Slc | 0.820612 | 0.827104 | 0.824806 | 0.832218 | 0.820714 | 0.813383 | 0.821393 | 0.820877 | 0.892890 | 0.887098 | 1.000000 |

Figure 22:
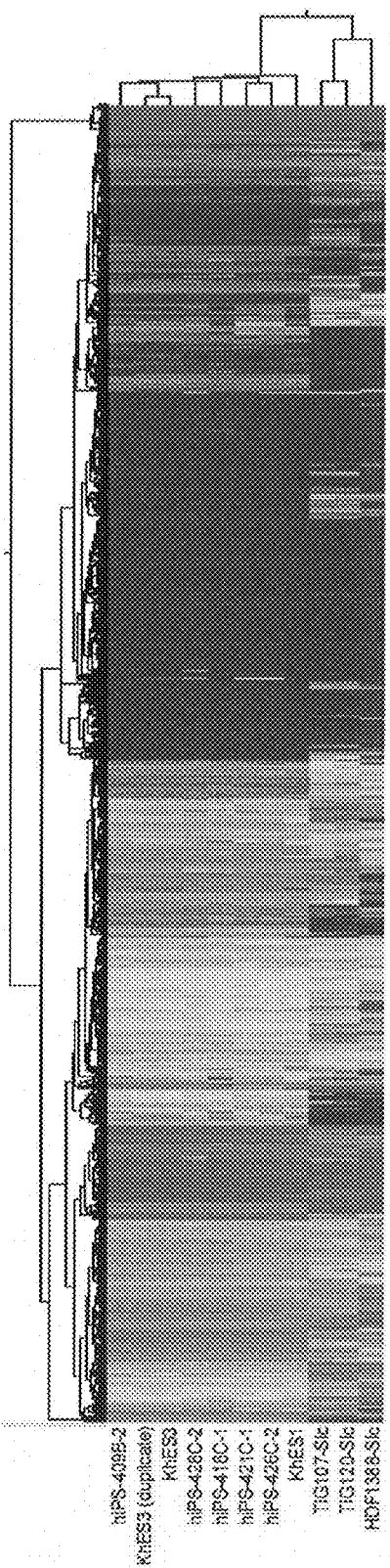
FIG. 22 shows results of a clustering analysis based on differences in the amount expressed of each gene by DNA microarray analysis on human iPS cells established from dermal fibroblasts (TIG and HDF), the starting TIG and HDF, and human ES cells.
Figure 23:
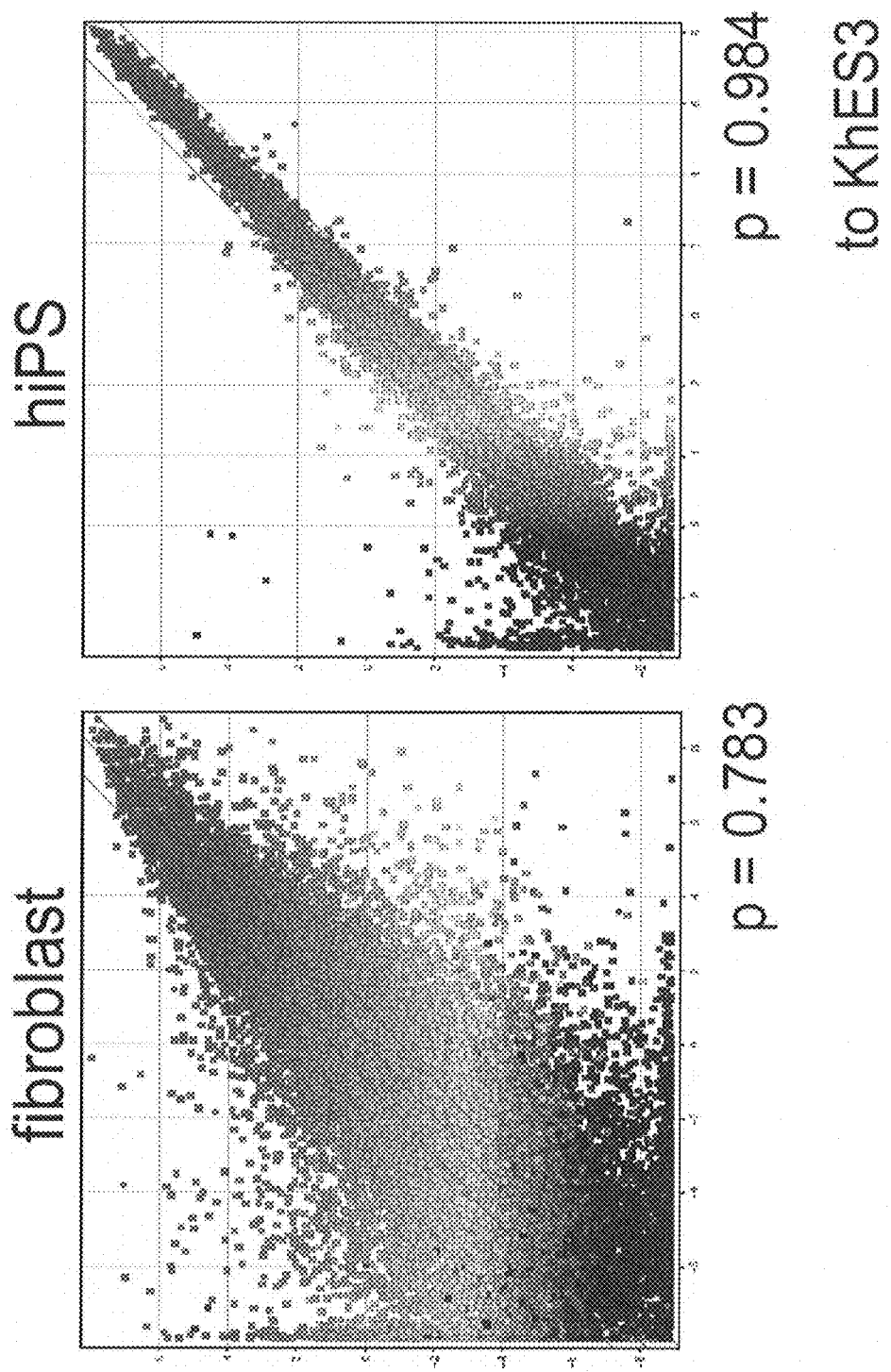
FIG. 23 shows scatter plots of the results of the DNA microarray analysis, performed to determine whether the gene expression pattern differs between a human ES cell (KhES3) and HDF (left chart), or a human ES cell (KhES3) and a human iPS cell established using an episomal vector (right chart).

Results of a clustering analysis based on differences in the amount expressed among various genes are shown in FIG. 22. Results of scatter plot analysis are shown in FIG. 23. The iPS cells established using an episomal vector exhibited an expression pattern similar to that of ES cells, and were therefore proven to be iPS cells similar to ES cells.

Figure 24:
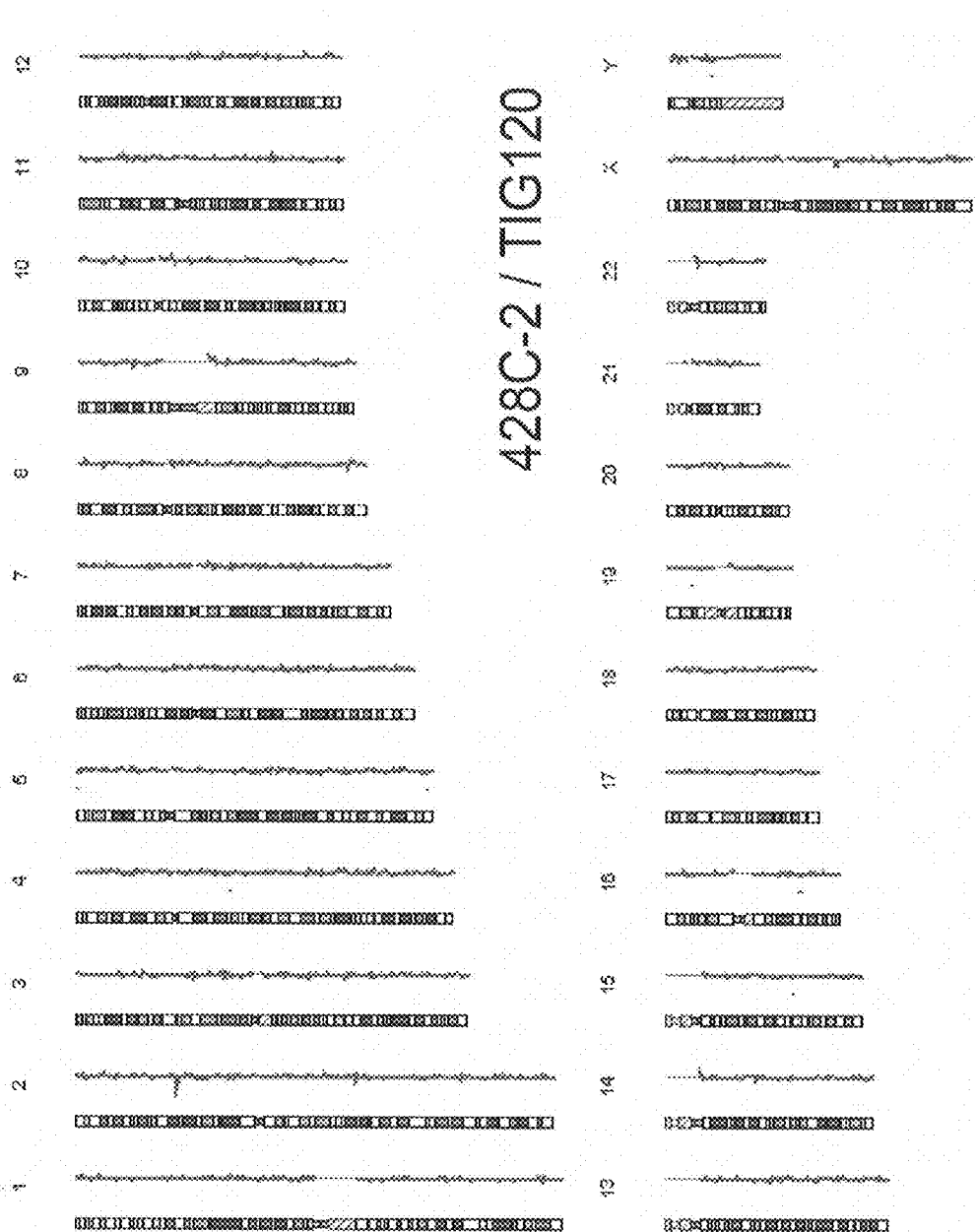
FIG. 24 shows results of CGH array analysis of the human iPS cell established using the episomal vector. The data are shown as variation against the TIG cells used for the transfection (TIG120).

Results of CGH array analysis are shown in FIG. 24. A comparison with the TIG cell used for the transfer showed no major abnormalities. A karyotype analysis by G band staining on some cells revealed no abnormal findings.

In the experiments described above, the following arrays and scanner were used:
Array for human GE: G4112F Whole Human Genome Microarray Kit, 4×44K (Agilent)
Array for human CGH: G4426B#14950 Human Genome CGH Microarray Kit 4×44K (Agilent)
Scanner: DNA Microarray Scanner, Model G2539A 2) RT-PCR Analyses We examined the expression of pluripotent stem cell markers, such as OCT3/4, SOX2, NANOG, and ESG1, in the epi-iPS cells. The results of DP-derived epi-iPS cells are shown in FIG. 32A, and the results of fibroblast-derived epi-iPS cells are shown in FIG. 32B. The RT-PCR analyses revealed that epi-iPSC clones express these genes at levels comparable to those in hESCs and retrovirus-derived iPSC clones.

3) Bisulfite Sequencing

Genomic DNA was extracted from iPS cells after removing feeder cells, and was analyzed as described previously (K. Takahashi et al, Cell 131, 861 (Nov. 30, 2007)).

Figure 33:
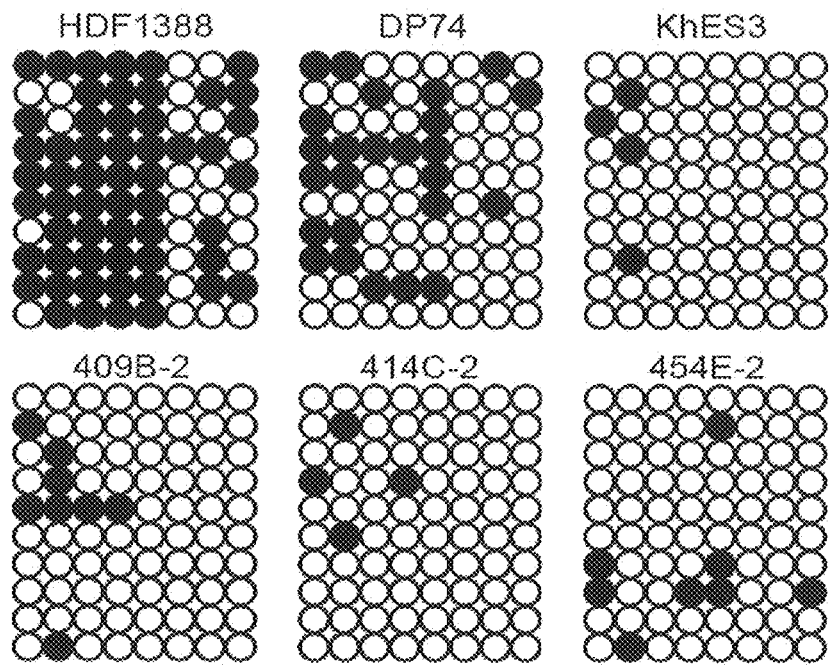
FIG. 33 shows DNA methylation status of the NANOG promoter region. Open and closed circles indicate unmethylated and methylated CpG, respectively.

The DNA methylation levels of CpG sites in the promoter region of NANOG were high in parental HDF and DP cells, but were low in epi-iPS and ES cells (FIG. 33).

4) Teratoma Formation

Figure 34A:
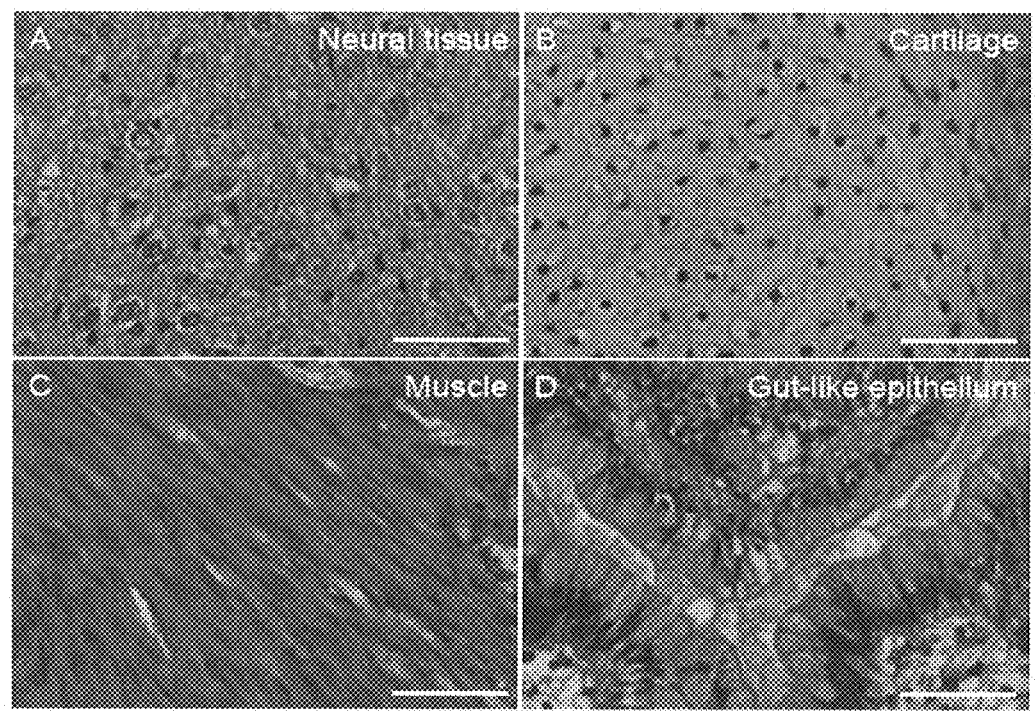
FIG. 34A: the results of 454E-2. Shown are the hematoxylin and eosin staining of neural tissue (A), cartilage (B), muscle (C), and gut-like epithelia (D). Scale bars=50 µm.
Figure 34B:
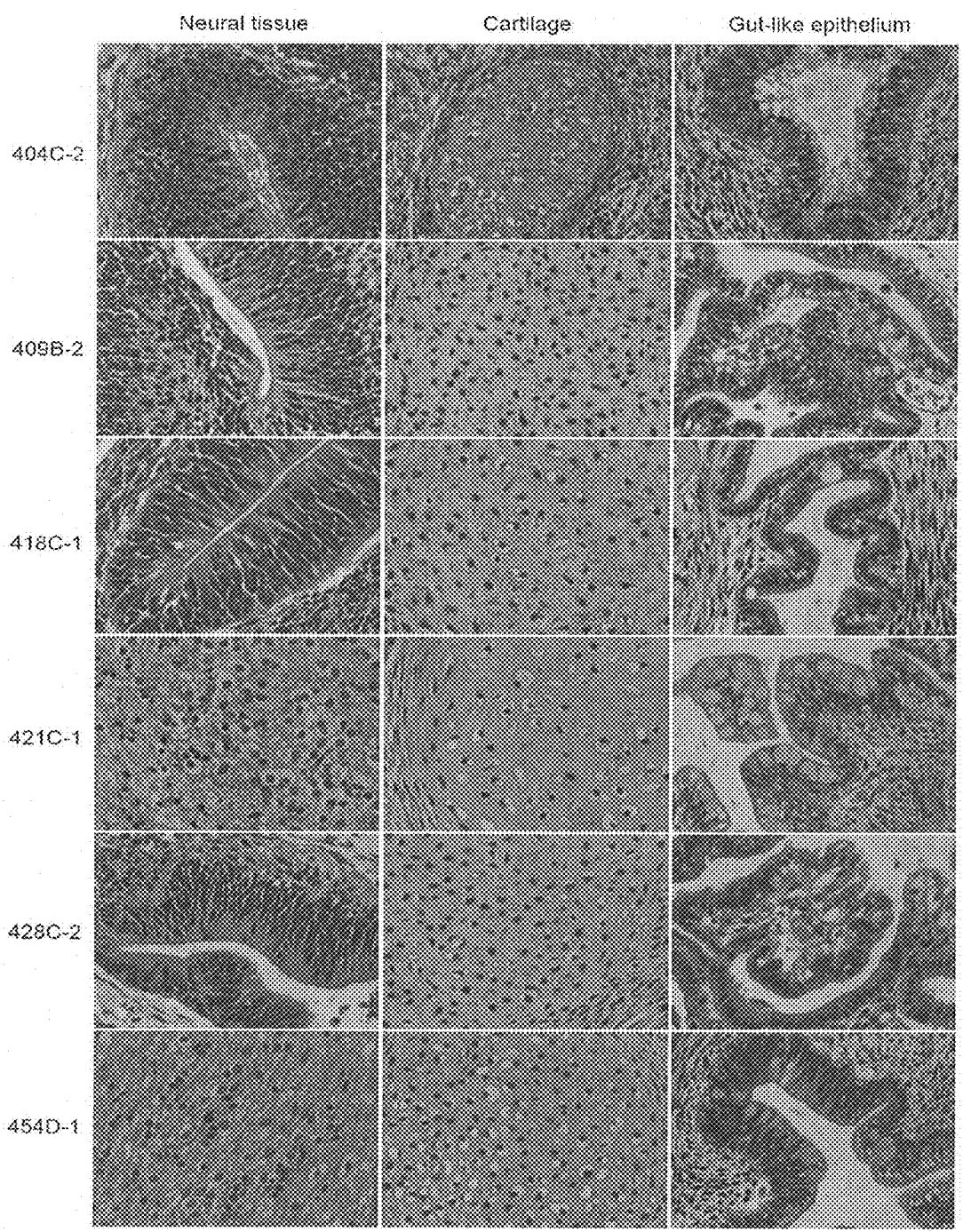
FIG. 34B: the results of 404C-2, 409B-2, 418C-1, 421C-1, 428C-2 and 454D-1. Shown are the hematoxylin and eosin staining of neural tissue, cartilage, and gut-like epithelia. Scale bar (bottom-right corner)=50 µm.

We examined the differentiation potential of epi-iPSCs in vivo. The cells were harvested with the CTK solution and centrifuged. The cell pellets were resuspended in DMEM/F12. Half of the cells from a confluent 60-mm dish were injected into the testis of a SCID mouse (CREA, Japan). From 8 to 12 weeks after injection, tumors were dissected, and were fixed with 4% paraformaldehyde in PBS. Paraffin-embedded tissues were sectioned and stained with hematoxylin and eosin. The results are shown in FIG. 34. Histological examaination confirmed that these tumors were teratomas and contained tissues of all three germ layers, including neural epithelium, cartilage, muscle, and gut-like epithelium (FIG. 34A, B).

5) In Vitro Differentiation

In vitro-directed differentiation into dopaminagic neurons was carried out using the serum-free culture of embryoid body-like aggregates (SFEB) method combined with double SMAD inhibition by a BMP antagonist and an Activin/Nodal inhibitor (M. Eiraku et al, *Cell Stem Cell* 3, 519 (2008)).

For the induction of dopaminegic neurons, differentiation medium was prepared as follows: DMEM/F12 supplemented with 5% Knockout Serum Replacement (KSR; Invitrogen), 2 mM glutamine, 0.1 mM nonessential amino acids, and 0.1 mM 2-mercaptoethanol. iPS cells were dissociated into single cells in Accumax (Invitrogen) and quickly re-aggregated in the differentiation medium supplemented with 10 μM Y-27632, 2 μM dorsomorphin, and 10 μm SB431542 (Sigma) at a density of 9000 cells/150 μl/well using 96-well low cell-adhesion plates (LIPIDURE-COAT PLATE A-U96, NOF Corporation). After 5 days of cultivation, cell aggregates were stimulated with 100 ng/ml FGF-8 and 20 ng/ml Wnt1. From day 8, 200 ng/ml SHH was present to the medium. On day 12, the aggregated cells were collected and transferred to a 60 mm poly-ornithine/laminin-coated dish in NB medium (Neurobasal medium containing B27 supplement; Invitrogen) with 200 ng/ml SHH. Thereafter, the medium was changed to NB medium supplemented with 1 ng/ml FGF-20 and 12.5 ng/ml bFGF on day 15. The cells were harvested on day 22 and seeded onto 8-well chamber plates at a density of $2 \times 10^5$ per well in NB medium supplemented with 2 ng/ml GDNF, 20 ng/ml BDNF, 400 μM dbcAMP, and 200 μM ascorbic acid. Differentiated cells were fixed for the immunostaining analyses on day 29. We used primary antibodies for Nestin (Chemicon), Ki67 (Novocastra), Pax6 (Covance), betaIII-tubulin (Covance Research Products), tyrosine hydroxylase (Chemicon), MAP2ab (Sigma), and VAMT-2 (PelFreeze). Secondary antibodies conjugated with Alexa488, Alexa594, or Cy5 were used as appropriate. To visualize nuclei, 200 ng/ml of 4',6'-diamidino-2-phenylindole (DAPI) was added to the final wash.

Figure 35A:
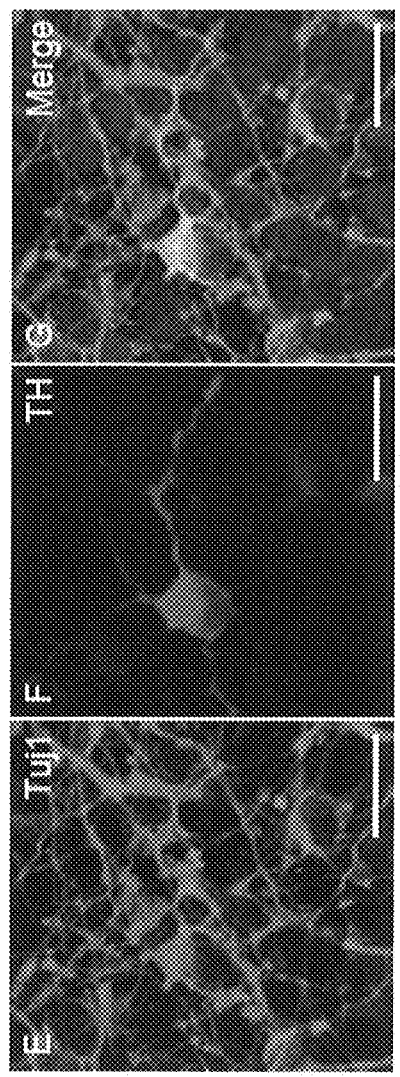
FIG. 35A: Shown are the immunostaining images for Tuj1 (green, E), TH (red, F), and a merged image with nuclear staining using Hoechst 33342 (blue, G). Scale bars=20 µm.
Figure 35B:
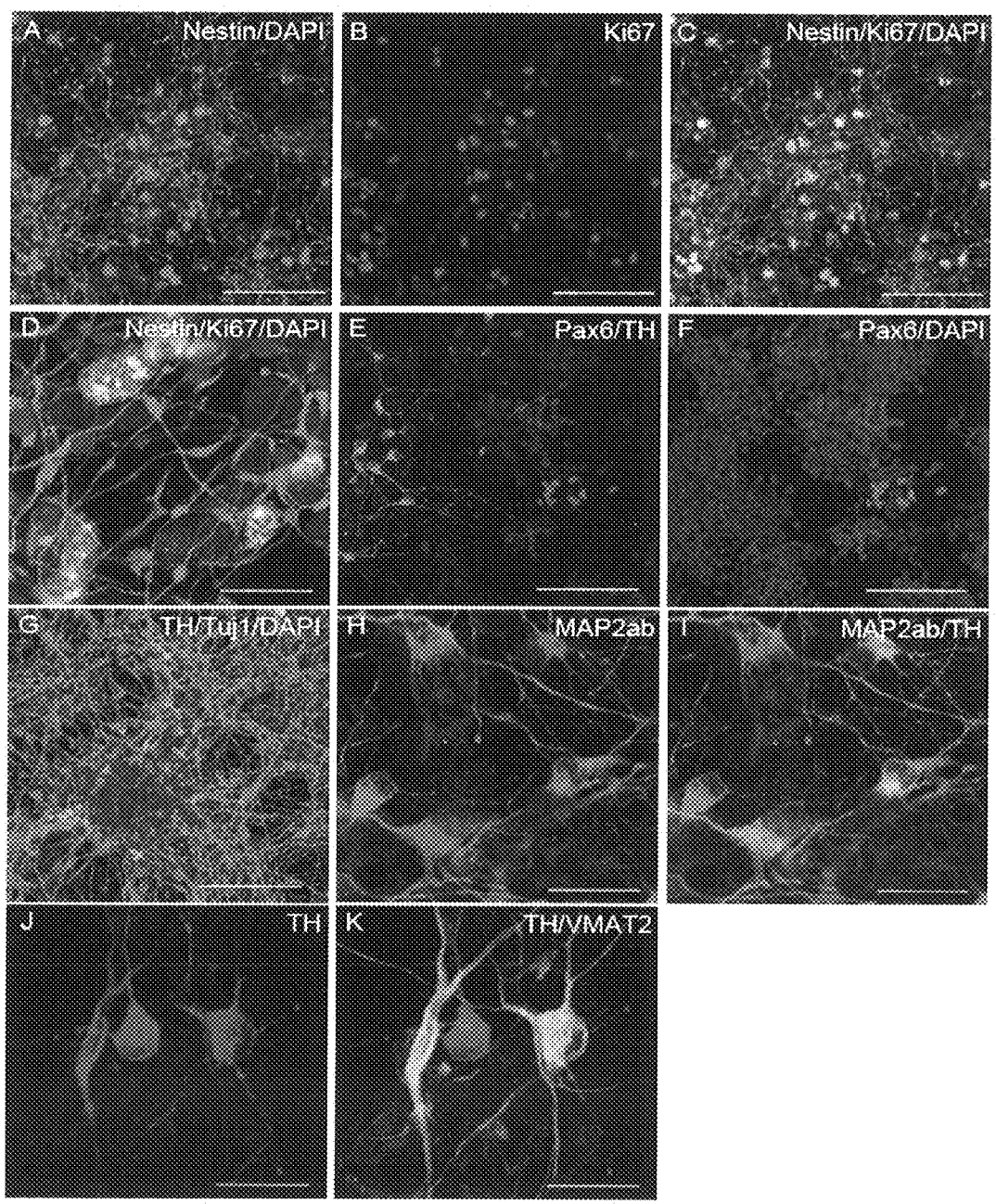
FIG. 35B: (A-C) Double immunostaining for Nestin (green) and Ki67 (red) with DAPI nuclear staining (blue). A high magnification image is shown in (D). (E and F) Double immunostaining for Pax6 (red) and TH (green). (G) Double immunostaining for TH (red) and TuJ1 (green) with DAPI. (H and I) Double immunostaining for TH (red) and MAP2ab (green). (J and K) Double immunostaining for TH (Red) and the vesicular monoamine transporter 2 (VMAT2, green). Scale bars: 100 µm in (A-C, E-G); 20 µm in (D, H-K).

The results are shown in FIG. 35. The majority of cells expressed the immature neural marker Nestin (FIG. 35B-A). Some of the cells were still proliferating and were positive for Ki67 (FIG. 35B-B,C,D). Clusters of immature neural cells were positive for Pax6, while more mature cell clusters expressed a marker of dopaminergic neurons, tyrosine hydroxylase (TH), following treatment with inducing factors, such as SHH and FGF8 (FIG. 35B-E, 35B-F). TH-positive cells also colocalized with the neural markers Tuj1 and MAP2ab, and the dopamine transporter VMAT2 (FIG. 35A-E,F,G, 35B-G,H,I,J,K). Therefore, epi-iPSCs have the potential to differentiate into dopaminergic neurons. The epi-iPSCs established by the use of the Y3 mixture (pCXLE-hOct4, pCXLE-hSK, pCXLE-hUL) were also subjected to a similar analysis (RT-PCR, Copy number analysis, karyotyping and Teratoma formation). As a result, epi-iPSCs were confirmed to be comparable to epi-iPSCs established by the use of the Y4 mixture (pCXLE-hOct4-shp53, pCXLE-hSK, pCXLE-hUL). The analysis list of respective epi-iPSC clones is shown in Table 8.

TABLE 8

Epi-iPS clone list.

| Clone | Source | | | | | Gene expression | | | Copy number analysis | Karyo-typing | HLA | STR | Differentiation | | |
|---|---|---|---|---|---|---|---|---|---|---|---|---|---|---|---|
| | Origin | Age | Sex | Race | Factors | RT-PCR | Micro-array | Bisulfite | | | | | Teratoma | Dopa | RPE |
| 404C-2 | HDF1388 | 36 | F | C | Y4 | ✓ | ✓ | | ✓ | | | | ✓ | ✓ | ✓ |
| 409B-2 | HDF1388 | 36 | F | C | Y4 | ✓ | ✓ | ✓ | ✓ | ✓ | ✓ | ✓ | ✓ | ✓ | ✓ |
| 414C-2 | HDF1388 | 36 | F | C | Y4 | ✓ | ✓ | ✓ | ✓ | ✓ | | ✓ | | ✓ | ✓ |
| 418C-1 | TIG114 | 36 | M | J | Y4 | ✓ | | | ✓ | ✓ | | | ✓ | | |
| 421C-1 | TIG107 | 81 | F | J | Y4 | ✓ | | | ✓ | ✓ | | | ✓ | | |
| 426C-2 | HDF1554 | 77 | F | C | Y4 | ✓ | | | ✓ | ✓ | | | | | |

TABLE 8-continued

Epi-iPS clone list.

| Clone | Source | | | | | Gene expression | | | Copy number analysis | Karyo-typing | HLA | STR | Differentiation | | |
| | Origin | Age | Sex | Race | Factors | RT-PCR | Micro-array | Bisulfite | | | | | Teratoma | Dopa | RPE |
|---|---|---|---|---|---|---|---|---|---|---|---|---|---|---|---|
| 427D-4 | HDF1437 | 56 | M | C | Y4 | ✓ | | | ✓ | ✓ | | | | | |
| 428C-2 | TIG120 | 6 | F | J | Y4 | ✓ | | | ✓ | ✓ | | | ✓ | | |
| 451F-3 | DP74 | 16 | F | | Y4 | ✓ | ✓ | | ✓ | ✓ | | | | ✓ | ✓ |
| 453F-2 | DP94 | 16 | F | | Y4 | ✓ | | | ✓ | ✓ | ✓ | | | | |
| 454B-1 | DP74 | 16 | F | | Y1 | ✓ | ✓ | | ✓ | ✓ | | | | | |
| 454C-2 | DP74 | 16 | F | | Y2 | ✓ | | | ✓ | ✓ | | | | | |
| 454D-1 | DP74 | 16 | F | | Y3 | ✓ | | | ✓ | ✓ | | | ✓ | | |
| 454E-2 | DP74 | 16 | F | | Y4 | ✓ | ✓ | ✓ | ✓ | ✓ | ✓ | ✓ | ✓ | ✓ | ✓ |
| 454F-1 | DP74 | 16 | F | | T2 | | | | | ✓ | | | | | |
| 457C-1 | DP74 | 16 | F | | Y4 | ✓ | ✓ | | ✓ | ✓ | ✓ | ✓ | | ✓ | ND |

ND, we could not detect RPE differentiation in our differentiation protocol (N = 1).

Example 13

Establishment and Cultivation of iPS Cells Under Xeno-Free Conditions (in the Absence of Heterologous Ingredients)

In utilizing iPS cells established using an episomal vector in the field of regenerative medicine, a key resides in the establishment and maintenance of iPS cells under xeno-free conditions. Hence, investigations were made as described below.

1) Use of Dental Pulp Stem Cell Line as Feeder Cells

Figure 25:
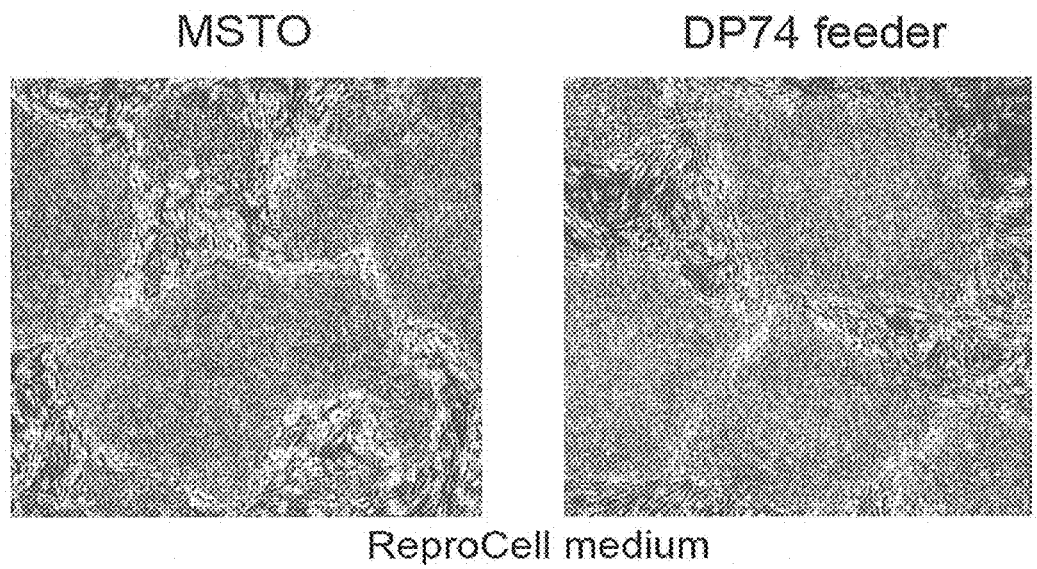
FIG. 25 is a photographic representation showing the morphology of cells as of the 1st passage obtained by culturing an iPS cell established using an episomal vector with the DP74 line used as feeder cells, using the ReproCELL medium (right). The left plate shows a photograph obtained with the use of MSTO as feeder cells.

It is known that a human iPS cell can be established and maintained even when a human dermal fibroblast (HDF) that has been used for transfection is used as feeder cells [Takahashi et al., PLoSone, vol. 4, issue 12, e8067 (2009)]. This is highly significant in considering clinical applications because the use of autologous feeder cells enables the maintenance of iPS cells under xeno-free conditions. Hence, an investigation was made to determine whether the dental pulp stem cell line DP74 could serve as feeder cells. The iPS cell used was a human iPS cell established by transferring pCXLE-hOct4-shp53, pCXLE-hSK and pCXLE-hUL to HDF. The culture broth used was a medium prepared by adding bFGF (Wako) to an ordinary primate ES cell culture medium (ReproCELL) at 4 ng/mL (hereinafter ReproCELL medium). Photographs of cells after 1 passage are shown in FIG. 25. The ES-like morphology was maintained to an equivalent extent compared with the use of MSTO as feeder cells.

2) Maintenance of iPS Cells Under Xeno-Free Conditions (1)

Figure 26:
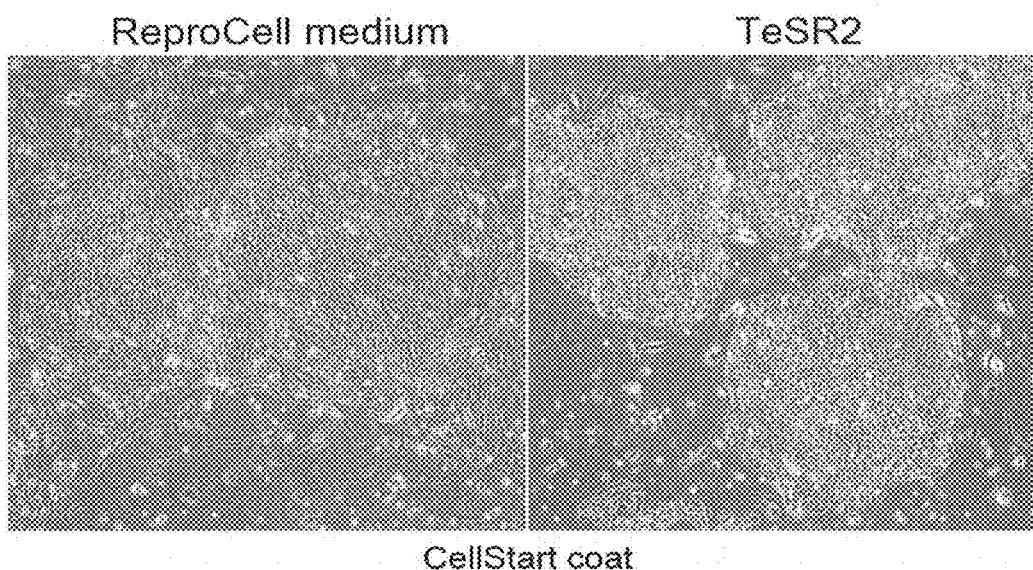
FIG. 26 is a photographic representation showing the morphology of cells as of the 1st passage obtained by culturing an iPS cell established using an episomal vector under Xeno-free conditions (Xeno-free medium used, and no feeder cells used). The left plate shows a photograph obtained with the use of the ordinary ReproCELL medium.

An investigation was made to determine whether iPS cells could be maintained under completely xeno-free conditions using the xeno-free medium TeSR2 (Stemcell Technologies) and the xeno-free plate coating agent CELLstart (GIBCO) (no feeder cells used). The iPS cell used was a human iPS cell established by transferring pCXLE-hOct4-shp53, pCXLE-hSK and pCXLE-hUL to HDF. Photographs of cells after 1 passage are shown in FIG. 26. When the ReproCELL medium was used, the cells began to change their morphology, whereas when TeSR2 was used, the cells maintained the undifferentiated morphology.

3) Maintenance of iPS Cells Under Xeno-Free Conditions (2)

An investigation was made to determine whether iPS cells could be maintained using the xeno-free medium TeSR2 (Stemcell Technologies) and KSR-XF [KnockOut DMEM (Invitrogen) supplemented with 15% KnockOut SR XenoFree (Invitrogen), 2 mM GlutaMAX-I (Invitrogen), 0.1 mM non-essential amino acids (Invitrogen), 0.1 mM 2-mercaptoethanol (Invitrogen) and 8 ng/mL bFGF (Wako)], with the DP74 line as feeder cells. The iPS cell used was a human iPS cell established by transferring pCXLE-hOct4-shp53, pCXLE-hSK and pCXLE-hUL to HDF. Photographs of cells after 1 passage are shown in FIG. 27. Whichever xeno-free media were used, the ES-like morphology was maintained.

Example 14

Transfection Under Xeno-Free Conditions

An investigation was made to determine whether xeno-free conditions serve the purpose not only after iPS cell establishment, but also before iPS cell establishment, i.e., at the time of reprogramming gene transfer to a somatic cell.

In a preliminary study, pCXLE-EGFP was transferred to DP74 using Microporator. The xeno-free medium used was StemPro MSC-SFM (Invitrogen).

Figure 28:
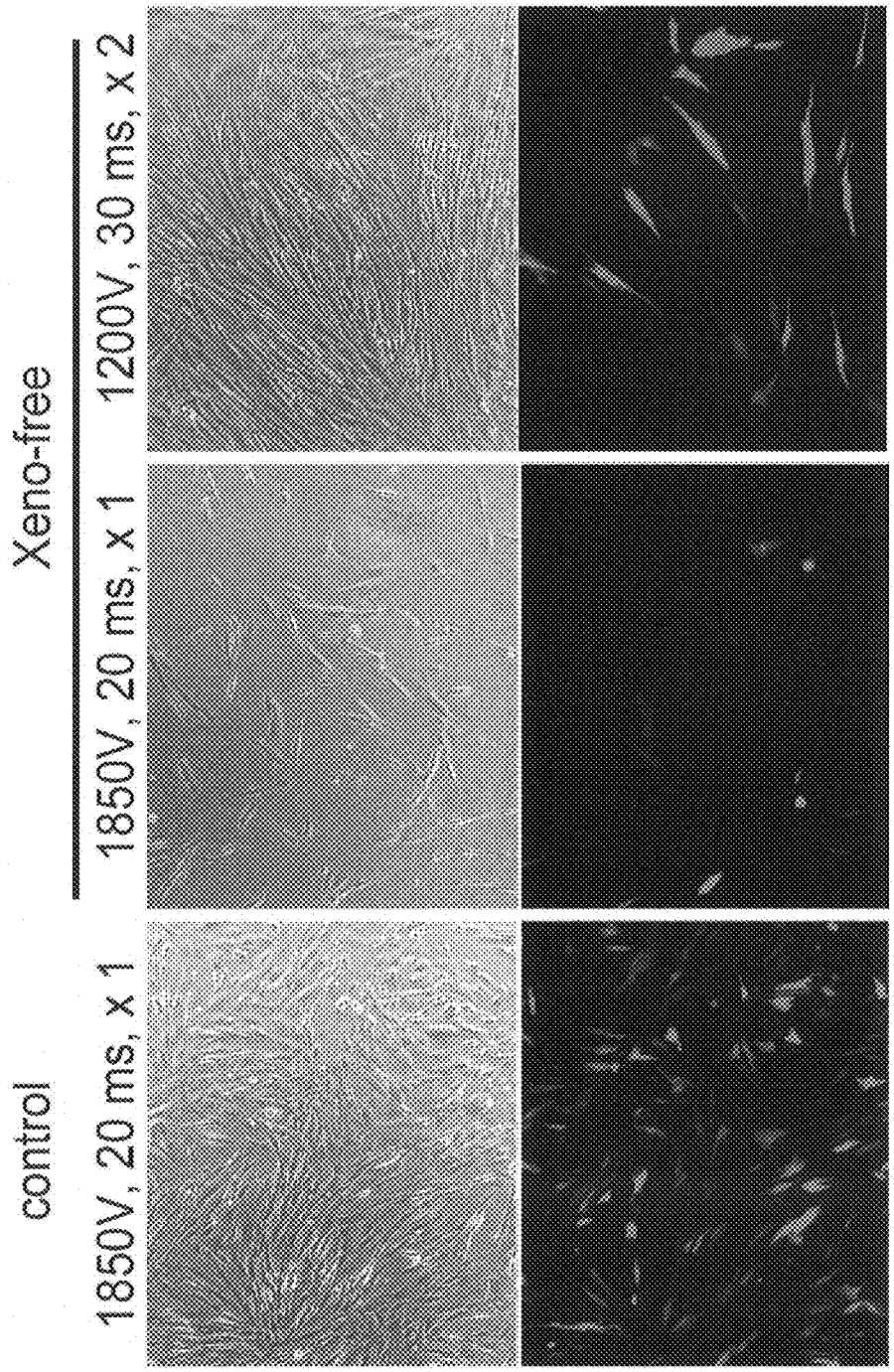
FIG. 28 shows results of transfer of pCXLE-EGFP to DP74 under Xeno-free conditions. Shown on the left side are the results of transfer under ordinary conditions (control). Upper panels: phase contrast images, lower panels: GFP observation images.

DP74 was cultured and maintained at 37° C. in the presence of 5% $CO_2$ in a CELLstart-coated 100 mm culture dish using StemPro MSC-SFM (Invitrogen) as a culture broth. At the time of transfer of pCXLE-EGFP, the medium was removed, and the cells were washed by the addition of 5 mL of PBS. After removing the PBS, the xeno-free cell dissociation solution TripLE select (Invitrogen) was added, and a reaction was carried out at 37° C. for about 5 minutes. After the cells rose, StemPro MSC-SFM was added to suspend the cells, and the cells were recovered in a 15 mL centrifugal tube. The suspension was centrifuged at 800 rpm for 5 minutes, and the supernatant was removed. After the cells were again suspended in StemPro MSC-SFM, $6 \times 10^5$ cells were recovered in a 1.5 mL tube. The suspension was centrifuged at 800 rpm for 5 minutes, and the supernatant was removed. pCXLE-EGFP (3 µg) was transferred to the cells using Microporator. This transfer took place using a 100 µL chip with one pulse at 1850 V for 20 ms, or with two pulses at 1200 V for 30 ms. The transfected cells were transferred to a CELLstart-coated 6-well culture plate (Falcon) containing 3 mL of StemPro MSC SFM, and cultured at 37° C. in the presence of 5% $CO_2$ for 7 days. The results are shown in FIG. 28. When the xeno-free medium (StemPro MSC-SFM) was used, the transfer efficiency was low under the conditions of 1850 V, 20 ms, 1 pulse. However, when the conditions were changed to 1200 V, 30 ms, 2 pulses, the cell survival rate and transfer efficiency increased. Hence, the latter conditions were employed for the transfection that followed.

Figure 29:
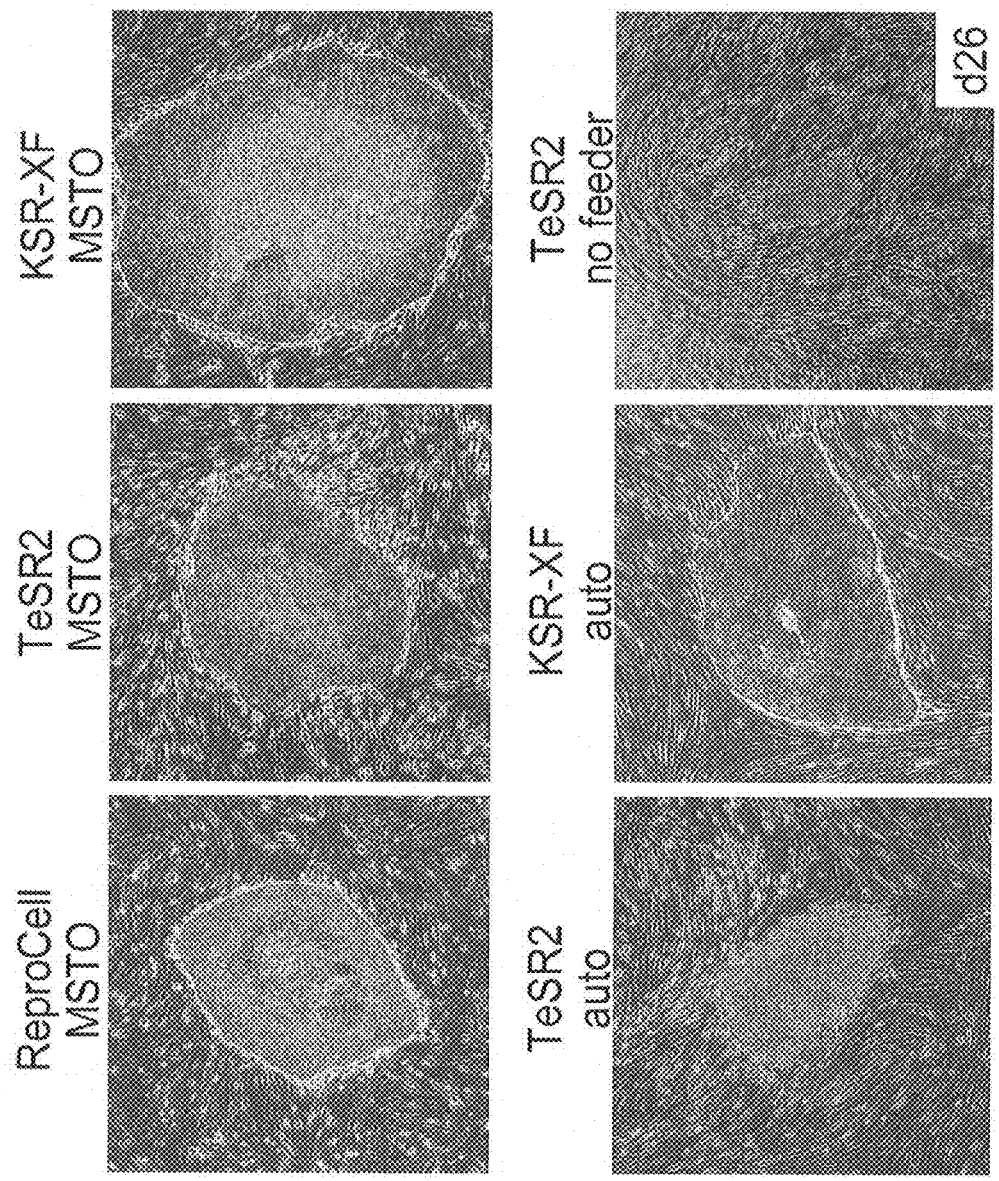
FIG. 29 is a photographic representation of the morphology of ES cell-like colonies that emerged on day 26 after transfection under Xeno-free conditions following cell culture under the six different conditions shown in Table 9.

The three different plasmids pCXLE-hOct4-shp53, pCXLE-hSK and pCXLE-hUL were used for reprogramming. In the experiments, the dental pulp stem cell line DP74 was used. The DP74 line was cultured and maintained at 37° C. in the presence of 5% $CO_2$ in a CELLstart-coated 100 mm culture dish using StemPro MSC-SFM as a culture broth. At the time of plasmid transfer, the medium was removed, and the cells were washed by the addition of 5 mL of PBS. After removing the PBS, TripLE select (Invitrogen) was added, and a reaction was carried out at 37° C. for about 5 minutes. After the cells rose, StemPro MSC-SFM was added to suspend the cells, and the cells were recovered in a 15 mL centrifugal tube. The suspension was centrifuged at 800 rpm for 5 minutes, and the supernatant was removed. After the cells were again suspended in StemPro MSC-SFM, $6 \times 10^5$ cells were recovered in a 1.5 mL tube. The suspension was centrifuged at 800 rpm for 5 minutes, and the supernatant was removed. The three different plasmids (1 μg each, 3 μg in total) were transferred to the cells using Microporator. This transfer took place using a 100 μL chip with two pulses at 1200 V for 30 ms. The transfected cells were transferred to a CELLstart-coated 6-well culture plate (Falcon) containing 3 mL of StemPro MSC-SFM, and cultured at 37° C. in the presence of 5% $CO_2$ for 7 days. The medium was then removed, and the cells were washed by the addition of 2 mL of PBS. After removing the PBS, TripLE select (Invitrogen) was added, and a reaction was carried out at 37° C. for about 5 minutes. After the cells rose, StemPro MSC-SFM was added to suspend the cells, and the cells were recovered into a 15 mL centrifugal tube. The suspension was centrifuged at 800 rpm for 5 minutes, and the supernatant was removed. After the cells were again suspended in StemPro MSC-SFM, $1 \times 10^5$ cells were seeded to a 100 mm dish under the various conditions shown in Table 9. The following day, the medium was replaced with the media shown in Table 9; this medium exchange was continued every 2 days. Photographs of the human ES cell-like colonies that emerged on day 26 after the transfer are shown in FIG. 29.

TABLE 9

| No. | Medium | Feeder cells |
| --- | --- | --- |
| 1 | ReproCELL medium | MSTO |
| 2 | TeSR2 | MSTO |
| 3 | KSR-XF | MSTO |
| 4 | TeSR2 | DP74 cells (self-feeder, CELLstart) |

TABLE 9-continued

| No. | Medium | Feeder cells |
| --- | --- | --- |
| 5 | KSR-XF | DP74 cells (self-feeder, CELLstart) |
| 6 | TeSR2 | No feeder cells (coated with CELLstart) |

Whichever media and feeder cells were used, iPS colonies could be established. The results for Nos. 4 to 6 (all obtained under xeno-free conditions) in Table 9, in particular, demonstrate that an iPS cell can be established and maintained from a dental pulp stem cell under virus-free conditions using episomal vectors, and under completely xeno-free conditions from the time of transfection.

Example 15

Establishment of iPS Cells from Human Peripheral Blood Mononuclear Cells.

Three microgram of expression plasmids (one microgram of pCXLE-hOct4-shp53, pCXLE-hSK and pCXLE-hUL) were electroporated into freshly isolated peripheral mononuclear cells ($5.0 \times 10^6$) with Nucleofector (Lonza) with Human T cell kit according to the manufacturer's instructions. We used condition of program V-24. Six hours later, transfected blood cells were stimulated with cytokines (IL-6, sIL-6R, SCF, TPO, Flit3/4-ligand, and IL-2) and anti-CD3/CD28 antibodies. After 2 days, the cells were seeded onto 6-well plate covered with MEF feeder. Culture medium was then gradually changed from X-vivo 10 supplemented with IL-6, sIL-6R, SCF, TPO, Flit3/4-ligand, and IL-2 to hES medium after seeding as illustrated in FIG. 36a. Colonies were photographed on day 29 (FIG. 36b). We could establish human iPS colonies that had a flat hESC-like morphology.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

In addition, the contents disclosed in any publication cited herein, including patents and patent applications, are hereby incorporated in their entireties by reference, to the extent that they have been disclosed herein.

This application is based on U.S. provisional patent application Nos. 61/232,402 and 61/307,306, the contents of which are hereby incorporated by reference.

The invention claimed is:

1. A method of producing iPS cells in vitro, comprising introducing
   (a) an episomal vector comprising a nucleic acid sequence that encodes Oct3/4,
   (b) an episomal vector comprising a nucleic acid sequence that encodes Klf4,
   (c) an episomal vector comprising a nucleic acid sequence that encodes Sox2,
   (d) an episomal vector comprising a nucleic acid sequence that encodes
      (i) L-Myc, and
      (ii) Lin28 or Lin28b joined polycistronically in the orientation of 5'-3', and
   (e) a functional inhibitor of p53 selected from the group consisting of
      (i) an siRNA against p53,
      (ii) an shRNA against p53, and
      (iii) DNA encoding an siRNA or shRNA against p53, wherein the DNA can be in the form of an episomal vector,
   into a somatic cell such that iPS cells are produced,
   wherein the episomal vectors of (a) to (e) can be the same or different.

2. The method according to claim 1, wherein the somatic cell is a human cell.

3. The method according to claim 2, comprising culturing the human cell in the absence of an ingredient from a non-human animal after introducing (a), (b), (c), (d), and (e) into the somatic cell.

4. The method of claim 1, wherein b) and c) the same.

5. The method of claim 4, wherein a) and e) are in the same.

6. The method of claim 1, wherein a) and e) are in the same.

* * * * *

SEQUENCE LISTING

```
<160> NUMBER OF SEQ ID NOS: 63

<210> SEQ ID NO 1
<211> LENGTH: 1782
<212> TYPE: DNA
<213> ORGANISM: Mus musculus
<220> FEATURE:
<221> NAME/KEY: CDS
<222> LOCATION: (129)..(1301)

<400> SEQUENCE: 1
aagttctgta gcttcagttc attgggacca tcctggctgt aggtagcgac tacagttagg      60
gggcacctag cattcaggcc ctcatcctcc tccttcccag cagggtgtca cgcttctccg     120 aagactgg atg act gcc atg gag gag tca cag tcg gat atc agc ctc gag     170
```

```
            Met Thr Ala Met Glu Glu Ser Gln Ser Asp Ile Ser Leu Glu
            1               5                   10
ctc cct ctg agc cag gag aca ttt tca ggc tta tgg aaa cta ctt cct       218
Leu Pro Leu Ser Gln Glu Thr Phe Ser Gly Leu Trp Lys Leu Leu Pro
15                  20                  25                  30 cca gaa gat atc ctg cca tca cct cac tgc atg gac gat ctg ttg ctg       266
Pro Glu Asp Ile Leu Pro Ser Pro His Cys Met Asp Asp Leu Leu Leu
                35                  40                  45 ccc cag gat gtt gag gag ttt ttt gaa ggc cca agt gaa gcc ctc cga       314
Pro Gln Asp Val Glu Glu Phe Phe Glu Gly Pro Ser Glu Ala Leu Arg
            50                  55                  60 gtg tca gga gct cct gca gca cag gac cct gtc acc gag acc cct ggg       362
Val Ser Gly Ala Pro Ala Ala Gln Asp Pro Val Thr Glu Thr Pro Gly
        65                  70                  75 cca gtg gcc cct gcc cca gcc act cca tgg ccc ctg tca tct ttt gtc       410
Pro Val Ala Pro Ala Pro Ala Thr Pro Trp Pro Leu Ser Ser Phe Val
    80                  85                  90 cct tct caa aaa act tac cag ggc aac tat ggc ttc cac ctg ggc ttc       458
Pro Ser Gln Lys Thr Tyr Gln Gly Asn Tyr Gly Phe His Leu Gly Phe
95                  100                 105                 110 ctg cag tct ggg aca gcc aag tct gtt atg tgc acg tac tct cct ccc       506
Leu Gln Ser Gly Thr Ala Lys Ser Val Met Cys Thr Tyr Ser Pro Pro
                115                 120                 125 ctc aat aag cta ttc tgc cag ctg gcg aag acg tgc cct gtg cag ttg       554
Leu Asn Lys Leu Phe Cys Gln Leu Ala Lys Thr Cys Pro Val Gln Leu
            130                 135                 140 tgg gtc agc gcc aca cct cca gct ggg agc cgt gtc cgc gcc atg gcc       602
Trp Val Ser Ala Thr Pro Pro Ala Gly Ser Arg Val Arg Ala Met Ala
        145                 150                 155 atc tac aag aag tca cag cac atg acg gag gtc gtg aga cgc tgc ccc       650
Ile Tyr Lys Lys Ser Gln His Met Thr Glu Val Val Arg Arg Cys Pro
    160                 165                 170 cac cat gag cgc tgc tcc gat ggt gat ggc ctg gct cct ccc cag cat       698
His His Glu Arg Cys Ser Asp Gly Asp Gly Leu Ala Pro Pro Gln His
175                 180                 185                 190 ctt atc cgg gtg gaa gga aat ttg tat ccc gag tat ctg gaa gac agg       746
Leu Ile Arg Val Glu Gly Asn Leu Tyr Pro Glu Tyr Leu Glu Asp Arg
                195                 200                 205 cag act ttt cgc cac agc gtg gtg gta cct tat gag cca ccc gag gcc       794
Gln Thr Phe Arg His Ser Val Val Val Pro Tyr Glu Pro Pro Glu Ala
            210                 215                 220 ggc tct gag tat acc acc atc cac tac aag tac atg tgt aat agc tcc       842
Gly Ser Glu Tyr Thr Thr Ile His Tyr Lys Tyr Met Cys Asn Ser Ser
        225                 230                 235 tgc atg ggg ggc atg aac cgc cga cct atc ctt acc atc atc aca ctg       890
Cys Met Gly Gly Met Asn Arg Arg Pro Ile Leu Thr Ile Ile Thr Leu
    240                 245                 250 gaa gac tcc agt ggg aac ctt ctg gga cgg gac agc ttt gag gtt cgt       938
Glu Asp Ser Ser Gly Asn Leu Leu Gly Arg Asp Ser Phe Glu Val Arg
255                 260                 265                 270 gtt tgt gcc tgc cct ggg aga gac cgc cgt aca gaa gaa gaa aat ttc       986
Val Cys Ala Cys Pro Gly Arg Asp Arg Arg Thr Glu Glu Glu Asn Phe
                275                 280                 285 cgc aaa aag gaa gtc ctt tgc cct gaa ctg ccc cca ggg agc gca aag      1034
Arg Lys Lys Glu Val Leu Cys Pro Glu Leu Pro Pro Gly Ser Ala Lys
            290                 295                 300 aga gcg ctg ccc acc tgc aca agc gcc tct ccc ccg caa aag aaa aaa      1082
Arg Ala Leu Pro Thr Cys Thr Ser Ala Ser Pro Pro Gln Lys Lys Lys
        305                 310                 315
```

-continued

```
cca ctt gat gga gag tat ttc acc ctc aag atc cgc ggg cgt aaa cgc       1130
Pro Leu Asp Gly Glu Tyr Phe Thr Leu Lys Ile Arg Gly Arg Lys Arg
    320                 325                 330 ttc gag atg ttc cgg gag ctg aat gag gcc tta gag tta aag gat gcc       1178
Phe Glu Met Phe Arg Glu Leu Asn Glu Ala Leu Glu Leu Lys Asp Ala
335                 340                 345                 350 cat gct aca gag gag tct gga gac agc agg gct cac tcc agc tac ctg       1226
His Ala Thr Glu Glu Ser Gly Asp Ser Arg Ala His Ser Ser Tyr Leu
                355                 360                 365 aag acc aag aag ggc cag tct act tcc cgc cat aaa aaa aca atg gtc       1274
Lys Thr Lys Lys Gly Gln Ser Thr Ser Arg His Lys Lys Thr Met Val
            370                 375                 380 aag aaa gtg ggg cct gac tca gac tga ctgcctctgc atcccgtccc             1321
Lys Lys Val Gly Pro Asp Ser Asp
                385                 390 catcaccagc ctcccctct ccttgctgtc ttatgacttc agggctgaga cacaatcctc      1381
ccggtcccct ctgctgcctt ttttaccttg tagctagggc tcagcccct ctctgagtag      1441 tggttcctgg cccaagttgg ggaataggtt gatagttgtc aggtctctgc tggcccagcg     1501
aaattctatc cagccagttg ttggaccctg gcacctacaa tgaaatctca ccctacccca    1561
caccctgtaa gattctatct tgggccctca tagggtccat atcctccagg cctacttttc    1621
cttccattct gcaaagcctg tctgcattta tccacccccc accctgtctc cctctttttt    1681 tttttttttac ccctttttat atatcaattt cctattttac aataaaattt tgttatcact    1741
taaaaaaaaa aaaaaaaaaa aaaaaaaaaa aaaaaaaaa a                         1782
```

<210> SEQ ID NO 2
<211> LENGTH: 390
<212> TYPE: PRT
<213> ORGANISM: Mus musculus

<400> SEQUENCE: 2

```
Met Thr Ala Met Glu Glu Ser Gln Ser Asp Ile Ser Leu Glu Leu Pro
1               5                   10                  15

Leu Ser Gln Glu Thr Phe Ser Gly Leu Trp Lys Leu Leu Pro Pro Glu
                20                  25                  30

Asp Ile Leu Pro Ser Pro His Cys Met Asp Asp Leu Leu Leu Pro Gln
            35                  40                  45

Asp Val Glu Glu Phe Phe Glu Gly Pro Ser Glu Ala Leu Arg Val Ser
        50                  55                  60

Gly Ala Pro Ala Ala Gln Asp Pro Val Thr Glu Thr Pro Gly Pro Val
65                  70                  75                  80

Ala Pro Ala Pro Ala Thr Pro Trp Pro Leu Ser Ser Phe Val Pro Ser
                85                  90                  95

Gln Lys Thr Tyr Gln Gly Asn Tyr Gly Phe His Leu Gly Phe Leu Gln
                100                 105                 110

Ser Gly Thr Ala Lys Ser Val Met Cys Thr Tyr Ser Pro Pro Leu Asn
            115                 120                 125

Lys Leu Phe Cys Gln Leu Ala Lys Thr Cys Pro Val Gln Leu Trp Val
        130                 135                 140

Ser Ala Thr Pro Pro Ala Gly Ser Arg Val Arg Ala Met Ala Ile Tyr
145                 150                 155                 160

Lys Lys Ser Gln His Met Thr Glu Val Val Arg Arg Cys Pro His His
                165                 170                 175

Glu Arg Cys Ser Asp Gly Asp Gly Leu Ala Pro Pro Gln His Leu Ile
                180                 185                 190
```

```
Arg Val Glu Gly Asn Leu Tyr Pro Glu Tyr Leu Glu Asp Arg Gln Thr
        195                 200                 205

Phe Arg His Ser Val Val Pro Tyr Glu Pro Glu Ala Gly Ser
210                 215                 220

Glu Tyr Thr Thr Ile His Tyr Lys Tyr Met Cys Asn Ser Ser Cys Met
225                 230                 235                 240

Gly Gly Met Asn Arg Arg Pro Ile Leu Thr Ile Ile Thr Leu Glu Asp
                245                 250                 255

Ser Ser Gly Asn Leu Leu Gly Arg Asp Ser Phe Glu Val Arg Val Cys
            260                 265                 270

Ala Cys Pro Gly Arg Asp Arg Arg Thr Glu Glu Asn Phe Arg Lys
            275                 280                 285

Lys Glu Val Leu Cys Pro Glu Leu Pro Pro Gly Ser Ala Lys Arg Ala
290                 295                 300

Leu Pro Thr Cys Thr Ser Ala Ser Pro Pro Gln Lys Lys Lys Pro Leu
305                 310                 315                 320

Asp Gly Glu Tyr Phe Thr Leu Lys Ile Arg Gly Arg Lys Arg Phe Glu
                325                 330                 335

Met Phe Arg Glu Leu Asn Glu Ala Leu Glu Leu Lys Asp Ala His Ala
                340                 345                 350

Thr Glu Glu Ser Gly Asp Ser Arg Ala His Ser Ser Tyr Leu Lys Thr
                355                 360                 365

Lys Lys Gly Gln Ser Thr Ser Arg His Lys Lys Thr Met Val Lys Lys
            370                 375                 380

Val Gly Pro Asp Ser Asp
385                 390

<210> SEQ ID NO 3
<211> LENGTH: 2586
<212> TYPE: DNA
<213> ORGANISM: Homo sapiens
<220> FEATURE:
<221> NAME/KEY: CDS
<222> LOCATION: (198)..(1379)

<400> SEQUENCE: 3
gattggggtt ttcccctccc atgtgctcaa gactggcgct aaaagttttg agcttctcaa        60
aagtctagag ccaccgtcca gggagcaggt agctgctggg ctccggggac actttgcgtt       120
cgggctggga gcgtgctttc acgacggtg acacgcttcc ctggattggc agccagactg        180
ccttccgggt cactgcc atg gag gag ccg cag tca gat cct agc gtc gag          230
                 Met Glu Glu Pro Gln Ser Asp Pro Ser Val Glu
                  1               5                  10 ccc cct ctg agt cag gaa aca ttt tca gac cta tgg aaa cta ctt cct         278
Pro Pro Leu Ser Gln Glu Thr Phe Ser Asp Leu Trp Lys Leu Leu Pro
            15                  20                  25 gaa aac aac gtt ctg tcc ccc ttg ccg tcc caa gca atg gat gat ttg         326
Glu Asn Asn Val Leu Ser Pro Leu Pro Ser Gln Ala Met Asp Asp Leu
        30                  35                  40 atg ctg tcc ccg gac gat att gaa caa tgg ttc act gaa gac cca ggt         374
Met Leu Ser Pro Asp Asp Ile Glu Gln Trp Phe Thr Glu Asp Pro Gly
    45                  50                  55 cca gat gaa gct ccc aga atg cca gag gct gct ccc ccc gtg gcc cct         422
Pro Asp Glu Ala Pro Arg Met Pro Glu Ala Ala Pro Pro Val Ala Pro
60                  65                  70                  75 gca cca gca gct cct aca ccg gcg gcc cct gca cca gcc ccc tcc tgg         470
Ala Pro Ala Ala Pro Thr Pro Ala Ala Pro Ala Pro Ala Pro Ser Trp
```

-continued

```
                      80                  85                  90
ccc ctg tca tct tct gtc cct tcc cag aaa acc tac cag ggc agc tac        518
Pro Leu Ser Ser Ser Val Pro Ser Gln Lys Thr Tyr Gln Gly Ser Tyr
             95                 100                 105 ggt ttc cgt ctg ggc ttc ttg cat tct ggg aca gcc aag tct gtg act        566
Gly Phe Arg Leu Gly Phe Leu His Ser Gly Thr Ala Lys Ser Val Thr
        110                 115                 120 tgc acg tac tcc cct gcc ctc aac aag atg ttt tgc caa ctg gcc aag        614
Cys Thr Tyr Ser Pro Ala Leu Asn Lys Met Phe Cys Gln Leu Ala Lys
    125                 130                 135 acc tgc cct gtg cag ctg tgg gtt gat tcc aca ccc ccg ccc ggc acc        662
Thr Cys Pro Val Gln Leu Trp Val Asp Ser Thr Pro Pro Gly Thr
140                 145                 150                 155 cgc gtc cgc gcc atg gcc atc tac aag cag tca cag cac atg acg gag        710
Arg Val Arg Ala Met Ala Ile Tyr Lys Gln Ser Gln His Met Thr Glu
                160                 165                 170 gtt gtg agg cgc tgc ccc cac cat gag cgc tgc tca gat agc gat ggt        758
Val Val Arg Arg Cys Pro His His Glu Arg Cys Ser Asp Ser Asp Gly
            175                 180                 185 ctg gcc cct cct cag cat ctt atc cga gtg gaa gga aat ttg cgt gtg        806
Leu Ala Pro Pro Gln His Leu Ile Arg Val Glu Gly Asn Leu Arg Val
        190                 195                 200 gag tat ttg gat gac aga aac act ttt cga cat agt gtg gtg gtg ccc        854
Glu Tyr Leu Asp Asp Arg Asn Thr Phe Arg His Ser Val Val Val Pro
    205                 210                 215 tat gag ccg cct gag gtt ggc tct gac tgt acc acc atc cac tac aac        902
Tyr Glu Pro Pro Glu Val Gly Ser Asp Cys Thr Thr Ile His Tyr Asn
220                 225                 230                 235 tac atg tgt aac agt tcc tgc atg ggc ggc atg aac cgg agg ccc atc        950
Tyr Met Cys Asn Ser Ser Cys Met Gly Gly Met Asn Arg Arg Pro Ile
                240                 245                 250 ctc acc atc atc aca ctg gaa gac tcc agt ggt aat cta ctg gga cgg        998
Leu Thr Ile Ile Thr Leu Glu Asp Ser Ser Gly Asn Leu Leu Gly Arg
            255                 260                 265 aac agc ttt gag gtg cgt gtt tgt gcc tgt cct ggg aga gac cgg cgc       1046
Asn Ser Phe Glu Val Arg Val Cys Ala Cys Pro Gly Arg Asp Arg Arg
        270                 275                 280 aca gag gaa gag aat ctc cgc aag aaa ggg gag cct cac cac gag ctg       1094
Thr Glu Glu Glu Asn Leu Arg Lys Lys Gly Glu Pro His His Glu Leu
    285                 290                 295 ccc cca ggg agc act aag cga gca ctg ccc aac aac acc agc tcc tct       1142
Pro Pro Gly Ser Thr Lys Arg Ala Leu Pro Asn Asn Thr Ser Ser Ser
300                 305                 310                 315 ccc cag cca aag aag aaa cca ctg gat gga gaa tat ttc acc ctt cag       1190
Pro Gln Pro Lys Lys Lys Pro Leu Asp Gly Glu Tyr Phe Thr Leu Gln
                320                 325                 330 atc cgt ggg cgt gag cgc ttc gag atg ttc cga gag ctg aat gag gcc       1238
Ile Arg Gly Arg Glu Arg Phe Glu Met Phe Arg Glu Leu Asn Glu Ala
            335                 340                 345 ttg gaa ctc aag gat gcc cag gct ggg aag gag cca ggg ggg agc agg       1286
Leu Glu Leu Lys Asp Ala Gln Ala Gly Lys Glu Pro Gly Gly Ser Arg
        350                 355                 360 gct cac tcc agc cac ctg aag tcc aaa aag ggt cag tct acc tcc cgc       1334
Ala His Ser Ser His Leu Lys Ser Lys Lys Gly Gln Ser Thr Ser Arg
    365                 370                 375 cat aaa aaa ctc atg ttc aag aca gaa ggg cct gac tca gac tga           1379
His Lys Lys Leu Met Phe Lys Thr Glu Gly Pro Asp Ser Asp
380                 385                 390 cattctccac ttcttgttcc ccactgacag cctcccaccc ccatctctcc ctcccctgcc    1439
```

```
attttgggtt ttgggtctttt gaacccttgc ttgcaatagg tgtgcgtcag aagcacccag    1499
gacttccatt tgctttgtcc cggggctcca ctgaacaagt tggcctgcac tggtgttttg    1559
ttgtggggag gaggatgggg agtaggacat accagcttag attttaaggt ttttactgtg    1619
agggatgttt gggagatgta agaaatgttc ttgcagttaa gggttagttt acaatcagcc    1679
acattctagg taggggccca cttcaccgta ctaaccaggg aagctgtccc tcactgttga    1739
attttctcta acttcaaggc ccatatctgt gaaatgctgg catttgcacc tacctcacag    1799
agtgcattgt gagggttaat gaaataatgt acatctggcc ttgaaaccac cttttattac    1859
atggggtcta gaacttgacc cccttgaggg tgcttgttcc ctctccctgt tggtcggtgg    1919
gttggtagtt tctacagttg ggcagctggt taggtagagg gagttgtcaa gtctctgctg    1979
gcccagccaa accctgtctg acaacctctt ggtgaacctt agtacctaaa aggaaatctc    2039
accccatccc acaccctgga ggatttcatc tcttgtatat gatgatctgg atccaccaag    2099
acttgtttta tgctcaggggt caatttcttt tttctttttt tttttttttt ttcttttttct    2159 ttgagactgg gtctcgcttt gttgcccagg ctggagtgga gtggcgtgat cttggcttac    2219
tgcagccttt gcctccccgg ctcgagcagt cctgcctcag cctccggagt agctgggacc    2279
acaggttcat gccaccatgg ccagccaact tttgcatgtt ttgtagagat ggggtctcac    2339
agtgttgccc aggctggtct caaactcctg ggctcaggcg atccacctgt ctcagcctcc    2399
cagagtgctg ggattacaat tgtgagccac cacgtccagc tggaagggtc aacatctttt    2459
acattctgca agcacatctg catttttcacc ccacccttcc cctccttctc cctttttata    2519
tcccattttt atatcgatct cttattttac aataaaactt tgctgccacc tgtgtgtctg    2579
aggggtg                                                               2586
```

<210> SEQ ID NO 4
<211> LENGTH: 393
<212> TYPE: PRT
<213> ORGANISM: Homo sapiens

<400> SEQUENCE: 4

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
            165                 170                 175

Pro His His Glu Arg Cys Ser Asp Ser Asp Gly Leu Ala Pro Pro Gln
        180                 185                 190

His Leu Ile Arg Val Glu Gly Asn Leu Arg Val Glu Tyr Leu Asp Asp
    195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
        260                 265                 270

Arg Val Cys Ala Cys Pro Gly Arg Asp Arg Arg Thr Glu Glu Glu Asn
    275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
        340                 345                 350

Ala Gln Ala Gly Lys Glu Pro Gly Gly Ser Arg Ala His Ser Ser His
    355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 5
<211> LENGTH: 56
<212> TYPE: DNA
<213> ORGANISM: Artificial Sequence
<220> FEATURE:
<223> OTHER INFORMATION: shRNA against p53

<400> SEQUENCE: 5
tttgactgga tgactgccat ggttcaagag accatggcag tcatccagtc tttttt        56

<210> SEQ ID NO 6
<211> LENGTH: 56
<212> TYPE: DNA
<213> ORGANISM: Artificial Sequence
<220> FEATURE:
<223> OTHER INFORMATION: shRNA against p53

<400> SEQUENCE: 6
tttgatatcc tgccatcacc tcttcaagag agaggtgatg gcaggatatc tttttt        56

<210> SEQ ID NO 7
<211> LENGTH: 56
<212> TYPE: DNA
<213> ORGANISM: Artificial Sequence
<220> FEATURE:
<223> OTHER INFORMATION: shRNA against p53

<400> SEQUENCE: 7
tttggcccaa gtgaagccct ccttcaagag aggagggctt cacttgggcc tttttt     56

<210> SEQ ID NO 8
<211> LENGTH: 56
<212> TYPE: DNA
<213> ORGANISM: Artificial Sequence
<220> FEATURE:
<223> OTHER INFORMATION: shRNA against p53

<400> SEQUENCE: 8
tttgtgaagc cctccgagtg tcttcaagag agacactcgg agggcttcac tttttt     56

<210> SEQ ID NO 9
<211> LENGTH: 56
<212> TYPE: DNA
<213> ORGANISM: Artificial Sequence
<220> FEATURE:
<223> OTHER INFORMATION: shRNA against p53

<400> SEQUENCE: 9
tttgccctcc gagtgtcagg agttcaagag actcctgaca ctcggagggc tttttt     56

<210> SEQ ID NO 10
<211> LENGTH: 56
<212> TYPE: DNA
<213> ORGANISM: Artificial Sequence
<220> FEATURE:
<223> OTHER INFORMATION: shRNA against p53

<400> SEQUENCE: 10
tttgtctgtt atgtgcacgt acttcaagag agtacgtgca cataacagac tttttt     56

<210> SEQ ID NO 11
<211> LENGTH: 56
<212> TYPE: DNA
<213> ORGANISM: Artificial Sequence
<220> FEATURE:
<223> OTHER INFORMATION: shRNA against p53

<400> SEQUENCE: 11
tttgtactct cctcccctca atttcaagag aattgagggg aggagagtac tttttt     56

<210> SEQ ID NO 12
<211> LENGTH: 56
<212> TYPE: DNA
<213> ORGANISM: Artificial Sequence
<220> FEATURE:
<223> OTHER INFORMATION: shRNA against p53

<400> SEQUENCE: 12
tttgctattc tgccagctgg cgttcaagag acgccagctg gcagaatagc tttttt     56

<210> SEQ ID NO 13
<211> LENGTH: 56
<212> TYPE: DNA
<213> ORGANISM: Artificial Sequence
<220> FEATURE:
<223> OTHER INFORMATION: shRNA against p53

<400> SEQUENCE: 13
tttgacgtgc cctgtgcagt tgttcaagag acaactgcac agggcacgtc tttttt     56

<210> SEQ ID NO 14
<211> LENGTH: 56
<212> TYPE: DNA
<213> ORGANISM: Artificial Sequence

```
<220> FEATURE:
<223> OTHER INFORMATION: shRNA against p53

<400> SEQUENCE: 14
tttgaagtca cagcacatga cgttcaagag acgtcatgtg ctgtgacttc tttttt      56

<210> SEQ ID NO 15
<211> LENGTH: 56
<212> TYPE: DNA
<213> ORGANISM: Artificial Sequence
<220> FEATURE:
<223> OTHER INFORMATION: shRNA against p53

<400> SEQUENCE: 15
tttgtcacag cacatgacgg agttcaagag actccgtcat gtgctgtgac tttttt      56

<210> SEQ ID NO 16
<211> LENGTH: 56
<212> TYPE: DNA
<213> ORGANISM: Artificial Sequence
<220> FEATURE:
<223> OTHER INFORMATION: shRNA against p53

<400> SEQUENCE: 16
tttggaaatt tgtatcccga gtttcaagag aactcgggat acaaatttcc tttttt      56

<210> SEQ ID NO 17
<211> LENGTH: 56
<212> TYPE: DNA
<213> ORGANISM: Artificial Sequence
<220> FEATURE:
<223> OTHER INFORMATION: shRNA against p53

<400> SEQUENCE: 17
tttgtacatg tgtaatagct ccttcaagag aggagctatt acacatgtac tttttt      56

<210> SEQ ID NO 18
<211> LENGTH: 56
<212> TYPE: DNA
<213> ORGANISM: Artificial Sequence
<220> FEATURE:
<223> OTHER INFORMATION: shRNA against p53

<400> SEQUENCE: 18
tttgactcca gtgggaacct tcttcaagag agaaggttcc cactggagtc tttttt      56

<210> SEQ ID NO 19
<211> LENGTH: 56
<212> TYPE: DNA
<213> ORGANISM: Artificial Sequence
<220> FEATURE:
<223> OTHER INFORMATION: shRNA against p53

<400> SEQUENCE: 19
tttgtccttt gccctgaact gcttcaagag agcagttcag ggcaaaggac tttttt      56

<210> SEQ ID NO 20
<211> LENGTH: 56
<212> TYPE: DNA
<213> ORGANISM: Artificial Sequence
<220> FEATURE:
<223> OTHER INFORMATION: shRNA against p53

<400> SEQUENCE: 20
tttgatccgc gggcgtaaac gcttcaagag agcgtttacg cccgcggatc tttttt      56
```

```
<210> SEQ ID NO 21
<211> LENGTH: 56
<212> TYPE: DNA
<213> ORGANISM: Artificial Sequence
<220> FEATURE:
<223> OTHER INFORMATION: shRNA against p53

<400> SEQUENCE: 21
tttgaccaag aagggccagt ctttcaagag aagactggcc cttcttggtc tttttt          56

<210> SEQ ID NO 22
<211> LENGTH: 56
<212> TYPE: DNA
<213> ORGANISM: Artificial Sequence
<220> FEATURE:
<223> OTHER INFORMATION: shRNA against p53

<400> SEQUENCE: 22
tttgaaagtg gggcctgact cattcaagag atgagtcagg ccccactttc tttttt          56

<210> SEQ ID NO 23
<211> LENGTH: 56
<212> TYPE: DNA
<213> ORGANISM: Artificial Sequence
<220> FEATURE:
<223> OTHER INFORMATION: shRNA against p53

<400> SEQUENCE: 23
tttgttgggg aataggttga tattcaagag atatcaacct attccccaac tttttt          56

<210> SEQ ID NO 24
<211> LENGTH: 56
<212> TYPE: DNA
<213> ORGANISM: Artificial Sequence
<220> FEATURE:
<223> OTHER INFORMATION: shRNA against p53

<400> SEQUENCE: 24
tttgattcta tctgggccc tcttcaagag agagggccca agatagaatc tttttt           56

<210> SEQ ID NO 25
<211> LENGTH: 59
<212> TYPE: DNA
<213> ORGANISM: Artificial Sequence
<220> FEATURE:
<223> OTHER INFORMATION: shRNA against p53

<400> SEQUENCE: 25
tttgcautac aggtacgtgt gtagtgtgct gtcctacaca tgtacttgta gtgttttttt      59

<210> SEQ ID NO 26
<211> LENGTH: 59
<212> TYPE: DNA
<213> ORGANISM: Artificial Sequence
<220> FEATURE:
<223> OTHER INFORMATION: shRNA against p53

<400> SEQUENCE: 26
tttgcagtut acttccgcc gtagtgtgct gtcctatggc gggaagtaga ctgttttttt      59

<210> SEQ ID NO 27
<211> LENGTH: 10
<212> TYPE: DNA
<213> ORGANISM: Artificial Sequence
<220> FEATURE:
<223> OTHER INFORMATION: p53 responsive element
```

<400> SEQUENCE: 27 rrrgwwcyyy                                                          10

<210> SEQ ID NO 28
<211> LENGTH: 48
<212> TYPE: DNA
<213> ORGANISM: Artificial Sequence
<220> FEATURE:
<223> OTHER INFORMATION: shRNA against p53

<400> SEQUENCE: 28
gactccagtg gtaatctact gctcgagcag tagattacca ctggagtc                48

<210> SEQ ID NO 29
<211> LENGTH: 34
<212> TYPE: DNA
<213> ORGANISM: Bacteriophage P1

<400> SEQUENCE: 29
ataacttcgt atagcataca ttatacgaag ttat                               34

<210> SEQ ID NO 30
<211> LENGTH: 34
<212> TYPE: DNA
<213> ORGANISM: Artificial Sequence
<220> FEATURE:
<223> OTHER INFORMATION: mutant loxP (lox71) sequence

<400> SEQUENCE: 30
taccgttcgt atagcataca ttatacgaag ttat                               34

<210> SEQ ID NO 31
<211> LENGTH: 34
<212> TYPE: DNA
<213> ORGANISM: Artificial Sequence
<220> FEATURE:
<223> OTHER INFORMATION: mutant loxP (lox66) sequence

<400> SEQUENCE: 31
ataacttcgt atagcataca ttatacgaac ggta                               34

<210> SEQ ID NO 32
<211> LENGTH: 47
<212> TYPE: DNA
<213> ORGANISM: Artificial Sequence
<220> FEATURE:
<223> OTHER INFORMATION: shRNA against p53

<400> SEQUENCE: 32
gactccagtg gtaatctact tcaagagagt agattaccac tggagtc                 47

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
acccatcctt cctgcccgat caga                                          24

<210> SEQ ID NO 34
<211> LENGTH: 24
<212> TYPE: DNA

```
<213> ORGANISM: Artificial Sequence
<220> FEATURE:
<223> OTHER INFORMATION: Primer

<400> SEQUENCE: 34
atcacaagtg tgggtggcgg tcct                                          24

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
gccgccgcct cagagtgcat cgac                                          24

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
cgagtggagg gaggcgctgc gtag                                          24

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
ttccacgagg gtagtgaacc                                               20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38 tcggggtgt tagagacaac                                                20

<210> SEQ ID NO 39
<211> LENGTH: 23
<212> TYPE: DNA
<213> ORGANISM: Artificial Sequence
<220> FEATURE:
<223> OTHER INFORMATION: Primer

<400> SEQUENCE: 39
atcagggcca agacatagag atg                                           23

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
gccaatgcaa cttggacgtt                                               20
```

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
gccaggaggt cttcgctgta                                               20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
aatgcacggc tagggtcaaa                                               20

<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
ccccagggcc ccattttggt acc                                           23

<210> SEQ ID NO 44
<211> LENGTH: 26
<212> TYPE: DNA
<213> ORGANISM: Artificial Sequence
<220> FEATURE:
<223> OTHER INFORMATION: Primer

<400> SEQUENCE: 44
acctcagttt gaatgcatgg gagagc                                        26

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
cattcaaact gaggtaaggg                                               20

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
tagcgtaaaa ggagcaacat ag                                            22

<210> SEQ ID NO 47
<211> LENGTH: 24
<212> TYPE: DNA
<213> ORGANISM: Artificial Sequence
<220> FEATURE:

```
<223> OTHER INFORMATION: Primer

<400> SEQUENCE: 47
acccatcctt cctgcccgat caga                                              24

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
ttggtaatgg agcggcggga cttg                                              24

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49
ccacctcgcc ttacacatga aga                                               23

<210> SEQ ID NO 50
<211> LENGTH: 22
<212> TYPE: DNA
<213> ORGANISM: Artificial Sequence
<220> FEATURE:
<223> OTHER INFORMATION: Primer

<400> SEQUENCE: 50
tagcgtaaaa ggagcaacat ag                                                22

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
ttcacatgtc ccagcactac caga                                              24

<210> SEQ ID NO 52
<211> LENGTH: 26
<212> TYPE: DNA
<213> ORGANISM: Artificial Sequence
<220> FEATURE:
<223> OTHER INFORMATION: Primer

<400> SEQUENCE: 52
tcacatgtgt gagagggca gtgtgc                                             26

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
ttcacatgtc ccagcactac caga                                              24
```

<210> SEQ ID NO 54
<211> LENGTH: 22
<212> TYPE: DNA
<213> ORGANISM: Artificial Sequence
<220> FEATURE:
<223> OTHER INFORMATION: Primer

<400> SEQUENCE: 54
tttgtttgac aggagcgaca at                                        22

<210> SEQ ID NO 55
<211> LENGTH: 26
<212> TYPE: DNA
<213> ORGANISM: Artificial Sequence
<220> FEATURE:
<223> OTHER INFORMATION: Primer

<400> SEQUENCE: 55
gcgaacccaa gacccaggcc tgctcc                                    26

<210> SEQ ID NO 56
<211> LENGTH: 25
<212> TYPE: DNA
<213> ORGANISM: Artificial Sequence
<220> FEATURE:
<223> OTHER INFORMATION: Primer

<400> SEQUENCE: 56 caggggtct gctcgcaccg tgatg                                      25

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
ggctgagaag aggatggcta c                                         21

<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
tttgtttgac aggagcgaca at                                        22

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
agccatatgg tagcctcatg tccgc                                     25

<210> SEQ ID NO 60
<211> LENGTH: 30
<212> TYPE: DNA
<213> ORGANISM: Artificial Sequence
<220> FEATURE:
<223> OTHER INFORMATION: Primer

```
<400> SEQUENCE: 60
tcaattctgt gcctccggga gcagggtagg                                      30

<210> SEQ ID NO 61
<211> LENGTH: 25
<212> TYPE: DNA
<213> ORGANISM: Artificial Sequence
<220> FEATURE:
<223> OTHER INFORMATION: Primer

<400> SEQUENCE: 61
agccatatgg tagcctcatg tccgc                                           25

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
tagcgtaaaa ggagcaacat ag                                              22

<210> SEQ ID NO 63
<211> LENGTH: 81
<212> TYPE: DNA
<213> ORGANISM: Foot-and-mouth disease virus

<400> SEQUENCE: 63
aaaattgtcg ctcctgtcaa acaaactctt aactttgatt tactcaaact ggctggggat     60
gtagaaagca atccaggtcc a                                               81
```